United States Patent
Lee et al.

(10) Patent No.: US 7,399,854 B2
(45) Date of Patent: *Jul. 15, 2008

(54) REGENTS LABELED WITH ENERGY TRANSFER DYES

(75) Inventors: Linda G. Lee, Palo Alto, CA (US); Sandra L. Spurgeon, San Mateo, CA (US); Barnett Rosenblum, San Jose, CA (US)

(73) Assignee: Applera Corporation, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/617,660

(22) Filed: Dec. 28, 2006

(65) Prior Publication Data

US 2007/0161026 A1 Jul. 12, 2007

Related U.S. Application Data

(63) Continuation of application No. 10/788,836, filed on Feb. 26, 2004, now Pat. No. 7,169,939, which is a continuation of application No. 10/014,743, filed on Oct. 29, 2001, now Pat. No. 6,849,745, which is a continuation of application No. 09/272,097, filed on Mar. 18, 1999, now Pat. No. 6,335,440, which is a continuation of application No. 09/046,203, filed on Mar. 23, 1998, now Pat. No. 5,945,526, which is a continuation of application No. 08/726,462, filed on Oct. 4, 1996, now Pat. No. 5,800,996, which is a continuation-in-part of application No. 08/642,330, filed on May 3, 1996, now Pat. No. 5,863,727, and a continuation-in-part of application No. 08/672,196, filed on Jun. 27, 1996, now Pat. No. 5,847,162.

(51) Int. Cl.
*C07H 19/04* (2006.01)
*C07D 311/82* (2006.01)
*C07D 311/78* (2006.01)

(52) U.S. Cl. ............... 536/26.6; 549/223; 549/224
(58) Field of Classification Search ............... 536/26.6; 549/223, 224
See application file for complete search history.

(56) References Cited

U.S. PATENT DOCUMENTS 3,679,358 A 7/1972 Lohe et al.

(Continued)

FOREIGN PATENT DOCUMENTS

CH 12433/70 2/1973

(Continued)

OTHER PUBLICATIONS

Abdel-Mottaleb, M.S.A., et al., "Photophysics and dynamics of coumarin laser dyes and their analytical implications," *Proc.-Indian Acad. Scie. Chem. Sci.*, 1992, 104: 185-196.

(Continued)

*Primary Examiner*—Jezia Riley

(57) ABSTRACT

Novel linkers for linking a donor dye to an acceptor dye in an energy transfer fluorescent dye are provided. These linkers faciliate the efficient transfer of energy between a donor and acceptor dye in an energy transfer dye. One of these linkers for linking a donor dye to an acceptor dye in an energy transfer fluorescent dye has the general structure $R_{21}Z_1C(O)R_{22}R_{28}$ where $R_{21}$ is a $C_{1-5}$ alkyl attached to the donor dye, $C(O)$ is a carbonyl group, $Z_1$ is either NH, sulfur or oxygen, $R_{22}$ is a substituent which includes an alkene, diene, alkyne, a five and six membered ring having at least one unsaturated bond or a fused ring structure which is attached to the carbonyl carbon, and $R_{28}$ includes a functional group which attaches the linker to the acceptor dye.

31 Claims, 16 Drawing Sheets

U.S. PATENT DOCUMENTS

| | | | |
|---|---|---|---|
| 4,318,846 A | 3/1982 | Khanna et al. | |
| 4,647,675 A | 3/1987 | Mayer et al. | |
| 4,777,128 A | 10/1988 | Lippa | |
| 4,855,225 A | 8/1989 | Fung et al. | |
| 4,996,143 A | 2/1991 | Heller et al. | |
| 5,118,802 A | 6/1992 | Smith et al. | |
| 5,188,934 A | 2/1993 | Menchen et al. | |
| 5,254,477 A | 10/1993 | Walt | |
| 5,326,692 A | 7/1994 | Brinkley et al. | |
| 5,340,716 A | 8/1994 | Ullman et al. | |
| 5,342,789 A | 8/1994 | Chick et al. | |
| 5,366,860 A | 11/1994 | Bergot et al. | |
| 5,401,847 A | 3/1995 | Glazer et al. | |
| 5,405,975 A | 4/1995 | Kuhn et al. | |
| 5,410,030 A | 4/1995 | Yue et al. | |
| 5,439,797 A | 8/1995 | Tsien et al. | |
| 5,453,517 A | 9/1995 | Kuhn et al. | |
| 5,532,129 A | 7/1996 | Heller | |
| 5,552,540 A | 9/1996 | Haralambidis | |
| 5,565,322 A | 10/1996 | Heller | |
| 5,565,554 A | 10/1996 | Glazer et al. | |
| 5,573,909 A | 11/1996 | Singer et al. | |
| 5,582,977 A | 12/1996 | Yue et al. | |
| 5,607,834 A | 3/1997 | Bagwell | |
| 5,646,264 A | 7/1997 | Glazer et al. | |
| 5,654,419 A | 8/1997 | Mathies et al. | |
| 5,688,648 A | 11/1997 | Mathies et al. | |
| 5,707,804 A | 1/1998 | Mathies et al. | |
| 5,728,528 A | 3/1998 | Mathies et al. | |
| 5,741,657 A | 4/1998 | Tsein et al. | |
| 5,760,201 A | 6/1998 | Glazer et al. | |
| 5,763,189 A | 6/1998 | Buechler et al. | |
| 5,800,996 A | 9/1998 | Lee et al. | |
| 5,824,799 A | 10/1998 | Buechler et al. | |
| 5,843,658 A | 12/1998 | Uchiyama et al. | |
| 5,847,162 A | 12/1998 | Lee et al. | |
| 5,851,778 A | 12/1998 | Oh et al. | |
| 5,853,992 A | 12/1998 | Glazer et al. | |
| 5,863,727 A | 1/1999 | Lee et al. | |
| 5,869,255 A | 2/1999 | Mathies et al. | |
| 5,945,283 A | 8/1999 | Kwok et al. | |
| 5,945,526 A | 8/1999 | Lee et al. | |
| 5,981,200 A | 11/1999 | Tsien et al. | |
| 6,008,373 A | 12/1999 | Waggoner et al. | |
| 6,028,190 A | 2/2000 | Mathies et al. | |
| 6,048,982 A | 4/2000 | Waggoner | |
| 6,291,162 B1 | 9/2001 | Tsien et al. | |
| 6,335,440 B1 | 1/2002 | Lee et al. | |
| 6,358,684 B1 | 3/2002 | Lee et al. | |
| 6,472,205 B1 | 10/2002 | Tsien et al. | |
| 6,849,745 B2 | 2/2005 | Lee et al. | |
| 7,169,939 B2 * | 1/2007 | Lee et al. | 549/223 |
| 2007/0154924 A1 | 7/2007 | Lee et al. | |
| 2007/0154925 A1 | 7/2007 | Lee et al. | |
| 2007/0154926 A1 | 7/2007 | Lee et al. | |
| 2007/0154927 A1 | 7/2007 | Lee et al. | |
| 2007/0161027 A1 | 7/2007 | Lee et al. | |
| 2007/0207477 A1 | 9/2007 | Lee et al. | |
| 2007/0212709 A1 | 9/2007 | Lee et al. | |

FOREIGN PATENT DOCUMENTS

| | | |
|---|---|---|
| DE | 45263 | 11/1887 |
| DE | 47451 | 11/1887 |
| DE | 108347 | 11/1898 |
| DE | 2049503 | 4/1971 |
| DE | 2049527 | 4/1971 |
| DE | 3425631 A1 | 1/1986 |
| EP | 0 201 751 A1 | 11/1986 |
| EP | 0 229 943 A2 | 7/1987 |
| EP | 0 299 943 A2 | 7/1987 |
| EP | 0 252 683 | 1/1988 |
| EP | 0 601 889 A2 | 6/1994 |
| EP | 0 747 700 A2 | 12/1996 |
| EP | 0 967 219 A1 | 12/1999 |
| GB | 1273454 | 5/1972 |
| GB | 1286885 | 8/1972 |
| GB | 2 301 833 | 12/1996 |
| JP | 0410735 A | 4/1992 |
| JP | 04107559 A | 9/1992 |
| JP | 5-60698 | 3/1993 |
| WO | WO 89/03041 A2 | 4/1989 |
| WO | WO 91/03476 | 3/1991 |
| WO | WO 91/05060 | 4/1991 |
| WO | WO 91/07507 | 5/1991 |
| WO | WO 92/00388 | 1/1992 |
| WO | WO9306482 | 4/1993 |
| WO | WO 93/09128 | 5/1993 |
| WO | WO 93/13224 | 7/1993 |
| WO | WO 93/23492 | 11/1993 |
| WO | WO 94/05688 | 3/1994 |
| WO | WO 94/17397 | 8/1994 |
| WO | WO 94/28166 | 12/1994 |
| WO | WO 95/21266 | 8/1995 |
| WO | WO 96/04405 | 2/1996 |
| WO | WO 96/30540 | 10/1996 |
| WO | WO 96/41166 | 12/1996 |
| WO | WO 97/11084 | 3/1997 |
| WO | WO 99/02544 | 1/1999 |

OTHER PUBLICATIONS

Anton, J.A., et al., "Transfer of Excitation Energy Between Porphyrin Centers of a Covalently-Linked Dimer," *Photochemistry and Photobiology*, 1978, 28: 235-242.

Asseline, U., et al., "Oligonucleotides Covalently Linked to Intercalating Dyes as Base Sequence-Specific Ligands: Influence of Dye Attachment Site," *EMBO Journal*, 1984, 3: 795-800.

Benson, S., et al., "Fluorescence Energy-Transfer Cyanine Heterodimers with High Affinity for Double-Stranded DNA-1. Synthesis and Spectroscopic Properties," *Analytical Biochemistry*, Jun. 1995, pp. 247-255.

Benson, S.C., et al., "Heterodimeric DNA-binding dyes designed for energy transfer: stability and applications of the DNA complexes," *Nucleic Acid Research*, Nov. 1993, 21: 5720-5726.

Benson, S.C., et al., "Heterodimeric DNA-binding dyes designed for energy transfer: synthesis and spectroscopic properties," *Nucleic Acids Research*, Nov. 1993, 21: 5727-5735.

Bergstrom, D., et al., "C-5 substituted Nucleoside Analogs," *SYNLETT*, 1992, 3: 179-188.

Bothner, A.A., et al., "Molecular Dynamic of covalently linked multi-porphyrin arrays," *J. Phys. Chem.*, 1996, 100: 17551-17557.

Brumbaugh, J., et al., "Continuous On-Line DNA Sequencing Using Oligonucleotide Primers with Multiple Fluorophores," *Proc. Natl. Acad. Sci. USA*, 1988, 85: 5610-5614.

Cardullo, R.A., et al., "Detection of nucleic acid hybridization by nonradiative fluorescence resonance energy transfer," *Proc. Natl. Acad. Sci. USA*, Dec. 1988, 85(23): 8790-8794.

Chiu, H.C., et al., "Electronic energy transfer between tyrosine and tryptophan in the peptides Tyr-(Pro)n-Tyr," *Biopolymers*, 1977, 16: 277.

Clegg, R.M., "Fluorescence resonance energy transfer and nucleic acids," *Method Enzymol*, 1992, 211: 353-388.

Conrad, R.H., et al., "Intramolecular transfer of excitation from tryptophan to 1-dimethylaminonapthalene-5-sulfonamide in a series of model compounds," *Biochemistry*, 1968, 7: 777.

Cooper, J., et al., "Analysis of Fluorescence Energy Transfer in Duplex and Branched DNA Molecules," *Biochemistry*, 1990, 29(39): 9261-9268.

Delaney, J.K., et al., "Electron tunneling in a cofacial zinc porphyrin-quinone cage molecule: Novel Temperature and solvent dependent," *J. Am. Chem. Soc.*, 1990, 112(3): 957-963.

Dirks, G., et al., "Light absorption and energy transfer in polyene-porphyrin esters," *Photochemistry and Photobiology*, 1980, 32: 277-280.

Drake, J.M., et al., "Chemical and Biological Microstructures as Probed by Dynamic Processes," *Science*, Mar. 1991, 251: 1574-1579.

Effenberger, F., et al., "Synthesis and optical properties of terminally substituted conjugated polyenes," *Agnew. Chem. Int. Ed. Engl.*, 1988, 27(2): 281-284.

Florkin, M., et al., "Mechanism of energy transfer," *Comprehensive Biochemistry*, 1967, 22: 61.

Forster, T., "Intermolecular Energy Migration and fluorescence," *Ann. Physik (Leipzig)*, 1948, 2: 55.

Gust, D., et al., "A synthetic system mimicking the energy transfer and charge separation of natural photosynthesis," *Journal of Photochemistry*, 1985, 27(2): 281-284.

Ha, T., et al., "Probing the Interaction between two single molecules: Fluorescence resonance energy transfer between a single donor and a single acceptor," *Biophysics*, Jun. 1996, 93: 6264-6268.

Haralambidis, J., et al., "Preparation of base-modified nucleosides suitable for non-radioactive label attachment and their incorporation into synthetic oligodeoxyribonucleotides," *Nucleic Acids Research*, 1987, 15(12): 4857-4876.

Hass, F.., et al., "Distribution of end to end Distances in oligopeptides in solution as estimated by energy transfer", *Proc. Natl. Acad. Sci. USA*, 1975, 72: 1807.

Haugland, R.P., "Fluorescence-Detected DNA Sequencing—Final Technical Report," Grant No. DE-FG06-88ER60684, Sep. 1990, 15 pages.

Haugland, R.P., "Fluorescent Labels," *Biosense. Fiberopt.*, 1991, 85-110.

Haugland, R.P., "Synthesis and applications of fluorescent probes," *Small Business Innovative Research Program, Phase II Grant Application*, 1988.

Haugland, R.P., "Synthesis and Biomedical Applications of Fluorescent Probes," *Small Business Innovative Research Program, Phase I Grant Application*, Dec. 1985.

Haugland, R.P., et al., "Dependence of the Kinetics of singlet-singlet energy transfer on spectral overlap," *Proc. Natl. Acad. Sci.*, 1969, 63: 23-30.

Haugland, R.P., et al., "New Dyes for DNA Sequencing," (Progress Report) Dec. 31, 1990.

Heller, M.J., et al., "Fluorescent energy transfer oligonucleotide probes," *Federation Proceedings*, 1987, 46(6) Abstract 248.

Hiroaki, O., et al., "Fluorescence energy transfer between specific-labeled sites on DNA," 1992, pp. 67-68.

Hiroaki, O., et al., "The Estimation of Distances Between Specific Backbone-Labeled Sites in DNA using Fluorescence Resonance Energy Transfer," *Nucleic Acids Research*, Sep. 1992, pp. 5205-5214.

Hirzel, T.K., "Singlet excitation transfer between terminal chromophores in 1,4-disubstituted bicyclo (2.2.2.) octanes and 4,4'-disubstrituted-1,1'dibicyclo (2.2.2) octyls", Ph.D. Dissertation 1980, Unversity of Wisconsin-Madison.

Hsiao, J.S., et al., "Soluble synthetic multiporphyrin arrays. Photodynamics of energy-transfer processes," *J. Am. Chem. Soc.* 1996, 118(45): 11181-11193.

Hung, S., et al., "Cyanine Dyes with High Absorption Cross Section as Donor Chromophores in Energy Transfer Primers," *Anal. Biochem.*, 1996, 243: 15-27.

Hung, S.C., et al., "Energy Transfer Primers with 5- or 6-carboxyrhodamine-6G a acceptor chromphores," *Anal. Biochem.*, 1996, 238:165-170.

Hwang, K.C., et al., "Synthesis of Amphipathic porphyrings and their photoinduced electron transfer reactions at the lipid bilayer-water interface," *Photochemistry and Photobiology*, 1994, 59:145-151.

Ju, J., et al., "Cassette Labeling for facile contruction of energy transfer fluorescent primers," *Nucleic Acid Res.*, 1996, 24: 1144-1148.

Ju, J., et al., "Design and synthesis of fluorescence energy transfer dye-labled primers and their application for DNA sequencing and analysis," *Anal. Biochem.*, Oct. 10, 1995, 231(1): 131-140.

Ju, J., et al., "Fluorescence energy transfer dye-labeled primers for DNA sequencing and analysis," University of California Berkeley, Jan. 1995, pp. 4347-4350.

Kang, H-C, et al., "New Dyes for DNA sequencing," *Human Genome 1989-90, Program report (U.S. Department of Energy, Office of Energy)*.

Katz, H.E., et al., "4-Piperidinylimino: A Nearly Linear Head-to-Tail linking Group for Dipolar Chromophores," *Journal of Organic Chemistry*, 1991, 56: 2282-2284.

Lamola, A.A., et al., "Intramolecular energy transfer between nonconjugated chromphores in some model compounds," *J. Am. Chem. Soc.*, 1965, 37:2322.

Latt, S.A., et al., "Energy transfer, A systems with relatively fixed donor-acceptor separation," *J. Am. Chem. Soc.*, 1965, 87: 995-1003.

Lee, L.G., et al., "Allelic discrimination by nick-translation PCR with fluorogenic probes," *Nucleic Acids Res.*, Aug. 11, 1993, 21(16): 3761-3766.

Lee, L.G., et al., "DNA sequencing with dye-labeled terminators and T7 DNA polymerase: effect of dyes and dNTPs on incorporation od dye-terminators and probability analysis of termination fragments," *Nucleic Acids Res.*, 1992, 20(10): 2471-2483.

Lerho, M.J., "Diffusion-enhanced fluorescence energy transfer (DEFET): Application to the study of ligands-DNA and chromatin interaction" Ph.D. Dissertation 1991, University of Belgium.

Lindsey, J.S., et al., "Excited-state porphyrin-quinone interactions at 10-A separation," *J. Am. Chem. Soc.*, 1982, 104(16): 4498-4500.

Lindsey, J.S., et al., "Photophysics of a cofacial-porphyrin-quinone cage molecule and related compounds: Fluorescence properties, flash transients, and electron-transfer reactions," *J. Am. Chem. Soc.*, 1988, 110(11): 3610-3621.

Lindsey, J.S., et al., "Synthesis of a cofacial porphyrin-quinone via entropically favored macropolycyclization," *J. Am. Chem. Soc..*, Aug. 11, 1982, 104(16): 4498-4500.

Lindsey, J.S., et al., "Visible light-harvesting in covalently-linked porphyrin-cyanine dyes," *Tetrahedron* 1989, 45(15): 4845-4866.

Livak, K.J. et al., "Oligonucleotides with fluorescent dyes at opposite ends provide a quenched probe system useful for detecting PCR product and nucleic acid hybridization," *PCR Method Appl.*, Jun. 1995, 4(6): 357-362.

Mergny, J., et al., "Fluorescence energy transfer as a probe for nucleic acid structures and sequences," *Nucleic Acids Research*, Feb. 1994, 22: 920-928.

Millar, D.P., et al., "Excited-state quenching of dye-linked oligonucleotides," *Proc. Spie-Int. Soc. Opt. Engl.*, 1992, 1640: 592-598.

"Molecular Probes Handbook of fluorescent probes and research chemicals," 1992-1994, 5th Ed., Molecular Probes, Inc.

Moore, A.L., et al., "Energy transfer from carontenoid polyenes to porphyrins: A light harvesting antenna," *Photochemistry and Photobiology*, 1980, 32: 691-695.

Mugnier, J., et al., "Efficiency of intramolecular energy transfer in coumarin bichromophoric molecules," *J. Lumin.*, 1985, 33: 273.

Mugnier, J., et al., "Rate of intramolecular electronic energy transfer in coumarin bichromophoric molecules. An investigation by multifrequency phase modulation fluorometry," *Chem. Phys. Lett.*, 1985, 119: 217.

Mujurndar, et al., "Cyanine Dye Labeling Reagents: Sulfoindocyanine Succinimidyl Esters," *Bioconjugate Chemistry*, 1993, 4: 105-111.

Mujurndar, S.R., et al., "Cyanine-labeling reagents: Sulfobenzindocyanine Succinimidyl Esters," *Bioconjugate Chem*, 1996, 7: 356-362.

Nakagaki, R., et al., "Photochemistry of bichromophoric chain molecules containing electron donor and acceptor moieties. Dependence of reaction pathways on the nitrophenoxy)alkyl)arulines," *Chem. Phys. Lett.*, 1985, 121: 262-266.

Oliver, A.M., et al., "Strong Effects of the Bridge Configuration on Photoinduced Charge Separation in Rigidly Linked Donor-Acceptor Systems," *Chemical Physical Letters*, Sep. 1988, 150: 366-373.

Pispisa, B., et al., "Photophysical behavior or Poly(L-lysine) carrying Porphyrin and Naphthyl Chromophors," *Biopolymers*, 1994, 34: 435-442.

Prathapan, S., et al., "Building-block synthesis of porphyrin light0harvesting arrays," *J. Am. Chem. Soc.*, 1993, 115(16): 7519-7520.

Prober, J.M., et al., "A system for rapid DNA sequencing with fluorescent chain-terminating didoxynucleotides," *Science*, 1987, 238: 238-341.

Rice, K.G., et al., "Interterminal Distance and Flexibility of a Triantennary Glycopeptide As Measured by Resonance Energy Transfer," *Biochemistry* 1991, 30:6646-6655.

Sauer, M., et al., "Design of Multiplex Dyes," *Ber. Bun. Gesell. Phys. Chem.*, 1993, 97: 1734-1737.

Schaefer, F.P., *Chem. Phys. Lett.*, 1978, 56: 455.

Schaefer, F.P., et al., "Intermolecular TT-energy transfer in bifluorophoric laser dyes," *Appl. Phys. B.*, 1982, B28(1): 37-41.

Scherer, T., et al., "Comparison of Flexibly and Rigidly Bridged Donor-Acceptor Systems: Solvent Induced Switching Between Folded and Extended Emissive Charge-Transfer States", *Recueil des Travaux Chimiques des Pays-Bas*, 1991, 110: 95-96.

Schnepp, O., et al., "Intramolecular energy transfer in a naphthalene-anthracene system," *J. Am. Chem. Soc.*, 1962, 84: 172.

Scholes, G.D., et al., "Intramolecular Electronic Energy Transfer between Rigidly Linked Napthalene and Anthracene Chromophores," *Journal of Physical Chemistry*, 1993, 97: 11871-11876.

Selvin, P.R., "Fluorescence Resonance Energy Transfer," *Method in Enzymology*, 1995, 246: 300-335.

Seth, J., et al., "Investigation of electronic communication in multi-porphyrin light-harvesting arrays," *J. Am. Chem. Soc.*, 1994, 116(23): 10578-10592.

Shipchandler, M.T., et al., "4-[Aminomethylfluorescein and its N-alkyl derivatives: useful reagents immunodiagnostic techniques," *Anal. Biochem.*, Apr. 1987, 162(1):89-101.

Speiser, S., et al., "Intramolecular electronic energy transfer via exhange interaction in bichromophoric molecules," *Chem. Phys. Lett.*, 1983, 102, 88-94.

Stenzel, R., et al., "Cross-Reactivity of Anti0Digoxin Antibodies with Digitoxin Depends on Trancer Structure," *Clin. Chem.*, 1992, 38(11): 2228-2232.

Stryer, L., et al., "Energy Transfer: A Spectroscopic Ruler," *Proc. Natl. Acad. Sci. USA*, 1967, 58: 719-726.

Tamaki, T., "Intramolecular interaction between the phenol and indole chromophore," *Bull. Soc. Chem.*, Japan, 1973, 46: 2527.

Tanke, H., "What's new from the field: Current developments in flow cytometry and fluorescent labels," Advertisement, *Molecular Probes, Inc.*, 1989, pp. 63-65.

Thornton, N.B., et al., "Chromophore-quencher Probes for DNA," *New Journal of Chemistry*, 1996, 20: 791-800.

Tian, H., et al., "Bichromophoric Rhodamine Dyes and Their Fluorescence Properties," *Dyes Pigm.*, 1994, 26: 159-165.

Tian, H. et al., "Solvent Effect on the triplet lifetime of some rhodamine dyes," *Dyes. Pigm.*, 1994, 26: 167-174.

Tyagi, S., et al., "Molecular Beacons: Probes that Fluorescence upon Hybridization," *Nature Biotechnology*, Mar. 1996, 14: 303-308.

Valeur, B., et al., "Calculation of the Distribution of Donor-Acceptor Distances in Flexible Bichromophoric Molecules. Application to Intramolecular Transfer of Excitation Energy," *The Journal of Physical Chemistry*, Dec. 1989, 93:6073-6079.

Vamosi, G.; et al., "Fluorescence characteristics of 5-carboxyetramethylrhodamine linked covalently to the 5' end of oligonucleotides: multiple conformers of single0stranded and double-stranded dye-DNA complexes," *Biophys. J.*, 1996, 71: 972-994.

Wagner, R.W., et al., "Synthesis of facially encumbered porphyrins. An approach to light harvesting antenna complexes," *Tetrahedron Letters*, 1991, 32(14): 1703-1706.

Wagner, R.W., et al., "A molecular photonic wire," *J. Am. Chem. Soc.*, 1994, 116(21): 9759-9760.

Wagner, R.W., et al., "Self-assembly of molecular devices containing a ferrocene, a porphyrin and a quinine in a triple macrocyclic architectures," *J. Chem. Soc. Chem. Commun.*, 1991, No. 20, pp. 1463-1466.

Wagner, R.W., et al., "Synthesis of porphyrins tailored with eight facially-encumbering groups. An approach to solid state light harvesting complexes," *Tetrahedron*, 1994, 50(38): 11097-11112.

Wang, Y., et al., "Photochemical Probes of Intramolecular Electron and Energy Transfer," *Chemical Physics*, Mar. 1993, 176: 305-319.

Wasielewski, M.R., et al., "Ultrafast carotenoid to pheophorbide energy transfer in a biomimetic model for antenna function in photosynthesis," *Nature*, 1986, 322: 570-572.

Weber, G., et al., "Fluorescene excitation spectrum of organic compounds in solution part 1. Systems with Quantum yield independent of exciting wavelength," *Trans. Faraday Soc.*, 1958, 54: 640.

Weiss, S., et al., "Probing the interaction between single molecules: fluorescence resonance energy transfer between a single donor and a single acceptor," *Conference title: QELS '96. Summaries of papers presented at the quantum electronics and laser science Conference*. vol. 10 1996 Technical Digest Series. Conference Edition (IEEE Cat. No. 96CH35902).

Wu, P., et al., "Resonance energy transfer: methods and applications," *Anal. Biochem.*, Apr. 1994, 218(1): 1-13.

Yang, J., et al., "Fluorescence energy transfer studies in a cross-linked polyurethane network," *Can. J. Chem.*, 1995, 73: 1823-1830.

Yuan, P., "Photophysical behavior in bichromophores and energy transfer basic indicators," Ph.D. Dissertation, 1991, Tufts University.

Zheng, Z., et al., "Fluorescence energy-transfer cyanine heterodimers with High affinity for double-stranded DNA. II. Applications to multiplex restriction fragment sizing," *Anal. Biochem.*, 1995, 231:256-260.

Zhu, Z., et al., "Directly labeled DNA probes using fluorescent nucleotides with different lengh linkers," *Nucleic Acids Research*, 1994, 22(16): 3418-3422.

U.S. Appl. No. 11/617,650, filed Dec. 28, 2006, Lee et al.
U.S. Appl. No. 11/618,667, filed Dec. 29, 2006, Lee et al.

* cited by examiner

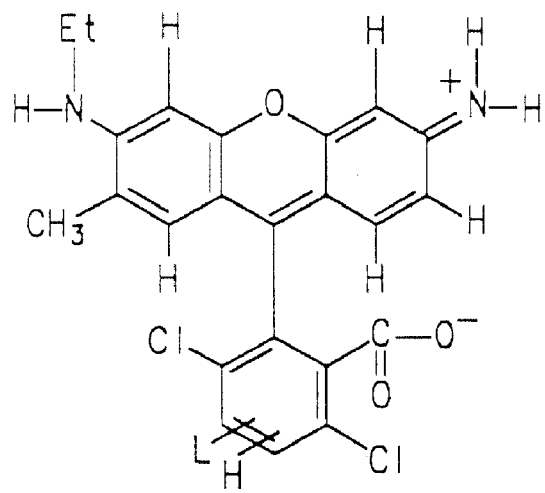
FIG. 3A-A
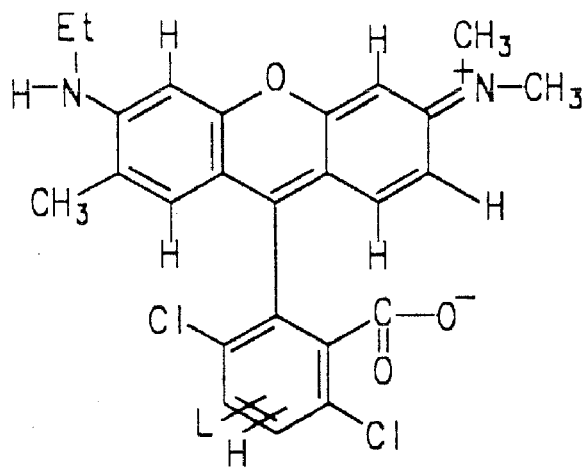
FIG. 3A-B
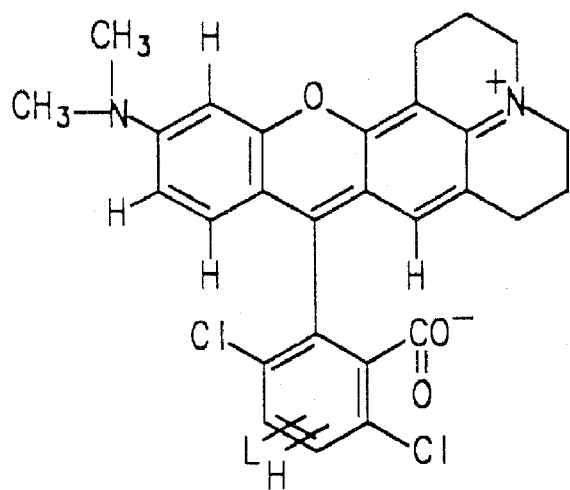
FIG. 3A-C

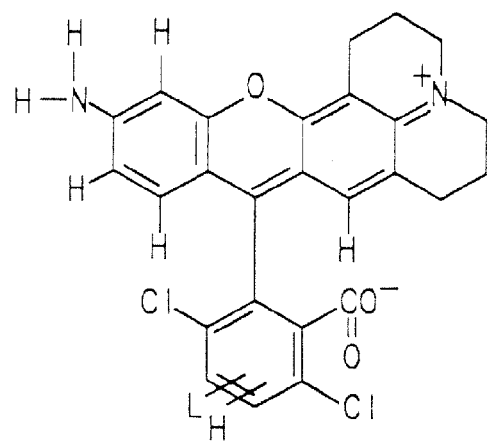
FIG. 3B-D
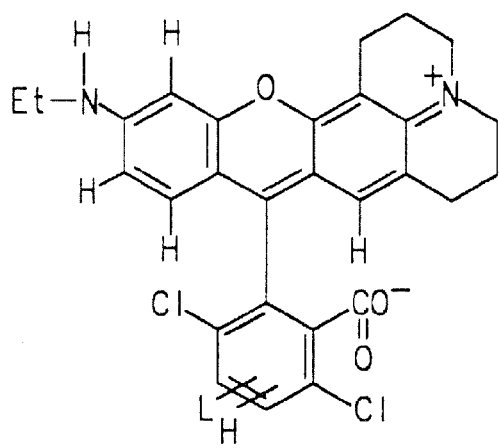
FIG. 3B-E
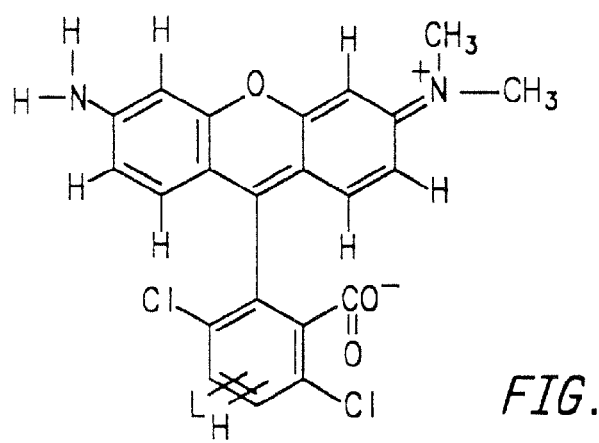
FIG. 3B-F

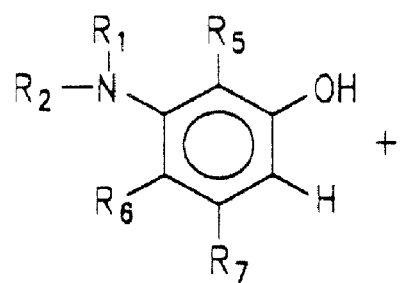
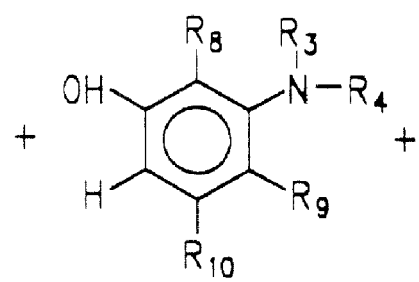
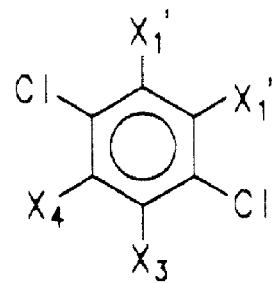
FIG. 4A-A    FIG. 4A-B    FIG. 4A-C
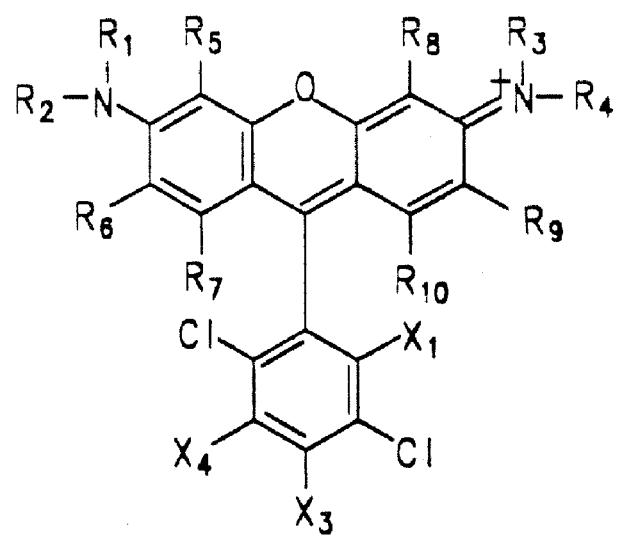
FIG. 4A-D

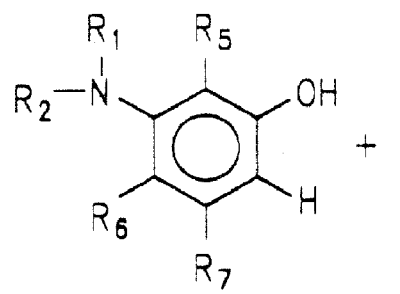
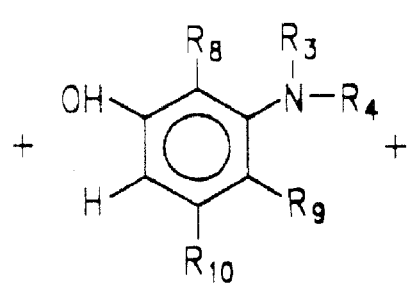
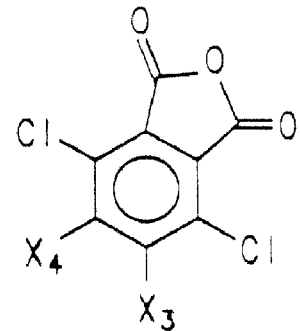
FIG. 4B-A   FIG. 4B-B   FIG. 4B-E
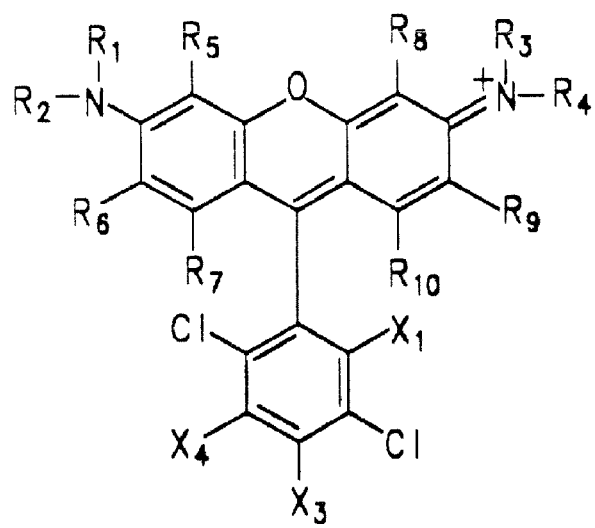
FIG. 4B-D

US 7,399,854 B2

REGENTS LABELED WITH ENERGY TRANSFER DYES

1. CROSS REFERENCE TO RELATED APPLICATIONS

This application is a continuation of U.S. application Ser. No. 10/788,836, filed Feb. 26, 2004 now U.S. Pat. No. 7,169,939, which is a continuation of U.S. application Ser. No. 10/014,743, filed Oct. 29, 2001, now U.S. Pat. No. 6,849,745, which is a continuation of U.S. application Ser. No. 09/272,097, filed Mar. 18, 1999, now U.S. Pat. No. 6,335,440, which is a continuation of U.S. application Ser. No. 09/046,203, filed Mar. 23, 1998, now U.S. Pat. No. 5,945,526, which is a continuation of U.S. application Ser. No. 08/726,462, filed Oct. 4, 1996, now U.S. Pat. No. 5,800,996, which is a continuation-in-part of U.S. application Ser. No. 08/642,330 filed May 3, 1996, now U.S. Pat. No. 5,863,727 and U.S. application Ser. No. 08/672,196, filed Jun. 27, 1996, now U.S. Pat. No. 5,847,162, all of which are incorporated herein by reference.

2. FIELD OF THE INVENTION

The present invention relates to fluorescent dyes and, more specifically, energy transfer fluorescent dyes and their use.

3. DESCRIPTION OF RELATED ART

A variety of fluorescent dyes have been developed for labeling and detecting components in a sample. In general, fluorescent dyes preferably have a high quantum yield and a large extinction coefficient so that the dye may be used to detect small quantities of the component being detected. Fluorescent dyes also preferably have a large Stokes shift (i.e., the difference between the wavelength at which the dye has maximum absorbance and the wavelength at which the dye has maximum emission) so that the fluorescent emission is readily distinguished from the light source used to excite the dye.

One class of fluorescent dyes which has been developed is energy transfer fluorescent dyes. In general, energy transfer fluorescent dyes include a donor fluorophore and an acceptor fluorophore. In these dyes, when the donor and acceptor fluorophores are positioned in proximity with each other and with the proper orientation relative to each other, the energy emission from the donor fluorophore is absorbed by the acceptor fluorophore and causes the acceptor fluorophore to fluoresce. It is therefore important that the excited donor fluorophore be able to efficiently absorb the excitation energy of the donor fluorophore and efficiently transfer the energy to the acceptor fluorophore.

A variety of energy transfer fluorescent dyes have been described in the literature. For example, U.S. Pat. No. 4,996,143 and WO 95/21266 describe energy transfer fluorescent dyes where the donor and acceptor fluorophores are linked by an oligonucleotide chain. Lee et al., *Nucleic Acids Research* 20(10):2471-2483 (1992) describes an energy transfer fluorescent dye which includes 5-carboxy rhodamine linked to 4'-aminomethyl-5-carboxy fluorescein by the 4'-aminomethyl substituent on fluorescein.

Several diagnostic and analytical assays have been developed which involve the detection of multiple components in a sample using fluorescent dyes, e.g. flow cytometry (Lanier et al., *J. Immunol.* 132:151-156 (1984)); chromosome analysis (Gray et al., *Chromosoma* 73:9-27 (1979)); and DNA sequencing. For these assays, it is desirable to simultaneously employ a set of two or more spectrally resolvable fluorescent dyes so that more than one target substance can be detected in the sample at the same time. Simultaneous detection of multiple components in a sample using multiple dyes reduces the time required to serially detect individual components in a sample. In the case of multi-loci DNA probe assays, the use of multiple spectrally resolvable fluorescent dyes reduces the number of reaction tubes that are needed, thereby simplifying the experimental protocols and facilitating the manufacturing of application-specific kits. In the case of automated DNA sequencing, the use of multiple spectrally resolvable fluorescent dyes allows for the analysis of all four bases in a single lane thereby increasing throughput over single-color methods and eliminating uncertainties associated with inter-lane electrophoretic mobility variations. Connell et al., *Biotechniques* 5:342-348 (1987); Prober et al., *Science* 238:336-341 (1987), Smith et al., *Nature* 321:674-679 (1986); and Ansorge et al., *Nucleic Acids Research* 15:4593-4602 (1989).

There are several difficulties associated with obtaining a set of fluorescent dyes for simultaneously detecting multiple target substances in a sample, particularly for analyses requiring an electrophoretic separation and treatment with enzymes, e.g., DNA sequencing. For example, each dye in the set must be spectrally resolvable from the other dyes. It is difficult to find a collection of dyes whose emission spectra are spectrally resolved, since the typical emission band half-width for organic fluorescent dyes is about 40-80 nanometers (nm) and the width of the available spectrum is limited by the excitation light source. As used herein the term "spectral resolution" in reference to a set of dyes means that the fluorescent emission bands of the dyes are sufficiently distinct, i.e., sufficiently non-overlapping, that reagents to which the respective dyes are attached, e.g. polynucleotides, can be distinguished on the basis of the fluorescent signal generated by the respective dyes using standard photodetection systems, e.g. employing a system of band pass filters and photomultiplier tubes, charged-coupled devices and spectrographs, or the like, as exemplified by the systems described in U.S. Pat. Nos. 4,230,558, 4,811,218, or in Wheeless et al., pgs. 21-76, in *Flow Cytometry: Instrumentation and Data Analysis* (Academic Press, New York, 1985).

The fluorescent signal of each of the dyes must also be sufficiently strong so that each component can be detected with sufficient sensitivity. For example, in the case of DNA sequencing, increased sample loading can not compensate for low fluorescence efficiencies, Pringle et al., *DNA Core Facilities Newsletter*, 1:15-21 (1988). The fluorescent signal generated by a dye is generally greatest when the dye is excited at its absorbance maximum. It is therefore preferred that each dye be excited at about its absorbance maximum.

A further difficulty associated with the use of a set of dyes is that the dyes generally do not have the same absorbance maximum. When a set of dyes are used which do not have the same absorbance maximum, a trade off is created between the higher cost associated with providing multiple light sources to excite each dye at its absorbance maximum, and the lower sensitivity arising from each dye not being excited at its absorbance maximum.

In addition to the above difficulties, the charge, molecular size, and conformation of the dyes must not adversely affect the electrophoretic mobilities of the fragments. The fluorescent dyes must also be compatible with the chemistry used to create or manipulate the fragments, e.g., DNA synthesis solvents and reagents, buffers, polymerase enzymes, ligase enzymes, and the like.

Because of the multiple constraints on developing a set of dyes for multicolor applications, particularly in the area of four color DNA sequencing, only a few sets of fluorescent dyes have been developed. Connell et al., *Biotechniques* 5:342-348 (1987); Prober et al., *Science* 238:336-341 (1987); and Smith et al., *Nature* 321:674-679 (1986).

One class of fluorescent dyes that has been found to be useful in multicolor applications are rhodamine dyes, e.g., tetramethylrhodamine (TAMRA), rhodamine X (ROX), rhodamine 6G (R6G), rhodamine 110 (R110), and the like. U.S. Pat. No. 5,366,860. Rhodamine dyes are particularly attractive relative to fluorescein dyes because (1) rhodamines are typically more photostable than fluoresceins, (2) rhodamine-labeled dideoxynucleotides are better substrates for thermostable polymerase enzymes, and (3) the emission spectra of rhodamine dyes is significantly to the red (higher wavelength) of fluoresceins.

One drawback associated with currently available rhodamine dyes, particularly in the context of multiplex detection methods, is the relatively broad emission spectrum of the rhodamine dyes. This broad emission spectrum limits spectral resolution between spectrally neighboring dyes, making the multicomponent analysis of such dye combinations difficult. A second drawback associated with currently available rhodamine dyes is that their absorption spectrum does not match the wavelength of currently available solid state frequency-doubled green diode lasers, e.g., neodymium solid-state YAG lasers, which have an emission line at approximately 532 nm. It is highly advantageous to use such lasers because of their compact size, long useful life, and efficient use of power.

Energy transfer fluorescent dyes possess several features which make them attractive for use in the simultaneous detection of multiple target substances in a sample, such as in DNA sequencing. For example, a single donor fluorophore can be used in a set of energy transfer fluorescent dyes so that each dye has strong absorption at a common wavelength. Then, by varying the acceptor fluorophore in the energy transfer dye, a series of energy transfer dyes having spectrally resolvable fluorescence emissions can be generated.

Energy transfer fluorescent dyes also provide a larger effective Stokes shift than non-energy transfer fluorescent dyes. This is because the Stokes shift for an energy transfer fluorescent dye is based on the difference between the wavelength at which the donor fluorophore maximally absorbs light and the wavelength at which the acceptor fluorophore maximally emits light. In general, a need exists for fluorescent dyes having larger Stokes shifts.

The sensitivity of any assay using a fluorescent dye is dependent on the strength of the fluorescent signal generated by the fluorescent dye. A need therefore exists for fluorescent dyes which have a strong fluorescence signal. With regard to energy transfer fluorescent dyes, the fluorescence signal strength of these dyes is dependent on how efficiently the acceptor fluorophore absorbs the energy emission of the donor fluorophore. This, in turn, depends on a variety of variables, including the proximity of the donor fluorophore to the acceptor fluorophore and the orientation of the donor fluorophore relative to the acceptor fluorophore. A need therefore exists for energy transfer fluorescent dyes in which the orientation between the donor and acceptor fluorophore is such that energy is efficiently transferred between the donor and acceptor fluorophore.

4. SUMMARY OF THE INVENTION

The present invention relates to linkers for linking a donor dye to an acceptor dye in an energy transfer fluorescent dye.

The present invention also relates to energy transfer fluorescent dyes having enhanced fluorescence. The present invention also relates to reagents which include the energy transfer dyes of the present invention, methods for using the dyes and reagents, and kits within which the dyes and reagents are included.

One linker according to the present invention for linking a donor dye to an acceptor dye in an energy transfer fluorescent dye has the general structure $R_{21}Z_1C(O)R_{22}R_{28}$, as illustrated below, where $R_{21}$ is a $C_{1-5}$ alkyl attached to the donor dye, $C(O)$ is a carbonyl group, $Z_1$ is either NH, sulfur or oxygen, $R_{22}$ is a substituent attached to the carbonyl carbon which may be either an alkene, diene, alkyne, a five or six membered ring having at least one unsaturated bond or a fused ring structure, and $R_{28}$ includes a functional group which attaches the linker to the acceptor dye.

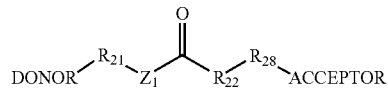

The $R_{28}$ group used in the linker may be any group known in the art which can be used to attach the $R_{22}$ group to an acceptor dye. Typically, the $R_{28}$ group will be attached to a benzene ring or other aromatic ring structure on the acceptor dye. Accordingly, $R_{28}$ is preferably formed by forming an electrophilic functional group on the benzene ring or other aromatic ring structure of the acceptor dye, such as a carboxylic acids, acid halide, sulfonic acid, ester, aldehyde, thio, disulfide, isothiocyanate, isocyanate, sulfonyl halide, maleimide, hydroxysuccinimide ester, haloacetyl, hydroxysulfosuccinimide ester, imido ester, hydrazine, azidonitrophenyl, and azide. The $R_{22}$ group can then be added to the acceptor dye, either before or after attachment of the donor dye to the $R_{22}$ group, by reacting the electrophilic agent on the acceptor dye with a nucleophile, such as an amino, hydroxyl or sulfhydryl nucleophile.

For example, in the embodiment illustrated below, the linker has the general structure $R_{21}Z_1C(O)R_{22}R_{29}Z_2C(O)$ where $R_{21}$ and $R_{22}$ are as detailed above, $Z_1$ and $Z_2$ are each independently either NH, sulfur or oxygen, and $R_{29}$ is a $C_{1-5}$ alkyl, and the terminal carbonyl group is attached to the ring structure of the acceptor dye. In the variation where $Z_2$ is nitrogen, the $C(O)R_{22}R_{29}Z_2$ subunit forms an amino acid subunit.

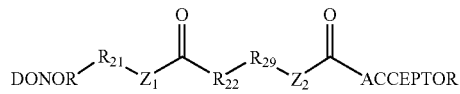

In this embodiment, the linker may be formed by the reaction of an activated carbonyl group (NHS ester) with an amine, hydroxyl or thiol group. It is noted that a wide variety of other mechanisms for attaching an $R_{22}$ group to an acceptor dye are envisaged and are intended to fall within the scope of the invention.

Particular examples of five or six membered rings which may be used as $R_{22}$ in the linker include, but are not limited to cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine and oxazine. Examples of fused ring structures include, but are not limited to indene, benzofuran, thionaphthene, indole and naphthalene.

A preferred embodiment of this linker is where $R_{21}$ and $R_{29}$ are methylene, $Z_1$ and $Z_2$ are NH, and $R_{22}$ is benzene, as shown below.

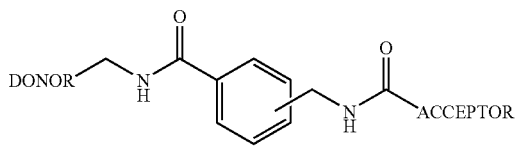

One class of energy transfer fluorescent dyes according to the present invention includes a donor dye which has the following xanthene ring structure with a 4' ring position:

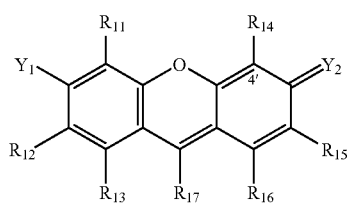

where $Y_1$ and $Y_2$ taken separately are either hydroxyl, oxygen, iminium or amine, the iminium and amine preferably being a tertiary iminium or amine. $R_{11}$-$R_{17}$ may be any substituent which is compatible with the energy transfer dyes of the present invention, it being noted that the $R_{11}$-$R_{17}$ may be widely varied in order to alter the spectral and mobility properties of the dyes.

According to this embodiment, the energy transfer dye also includes an acceptor dye which absorbs the excitation energy emitted by the donor dye and fluoresces at a second wavelength in response. The energy transfer dye also includes a linker which attaches the donor dye to the acceptor dye.

In one variation of this embodiment of energy transfer dyes, the linker has the general structure $R_{21}Z_1C(O)R_{22}R_{28}$, as illustrated above, where $R_{21}$ is a $C_{1-5}$ alkyl attached to the 4' position of the xanthene donor dye, C(O) is a carbonyl group, $Z_1$ is either NH, sulfur or oxygen, $R_{22}$ is a substituent attached to the carbonyl carbon which may be either an alkene, diene, alkyne, a five or six membered ring having at least one unsaturated bond or a fused ring structure, and $R_{28}$ includes a functional group which attaches the linker to the acceptor dye.

In a further variation of this embodiment of energy transfer dyes, the linker has the general structure $R_{21}Z_1C(O)R_{22}R_{29}Z_2C(O)$, as illustrated above, where $R_{21}$ and $R_{22}$ are as detailed above, $Z_1$ and $Z_2$ are each independently either NH, sulfur or oxygen, and $R_{29}$ is a $C_{1-5}$ alkyl, and the terminal carbonyl group is attached to the ring structure of the acceptor dye. In the variation where $Z_2$ is nitrogen, —C(O)$R_{22}R_{29}Z_2$— forms an amino acid subunit.

In a further preferred variation of this embodiment of energy transfer dyes, the linker is where $R_{21}$ and $R_{29}$ are methylene, $Z_1$ and $Z_2$ are NH, and $R_{22}$ is benzene, as shown below.

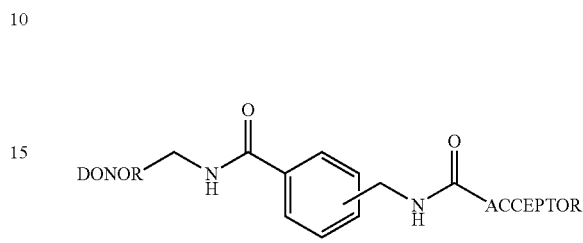

The donor dye may optionally be a member of the class of dyes where $R_{17}$ is a phenyl or substituted phenyl. When $Y_1$ is hydroxyl and $Y_2$ is oxygen, and $R_{17}$ is a phenyl or substituted phenyl, the dye is a member of the fluorescein class of dyes. When $Y_1$ is amine and $Y_2$ is iminium, and $R_{17}$ is a phenyl or substituted phenyl, the dye is a member of the rhodamine class of dyes. Further according to this embodiment, the acceptor dye may optionally be a member of the xanthene, cyanine, phthalocyanine and squaraine classes of dyes.

In another embodiment, the energy transfer fluorescent dyes have donor and acceptor dyes with the general structure

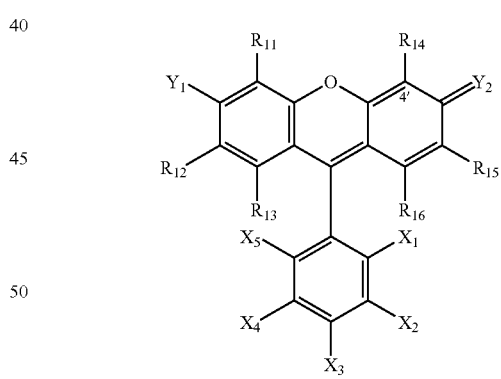

where $Y_1$ and $Y_2$ taken separately are either hydroxyl, oxygen, iminium or amine, the iminium and amine preferably being a tertiary iminium or amine and $R_{11}$-$R_{16}$ are any substituents which are compatible with the energy transfer dyes of the present invention.

According to this embodiment, as illustrated below, the linker is attached to one of $X_3$ and $X_4$ substituents of each of the donor and acceptor dyes, preferably the $X_3$ substituents of the donor and acceptor dyes. In this embodiment, the linker is preferably short and/or rigid as this has been found to enhance the transfer of energy between the donor and acceptor dyes.

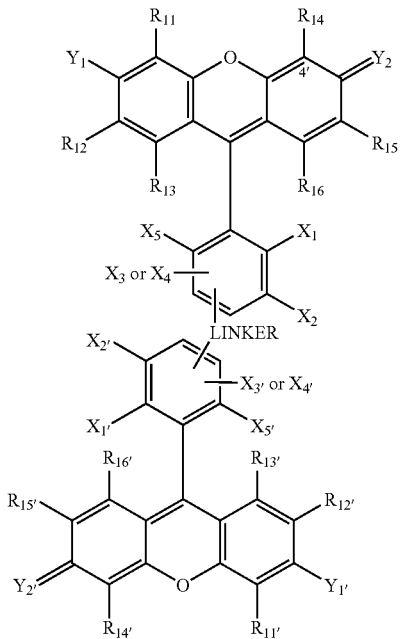

In another embodiment, the energy transfer fluorescent dyes include a donor dye which is a member of the xanthene class of dyes, an acceptor dye which is a member of the xanthene, cyanine, phthalocyanine and squaraine classes of dyes which is capable of absorbing the excitation energy emitted by the donor dye and fluorescing at a second wavelength in response, and a linker attaching the donor dye to the acceptor dye. According to this embodiment, the acceptor has an emission maximum that is greater than about 600 nm or at least about 100 nm greater than the absorbance maximum of the donor dye.

In addition to the above-described novel energy transfer fluorescent dyes, the present invention also relates to fluorescent reagents containing the energy transfer fluorescent dyes. In general, these reagents include any molecule or material to which the energy transfer dyes of the invention can be attached and used to detect the presence of the reagent based on the fluorescence of the energy transfer dye. In one embodiment, a fluorescent reagent is provided which includes a nucleoside or a mono-, di- or triphosphate nucletotide labeled with an energy transfer fluorescent dye. The nucleotide may be a deoxynucleotide which may be used for example, in the preparation of dye labeled oligonucleotides. The nucleotide may also be a dideoxynucleoside which may be used, for example, in dye terminator sequencing. In another embodiment, the fluorescent reagent includes an oligonucleotide labeled with an energy transfer fluorescent dye. These reagents may be used, for example, in dye primer sequencing.

The present invention also relates to methods which use the energy transfer fluorescent dyes and reagents of the present invention. In one embodiment, the method includes forming a series of different sized oligonucleotides labeled with an energy transfer fluorescent dye of the present invention, separating the series of labeled oligonucleotides based on size, detecting the separated labeled oligonucleotides based on the fluorescence of the energy transfer dye.

In one embodiment of this method, a mixture of extended labeled primers is formed by hybridizing a nucleic acid sequence with an oligonucleotide primer in the presence of deoxynucleotide triphosphates, and at least one dye labeled dideoxynucleotide triphosphate and a DNA polymerase. The DNA polymerase serves to extend the primer with the deoxynucleotide triphosphates until a dideoxynucleotide triphosphate is incorporated which terminates extension of the primer. Once terminated, the mixture of extended primers are separated and detected based on the fluorescence of the dye on the dideoxynucleoside. In a variation of this embodiment, four different fluorescently labeled dideoxynucleotide triphosphates are used, i.e., a fluorescently labeled dideoxycytosine triphosphate, a fluorescently labeled dideoxyadenosine triphosphate, a fluorescently labeled dideoxyguanosine triphosphate, and a fluorescently labeled dideoxythymidine triphosphate. In an alternate embodiment of this method, the oligonucleotide primer is fluorescently labeled as opposed to the deoxynucleotide triphosphate.

The present invention also relates to kits containing the dyes and reagents for performing DNA sequencing using the dyes and reagents of present invention.

5. BRIEF DESCRIPTION OF THE FIGURES

FIG. 1 illustrates the modification of a carboxy substituent on a energy transfer dye to an activated N-hydroxysuccinimidyl (NHS) ester which is then reacted with an aminohexyl-oligomer to form a dye labeled oligonucleotide primer.

FIG. 2 compares the fluorescence emission strength of a series of energy transfer dyes of the present invention to other energy transfer dyes and the acceptor dye alone.

FIGS. 3A and 3B show several particularly preferred embodiments of 4,7-dichlororhodamine dye compounds which can be used in the energy transfer dyes of the present invention.

FIGS. 4A and 4B show preferred generalized synthesis schemes for the preparation of the 4,7-dichlororhodamine dyes of the invention.

FIG. 4A shows a generalized synthesis wherein the substituent $X_1$ can be other than carboxylate.

FIG. 4B shows a generalized synthesis wherein the substituent $X_1$ is carboxylate.

FIGS. 9A-D compare the fluorescence emission strength of a series of energy transfer dyes of the present invention to the corresponding acceptor dye alone.

Figure 9A:
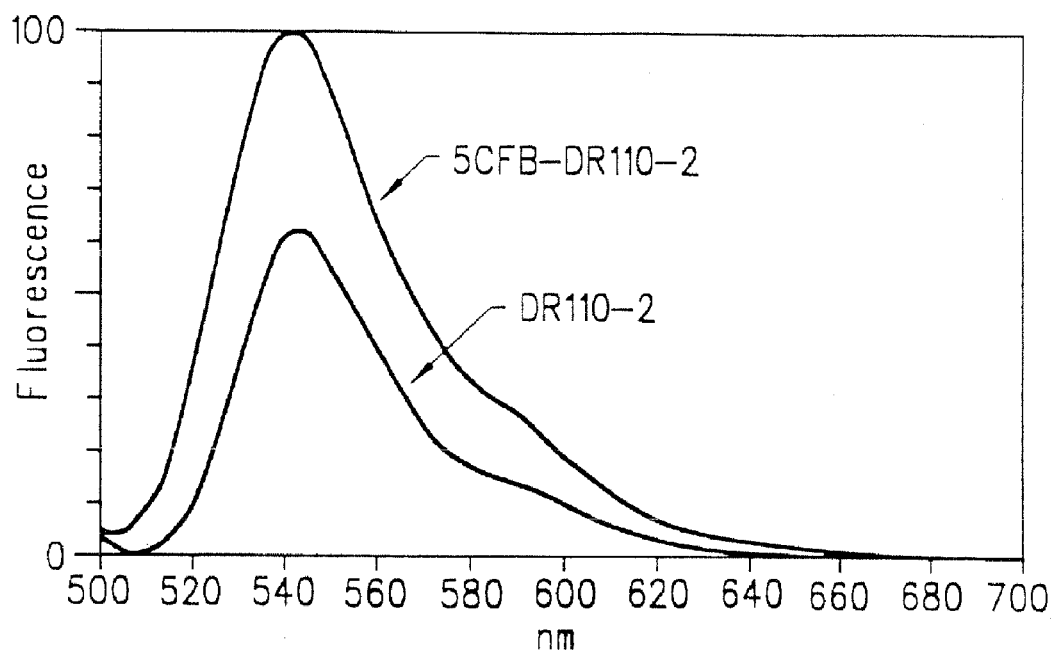

FIG. 9A provides the overlaid spectra of 6-CFB-DR110-2 and DR110-2.

Figure 9B:
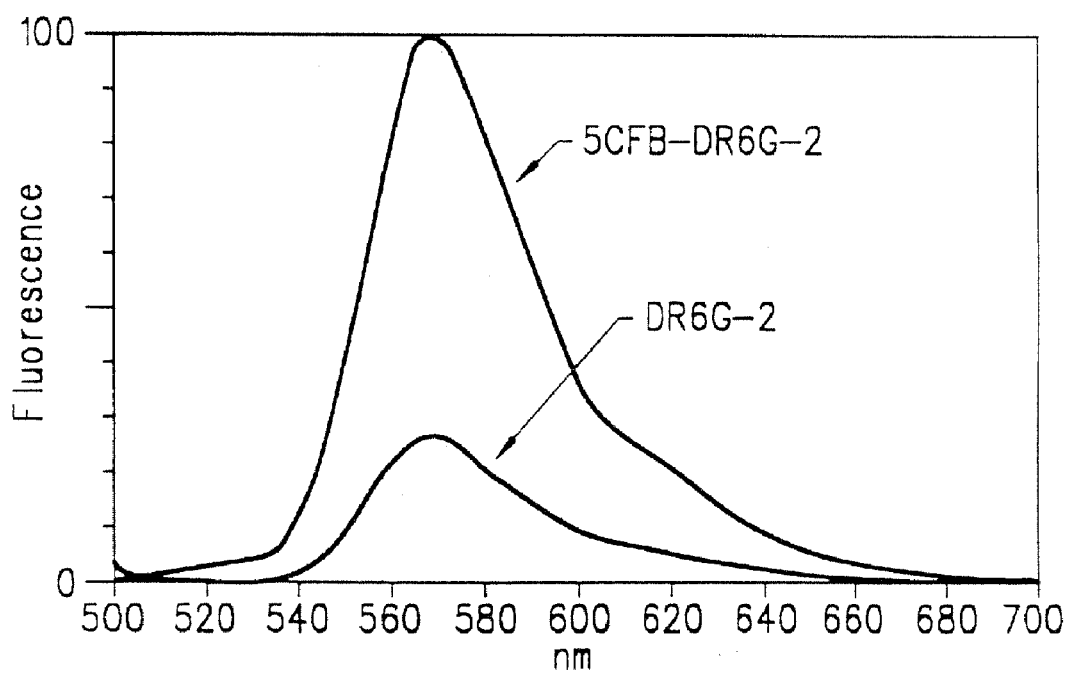

FIG. 9B provides an overlaid spectra of 5-CFB-DR6G-2 and DR6G-2.

Figure 9C:
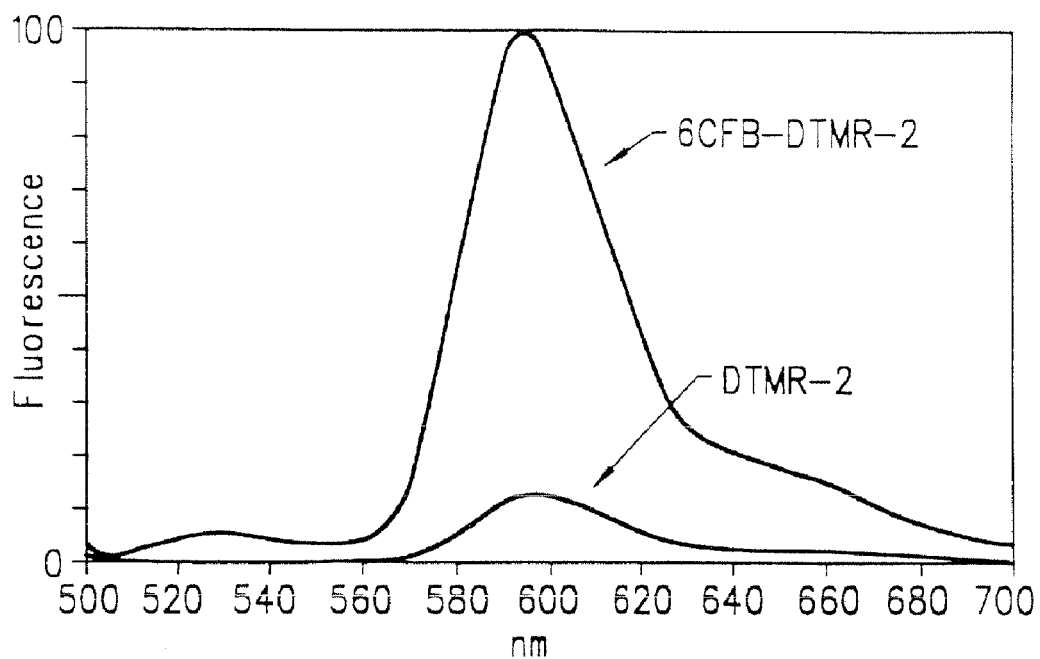

FIG. 9C provides an overlaid spectra of 6-CFB-DTMR-2 and DTMR-2.

Figure 9D:
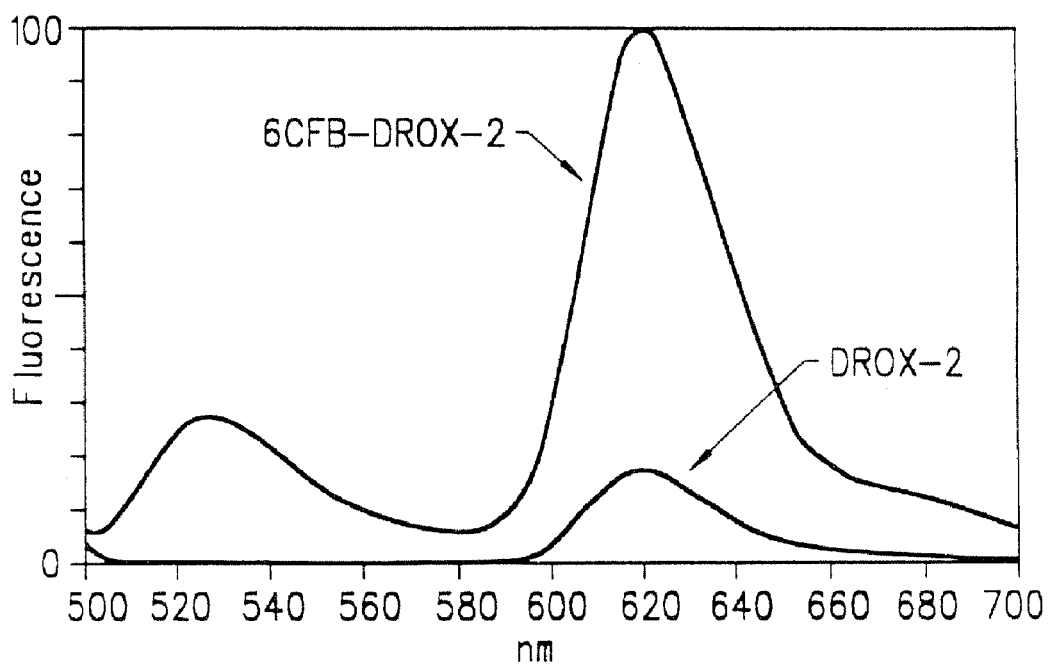

FIG. 9D provides an overlaid spectra of 6-CFB-DROX-2 and DROX-2.

Figure 10:
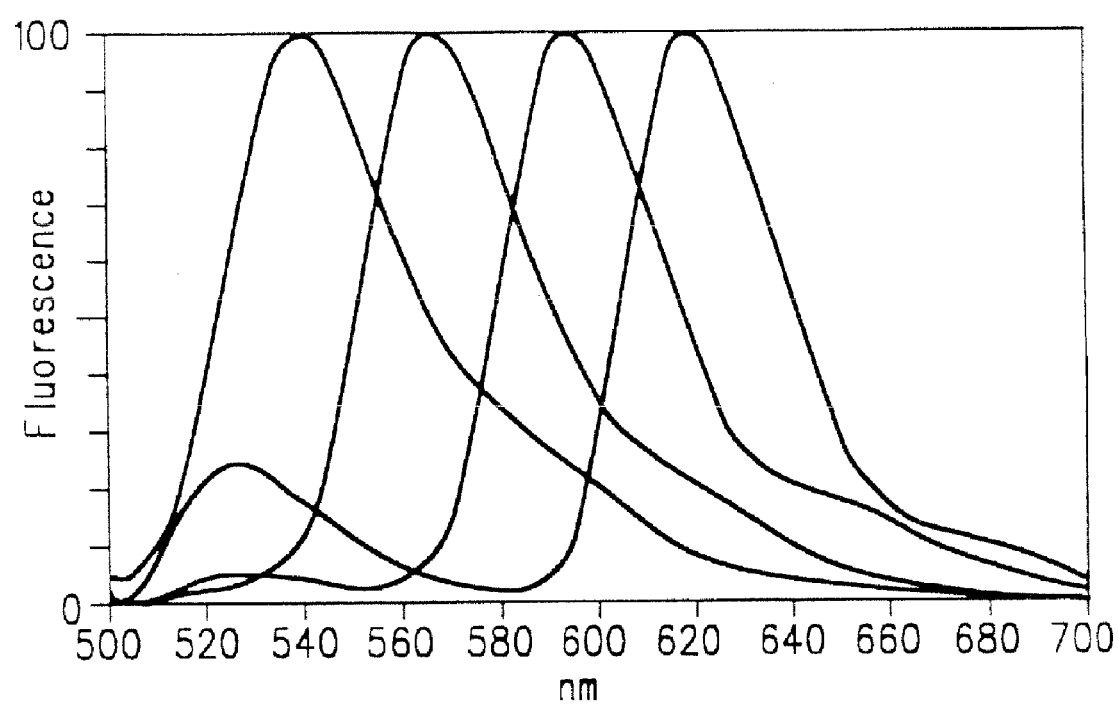

FIG. 10 illustrates a set of four dyes (5-CFB-DR110-2,5-CFB-DR6G-2,6-CFB-DTMR-2, and 6-CFB-DROX-2) which are spectrally resolvable from each other.

Figure 11:
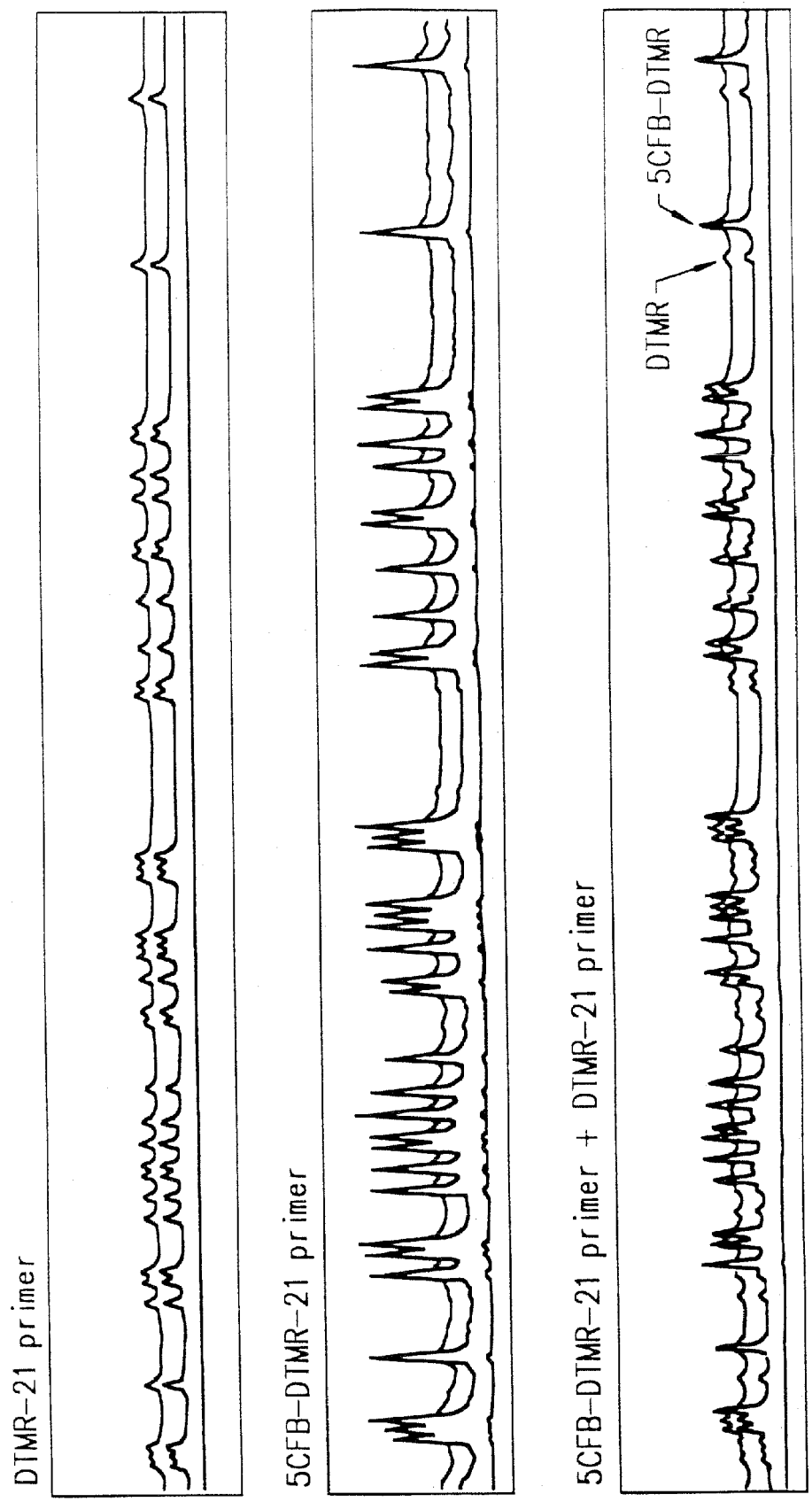

FIG. 11 is a plot of a mixture of labeled oligonucleotides generated during dye primer sequencing using 6-CFB-DTMR-2 and DTMR-2 labeled primers.

Figure 12:
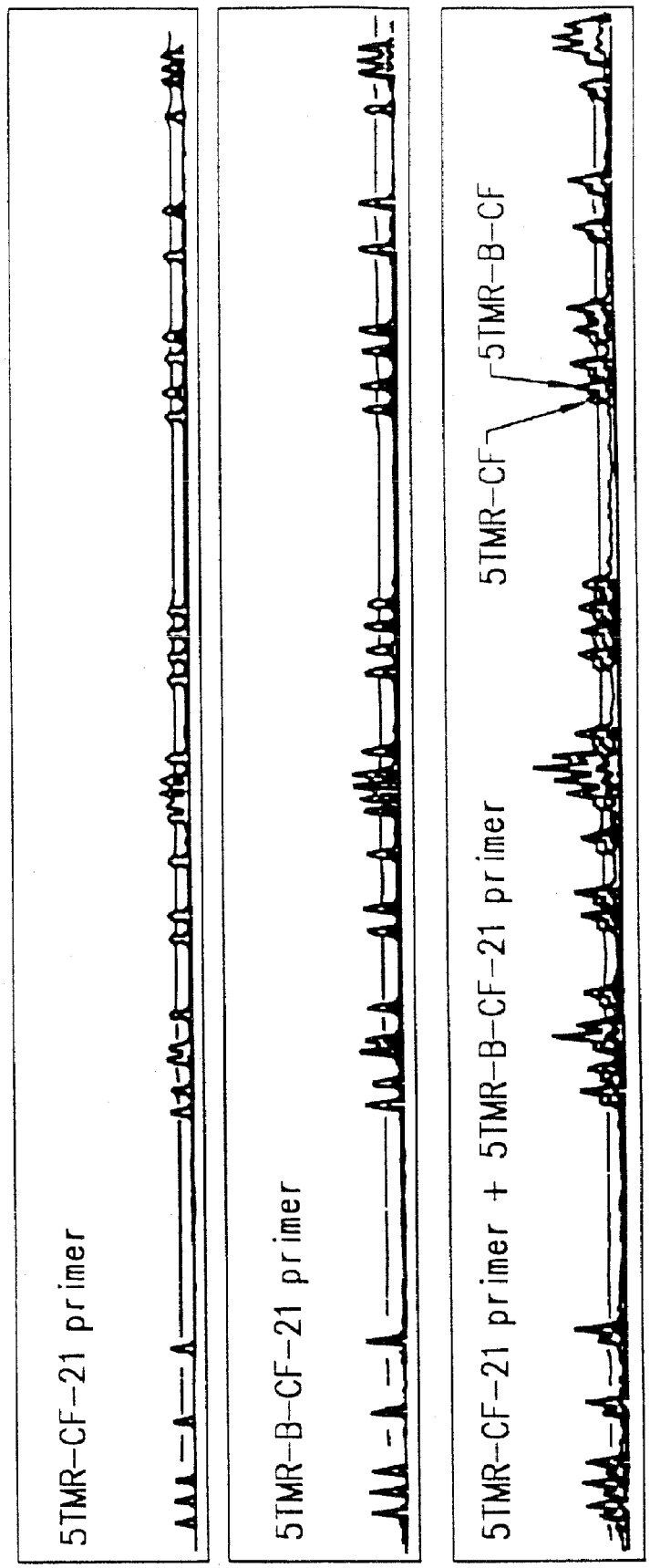

FIG. 12 is a plot of a mixture of labeled oligonucleotides generated during dye primer sequencing using 5-CF-TMR-2 and 5-CF-B-TMR-2 labeled primers.

Figure 13:
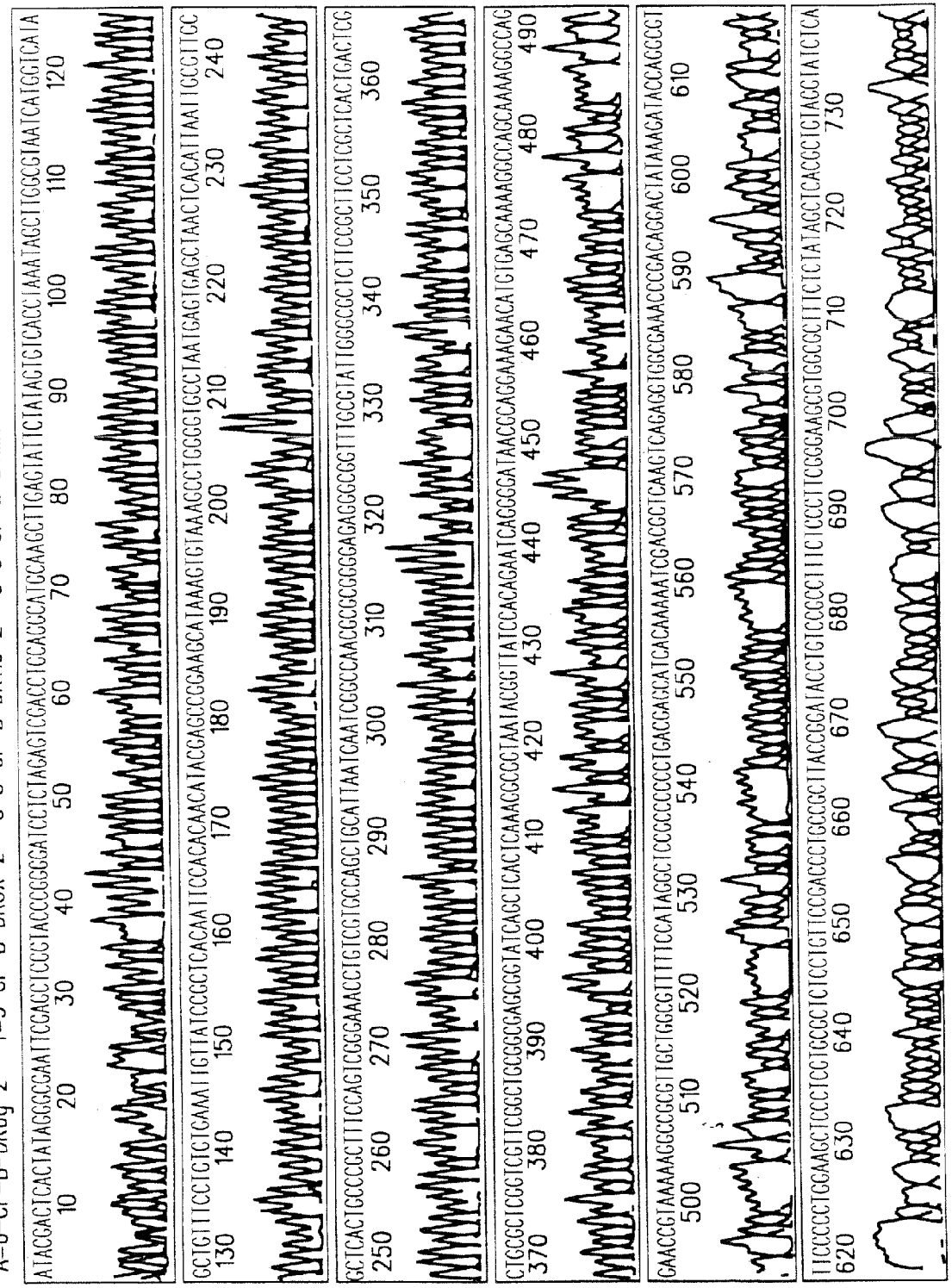

FIG. 13 is a four color plot of dye primer sequencing using a four dye set including 5-CFB-DR110-2,6-CFB-DR6g-2, 5-CFB-DTMR-2, and 5-CFB-DROX-2.

6. DETAILED DESCRIPTION

6.1 Energy Transfer Dye Linkers of the Present Invention

The present invention relates to novel linkers for linking a donor dye to an acceptor dye in an energy transfer fluorescent dye. The present invention also relates to energy transfer fluorescent dyes which incorporate these linkers. These linkers have been found to faciliate the efficient transfer of energy between a donor and acceptor dye in an energy transfer dye.

One linker according to the present invention for linking a donor dye to an acceptor dye in an energy transfer fluorescent dye has the general structure $R_{21}Z_1C(O)R_{22}R_{28}$, as illustrated below, where $R_{21}$ is a $C_{1-5}$ alkyl attached to the donor dye, $C(O)$ is a carbonyl group, $Z_1$ is either NH, sulfur or oxygen, $R_{22}$ is a substituent which includes an alkene, diene, alkyne, a five and six membered ring having at least one unsaturated bond or a fused ring structure which is attached to the carbonyl carbon, and $R_{28}$ includes a functional group which attaches the linker to the acceptor dye.

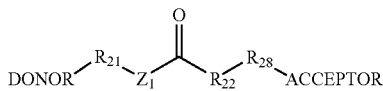

In one embodiment of this linker, illustrated below, the linker has the general structure $R_{21}Z_1C(O)R_{22}R_{29}Z_2C(O)$ where $R_{21}$ and $R_{22}$ are as detailed above, $Z_1$ and $Z_2$ are each independently either NH, sulfur or oxygen, $R_{29}$ is a $C_{1-5}$ alkyl, and the terminal carbonyl group is attached to the ring structure of the acceptor dye. In the variation where $Z_2$ is nitrogen, the $C(O)R_{22}R_{29}Z_2$ subunit forms an amino acid subunit.

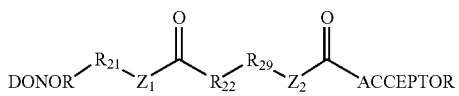

Particular examples of five or six membered rings which may be used as $R_{22}$ in the linker include, but are not limited to cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine and oxazine. Examples of fused ring structures include, but are not limited to indene, benzofuran, thionaphthene, indole and naphthalene.

A preferred embodiment of this linker is where $R_{21}$ and $R_{29}$ are methylene, $Z_1$ and $Z_2$ are NH, and $R_{22}$ is benzene, as shown below.

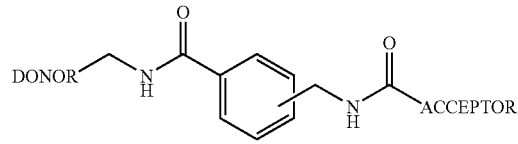

Table 3 illustrates examples of —$C(O)R_{22}$— subunits of linkers which may be used in the linkers of the present invention.

6.2 Energy Transfer Dyes of the Present Invention

In general, the energy transfer dyes of the present invention include a donor dye which absorbs light at a first wavelength and emits excitation energy in response, an acceptor dye which is capable of absorbing the excitation energy emitted by the donor dye and fluorescing at a second wavelength in response, and a linker which attaches the donor dye to the acceptor dye. With regard to all of the molecular structures provided herein, it is intended that these molecular structures encompass not only the exact electronic structure presented, but also include all resonant structures and protonation states thereof.

One class of energy transfer fluorescent dyes according to the present invention includes a donor dye which is a member of the xanthene class of dyes, an acceptor dye and a linker which is a member of the group of linkers described in Section 6.1 As used herein, xanthene dyes include all molecules having the general structure:

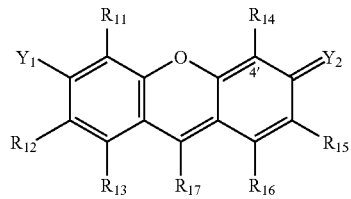

where $Y_1$ and $Y_2$ taken separately are either hydroxyl, oxygen, iminium or amine, the iminium and amine preferably being a tertiary iminium or amine. When $Y_1$ is hydroxyl and $Y_2$ is oxygen, and $R_{17}$ is a phenyl or substituted phenyl, the dye is a member of the fluorescein class of dyes. When $Y_1$ is amine and $Y_2$ is iminium, and $R_{17}$ is a phenyl or substituted phenyl, the dye is a member of the rhodamine class of dyes.

$R_{11}$-$R_{17}$ may be any substituent which is compatible with the energy transfer dyes of the present invention, it being noted that the $R_{11}$-$R_{17}$ may be widely varied in order to alter the spectral and mobility properties of the dyes. The number indicated in the ring structure indicates the 4' position on the xanthene ring structure. For the energy transfer dyes of the present invention in which the linker is attached to the 4' position of the xanthene ring structure, the $R_{14}$ substituent corresponds to the linker.

Examples of $R_{11}$-$R_{17}$ substituents include, but not limited to hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof.

In one embodiment, $R_{15}$ and $R_{16}$ are taken together to form a substituted or unsubstituted benzene ring. This class of xanthene dyes are referred to herein as asymmetric benzoxanthene dyes and are described in U.S. application Ser. No. 08/626,085, filed Apr. 1, 1996, now U.S. Pat. No. 6,020,481, entitled Asymmetric Benzoxanthene Dyes, by Scott C. Benson et al. which is incorporated herein by reference.

In another embodiment, $R_{17}$ is a phenyl or substituted phenyl having the general formula

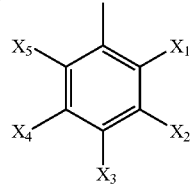

Substituents $X_1$-$X_5$ on the phenyl ring can include hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof.

In one embodiment, the donor dye is a member of the class of dyes where $Y_1$ is amine, $Y_2$ is iminium, and $X_2$ and $X_5$ are chlorine, referred to herein as 4,7-dichlororhodamine dyes. Dyes falling within the 4,7-dichlororhodamine class of dyes and their synthesis are described herein as well as in U.S. application Ser. No. 08/672,196, filed Jun. 27, 1996, now U.S. Pat. No. 5,847,162, entitled "4,7-DICHLOROR-HODAMINE DYES," which is incorporated herein by reference.

As used here, alkyl denotes straight-chain and branched hydrocarbon moieties, i.e., methyl, ethyl, propyl, isopropyl, tert-butyl, isobutyl, sec-butyl, neopentyl, tert-pentyl, and the like. Substituted alkyl denotes an alkyl moiety substituted with any one of a variety of substituents, including, but not limited to hydroxy, amino, thio, cyano, nitro, sulfo, and the like. Haloalkyl denotes a substituted alkyl with one or more halogen atom substituents, usually fluoro, chloro, bromo, or iodo. Alkene denotes a hydrocarbon wherein one or more of the carbon-carbon bonds are double bonds, and the non-double bonded carbons are alkyl or substituted alkyl. Alkyne denotes a hydrocarbon where one or more of the carbons are bonded with a triple bond and where the non-triple bonded carbons are alkyl or substituted alkyl moieties. Sulfonate refers to moieties including a sulfur atom bonded to 3 oxygen atoms, including mono- and di-salts thereof, e.g., sodium sulfonate, potassium sulfonate, disodium sulfonate, and the like. Amino refers to moieties including a nitrogen atom bonded to 2 hydrogen atoms, alkyl moieties, or any combination thereof. Amido refers to moieties including a carbon atom double bonded to an oxygen atom and single bonded to an amino moiety. Nitrile refers to moieties including a carbon atom triple bonded to a nitrogen atom. Alkoxy refers to a moiety including an alkyl moiety single bonded to an oxygen atom. Aryl refers to single or multiple phenyl or substituted phenyl, e.g., benzene, naphthalene, anthracene, biphenyl, and the like.

Figure 1:
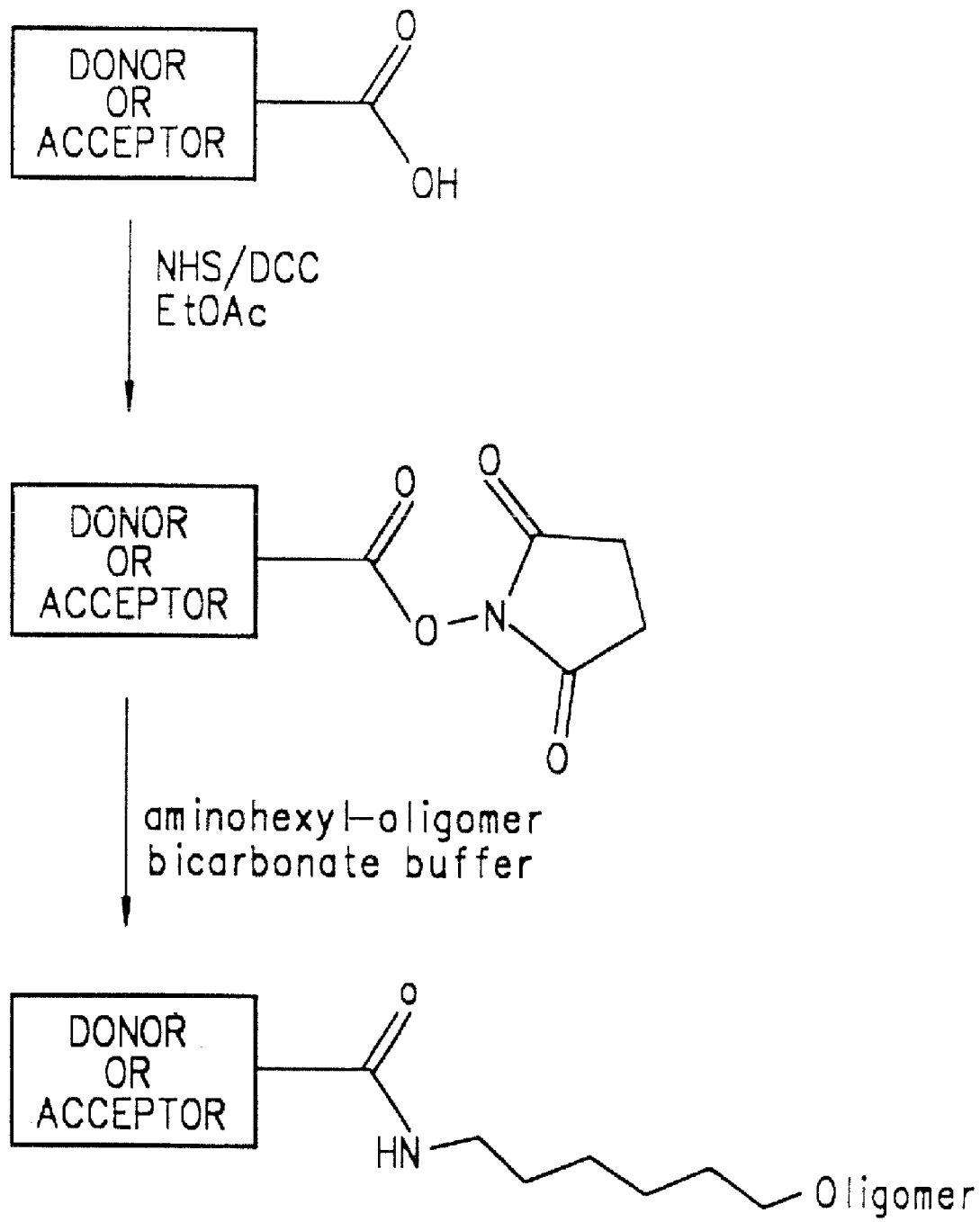

$R_{11}$-$R_{17}$ may also each independently be a linking moiety which may be used to attach the energy transfer dye to a reagent, such as a nucleotide, nucleoside or oligonucleotide. Examples of linking moieties include isothiocyanate, sulfonyl chloride, 4,6-dichlorotriazinylamine, succinimidyl ester, or other active carboxylate whenever the complementary functionality is amine. Preferably the linking group is maleimide, halo acetyl, or iodoacetamide whenever the complementary functionality is sulfhydryl. See R. Haugland, *Molecular Probes Handbook of Fluorescent Probes and Research Chemicals*, Molecular Probes, Inc. (1992). In a particularly preferred embodiment, as illustrated in FIG. 1, the linking group is an activated NHS ester formed from a carboxyl group on either the donor or acceptor dye which can be reacted with an aminohexyl-oligomer to form a dye labeled oligonucleotide primer.

The energy transfer fluorescent dyes of this embodiment also include an acceptor dye which is capable of absorbing the excitation energy emitted by the donor dye and fluorescing at a second wavelength in response, and a linker which attaches the donor dye to the acceptor dye. In the first class of energy transfer dyes, the linker is a member of the class of linkers described in Section I and is attached to the donor dye at the 4' position of the xanthene ring structure.

Energy transfer dyes of this first class exhibit enhanced fluorescent strength as compared to the acceptor fluorophore itself and energy transfer fluorescent dyes having the same donor-acceptor pair where the linkage between the donor-acceptor pair is different.

The present invention also relates to a second class of energy transfer fluorescent dyes in which the donor and acceptor dyes each have the general structure

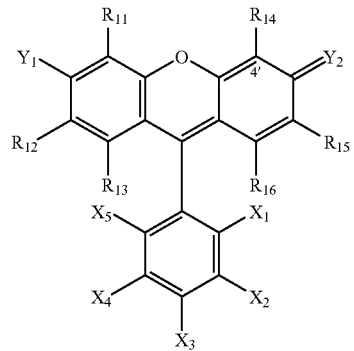

where $Y_1$, $Y_2$, $R_{11}$-$R_{16}$ and $X_1$-$X_5$ are as specified above.

Within this class of dyes, the linker is attached to the donor and acceptor dyes by one of $X_3$ and $X_4$ substituents of each of the donor and acceptor dyes.

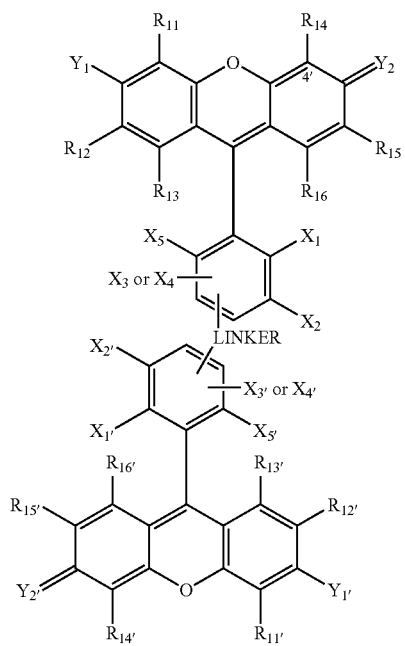

In a preferred embodiment of this class of dyes, the linker is attached to the donor and acceptor dyes by the $X_3$ substituent of each of the donor and acceptor dyes.

Within this class of dyes, the linker is preferably short and/or rigid as this has been found to enhance the transfer of energy between the donor and acceptor dyes.

The present invention also relates to a third class of energy transfer fluorescent dyes in which the acceptor dye is a member of the 4,7-dichlororhodamine class of dyes, i.e., dyes having the general structure

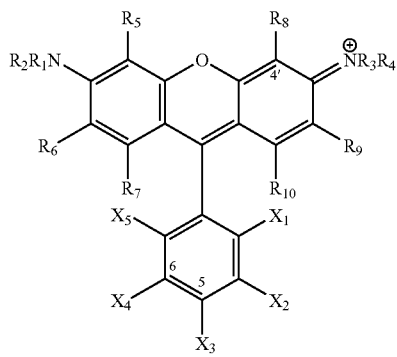

where:

$R_1$-$R_4$ are each independently hydrogen, alkyl or where $R_1$ and $R_5$, $R_2$ and $R_6$, $R_3$ and $R_8$, $R_4$ and $R_9$ are taken together to form a ring, and combinations thereof, $R_5$-$R_{10}$ are each independently hydrogen, fluorine, chlorine, bromine, iodine, carboxyl, alkyl, alkene, alkyne, sulfonate, sulfone, amino, ammonium, amido, nitrile, alkoxy, phenyl, or substituted phenyl, or where adjacent substituents are taken together to form a ring, and combinations thereof;

$X_1$, $X_3$ and $X_4$ are each independently hydrogen, fluorine, chlorine, bromine, iodine, carboxyl, alkyl, alkene, alkyne, sulfonate, sulfone, amino, ammonium, amido, nitrile, or alkoxy, or where adjacent substituents are taken together to form a ring, and combinations thereof; and $X_2$ and $X_5$ are chlorine.

With regard to $R_1$-$R_{10}$, $X_3$ and $X_4$, $R_1$ and $R_5$, $R_2$ and $R_6$, $R_3$ and $R_8$, $R_4$ and $R_9$, and $X_3$ and $X_4$ may each independently be taken together to form a 5, 6, or 7 membered ring.

The numbers (4', 5, 6) indicated in the ring structure indicate the 4'-, 5- and 6-ring positions on the rhodamine ring structure. As will be discussed herein, the 4'- and 5-positions are preferred sites for attachment of the linker used in the energy transfer dyes of the present invention which attaches the donor to the acceptor fluorophore. The 4'-, 5- and 6-ring positions are also preferred sites for attachment of a biomolecule, such as a nucleotide or oligonucleotide to the energy transfer dye.

Donor dyes within this class of energy transfer dyes may include any dye which emits excitation energy which a 4,7-dichlororhodamine dye is capable of absorbing and producing an energy emission in response. In one embodiment, the donor dye has a xanthene ring structure with a 4' ring position where the 4,7-dichlororhodamine acceptor dye is attached to the donor dye by a linker which is attached to the 4' ring position of the xanthene dye. The linker is preferably attached to the 5 or 6 ring positions of the 4,7-dichlororhodamine acceptor dye.

Energy transfer dyes according to this third class of dyes, i.e., where 4,7-dichlororhodamine is the acceptor dye, provide the advantage of having a relatively narrow emission spectrum as compared to other rhodamine dyes. This narrow emission spectrum enhances the spectral resolution achievable by a set of these dyes, thereby facilitating multicomponent analysis using these dyes.

The present invention also relates to a fourth class of energy transfer fluorescent dyes in which the donor dye is a member of the xanthene class of dyes, the acceptor dye is a member of the xanthene, cyanine, phthalocyanine and squaraine classes of dyes, and the acceptor has an emission maximum that is greater than about 600 nm and/or preferably has an emission maximum that is at least about 100 nm greater than the absorbance maximum of the donor dye. Within this class of dyes, the donor is preferably a member of the fluorescein class of dyes.

The fourth class of energy transfer dyes of the present invention exhibit unusually large Stoke shifts, as measured by the difference between the absorbance of the donor and the emission of the acceptor. In addition, these dyes exhibit efficient energy transfer in that minimal donor fluorescence is observed.

Described herein in greater detail are the four classes of energy transfer dyes of the present invention.

TABLE 1

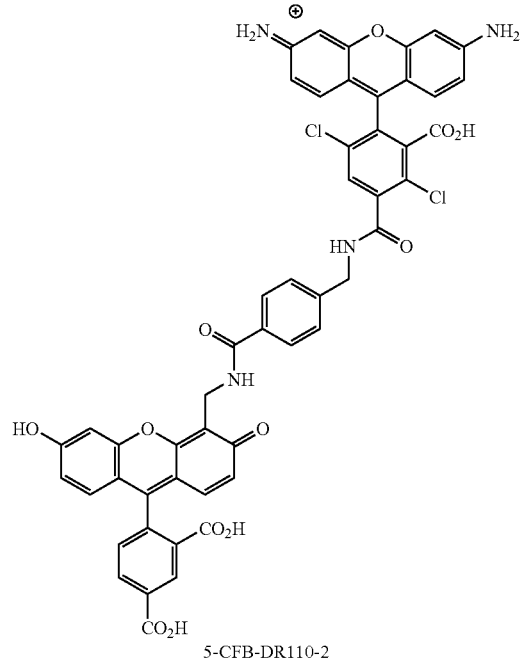

5-CFB-DR110-2

TABLE 1-continued
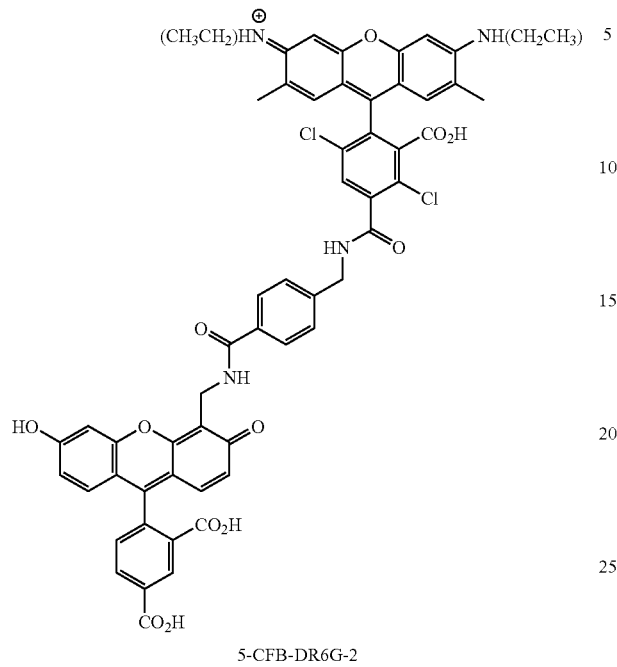
5-CFB-DR6G-2
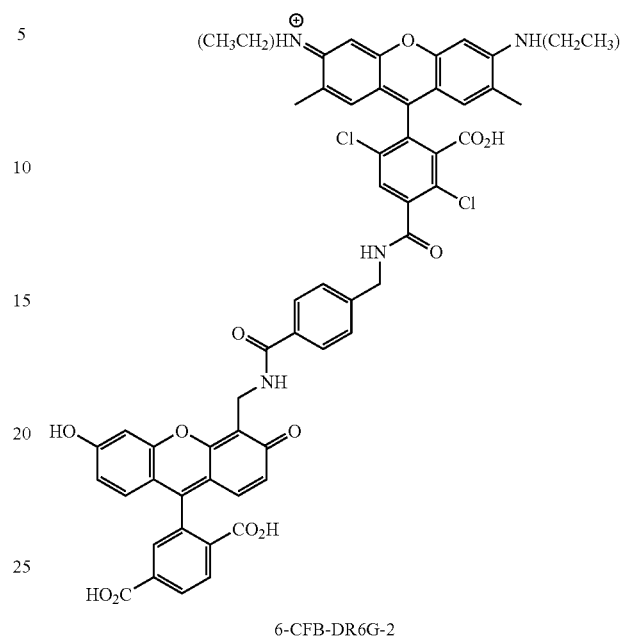
6-CFB-DR6G-2
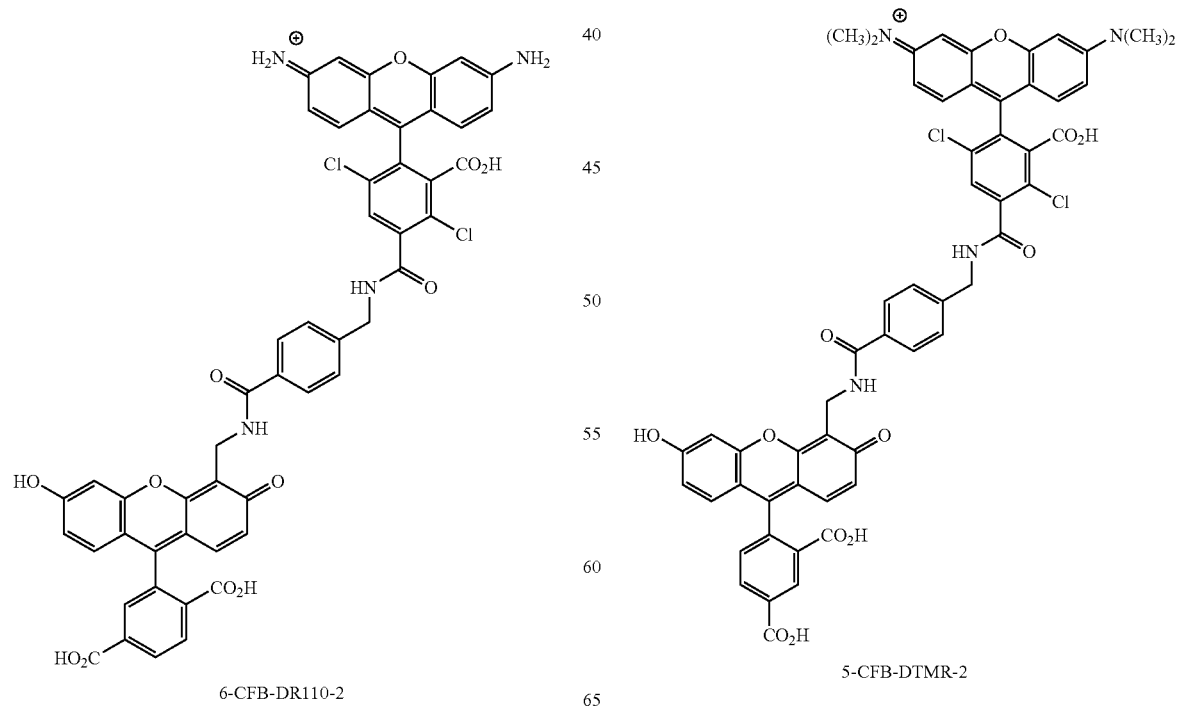
6-CFB-DR110-2
5-CFB-DTMR-2

TABLE 1-continued
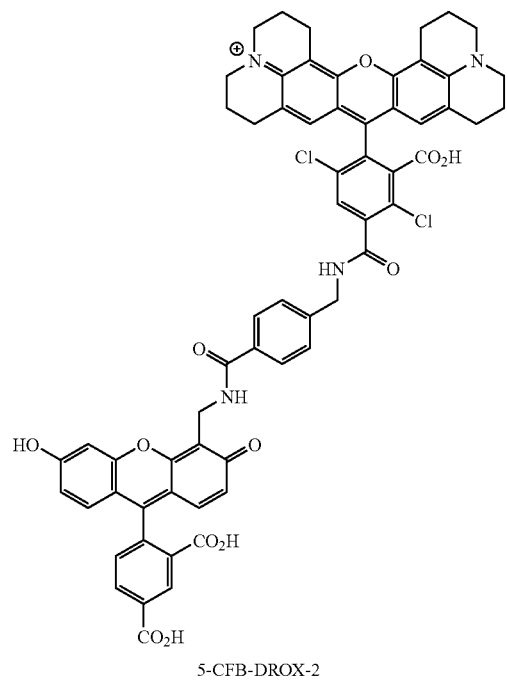
5-CFB-DROX-2
TABLE 1-continued
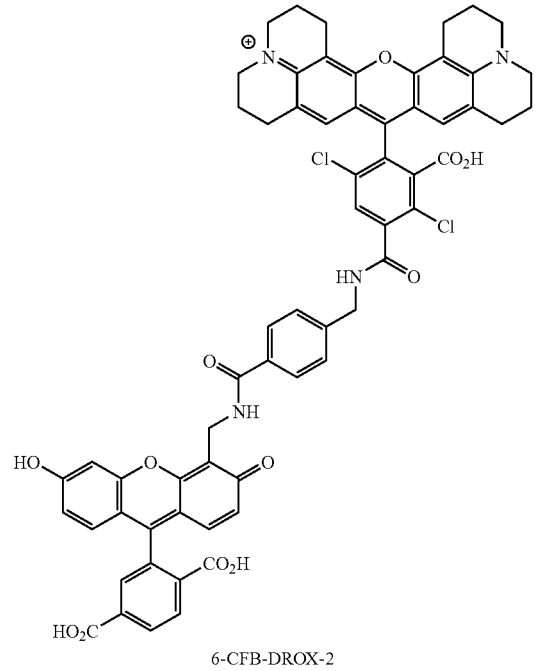
6-CFB-DROX-2
TABLE 1A
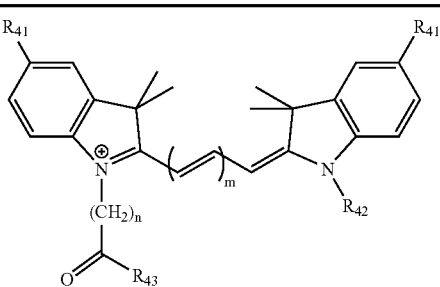
CYANINE
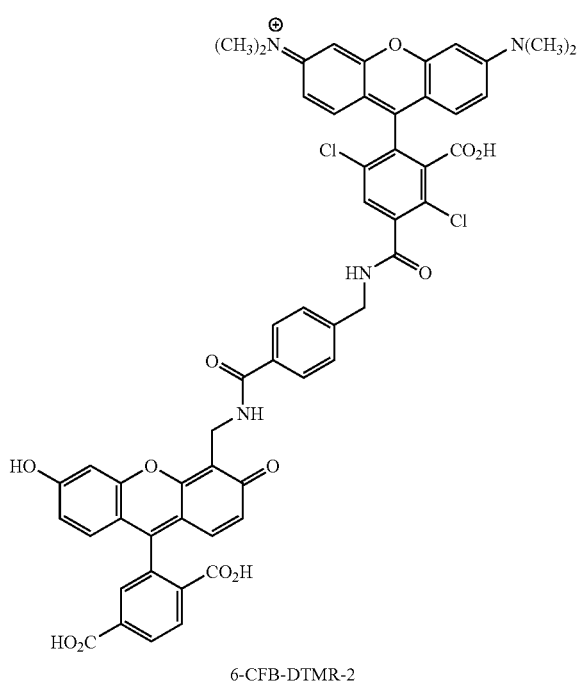
6-CFB-DTMR-2
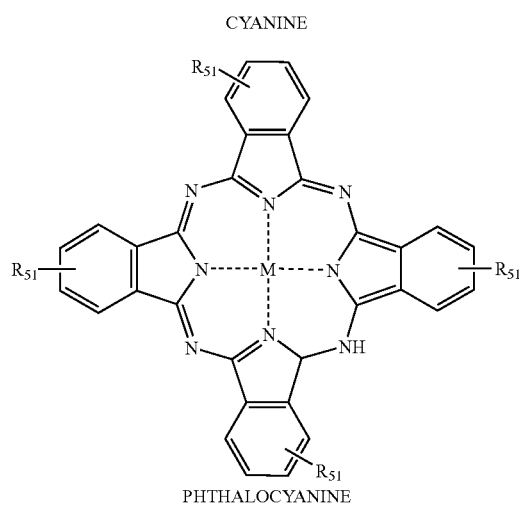
PHTHALOCYANINE

TABLE 1A-continued

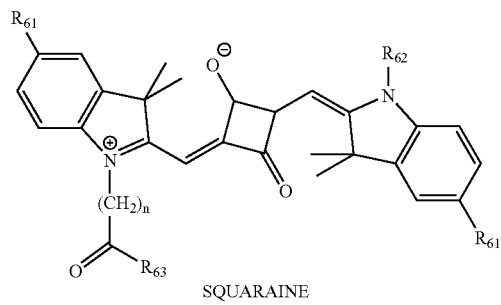
SQUARAINE

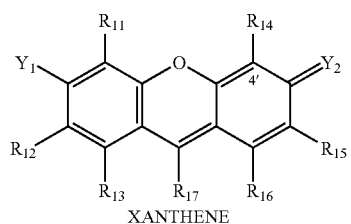
XANTHENE

6.2.1 First Class of Energy Transfer Dyes

As described above, the first class of energy transfer dyes according to the present invention includes a donor dye which is a member of the xanthene class of dyes and hence has a xanthene ring structure with a 4' ring position. Within this class of dyes, the acceptor dye is a dye which is capable of absorbing the excitation energy emitted by the donor dye and fluorescing at a second wavelength in response.

According to this embodiment, the donor may be a member of the fluorescein, rhodamine or asymmetric benzoxanthene classes of dyes, these dyes each being members of the broader xanthene class of dyes. Illustrated below are the general structural formulas for these xanthene dyes. The substituents illustrated on these dyes may be selected from the wide variety of substituents which may be incorporated onto these different classes of dyes since all dyes having the general xanthene, fluorescein, rhodamine, and asymmetric benzoxanthene ring structures are intended to fall within the scope of this invention.

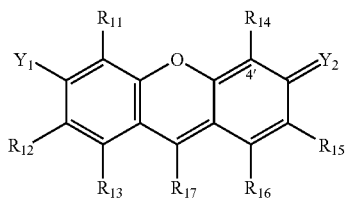
XANTHENE

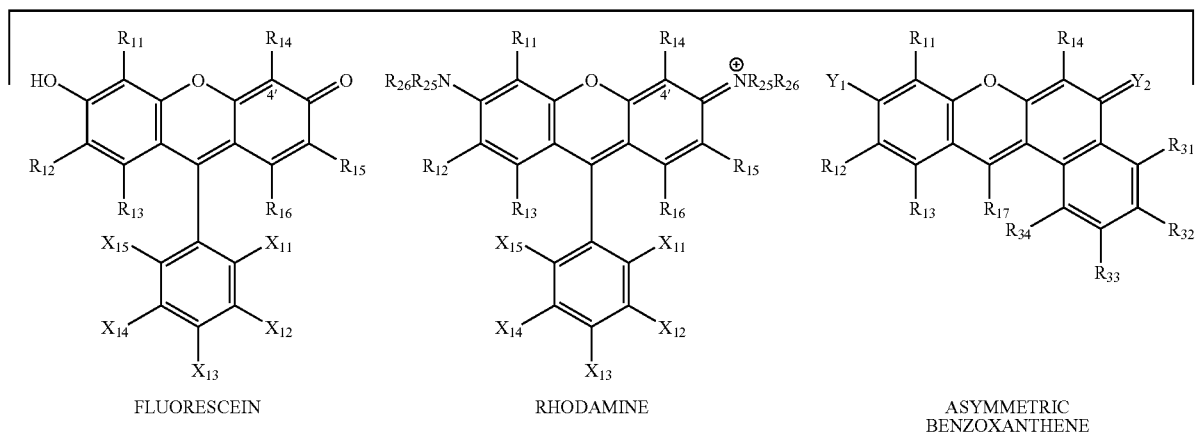
FLUORESCEIN  RHODAMINE  ASYMMETRIC BENZOXANTHENE

Examples of classes of acceptor dyes which may be used in the energy transfer fluorescent dye of this embodiment include, but are not limited to, xanthene dyes, cyanine dyes, phthalocyanine dyes and squaraine dyes. The general structures of these dyes are illustrated in Table 1A. The substituents illustrated on these dyes may be selected from the wide variety of substituents which may be incorporated onto these different classes of dyes since all dyes having the general xanthene, fluorescein, rhodamine, asymmetric benzoxanthene, cyanine, phthalocyanine and squaraine ring structures are intended to fall within the scope of this invention.

Examples of donor dyes which may be used in this embodiment include, but are not limited to fluorescein, isomers of carboxyfluorescein (e.g., 5 and 6 carboxy), isomers of carboxy-HEX (e.g., 5 and 6 carboxy), NAN, Cl-FLAN, TET, JOE, ZOE, rhodamine, isomers of carboxyrhodamine (e.g., 5 and 6 carboxy), isomers of carboxy R110 (e.g., 5 and 6 carboxy), isomers of carboxy R6G (e.g., 5 and 6 carboxy), 4,7-dichlorofluoresceins (See U.S. Pat. No. 5,188,934), 4,7-dichlororhodamines (See application Ser. No. 08/672,196, filed Jun. 27, 1996, now U.S. Pat. No. 5,847,162), asymmetric benzoxanthene dyes (See U.S. application Ser. No. 08/626,085, filed Apr. 1, 1996, now U.S. Pat. No. 6,020,481), and isomers of N,N,N',N'-tetramethyl-carboxyrhodamine (TAMRA) (e.g., 5 and 6 carboxy).

Examples of acceptor dyes which may be used in this embodiment include, but are not limited to isomers of carboxyfluorescein (e.g., 5 and 6 carboxy), 4,7-dichlorofluoresceins, 4,7-dichlororhodamines, fluoresceins, asymmetric benzoxanthene dyes, isomers of carboxy-HEX (e.g., 5 and 6 carboxy), NAN, Cl-FLAN, TET, JOE, ZOE, rhodamine, isomers of carboxyrhodamine (e.g., 5 and 6 carboxy), isomers of carboxy R110 (e.g., 5 and 6 carboxy), isomers of carboxy R6G (e.g., 5 and 6 carboxy), isomers of N,N,N',N'-tetramethyl carboxyrhodamine (TAMRA) (e.g., 5 and 6 carboxy), isomers of carboxy-X-rhodamine (ROX) (e.g., 5 and 6 carboxy) and Cy5. Illustrated in Table 2 are the structures of these dyes.

In the first class of energy transfer dyes according to the present invention, the linker is attached to the donor dye at the 4' position of the xanthene ring structure. In one embodiment, the linker has the general structure $R_{21}Z_1C(O)R_{22}R_{28}$, as illustrated below, where $R_{21}$ is a $C_{1-5}$ alkyl which is attached to the 4' ring position of the donor xanthene dye, $Z_1$ is either NH, sulfur or oxygen, C(O) is a carbonyl group, $R_{22}$ is a substituent which includes an alkene, diene, alkyne, a five and six membered ring having at least one unsaturated bond or a fused ring structure which is attached to the carbonyl carbon, and $R_{28}$ is a functional group which attaches the linker to the acceptor dye.

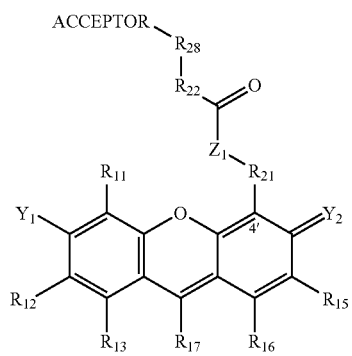

Examples of five or six membered rings which may be used in $R_{22}$ include, but are not limited to cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine and oxazine. Examples of fused ring structures include, but are not limited to indene, benzofuran, thionaphthene, indole and naphthalene.

In one variation of this embodiment, illustrated below, the linker has the general structure $R_{21}Z_1C(O)R_{22}R_{29}Z_2C(O)$ where $R_{21}$ is a $C_{1-5}$ alkyl which is attached to the 4' ring position of the donor xanthene dye, $Z_1$ and $Z_2$ are each independently either NH, sulfur or oxygen, C(O) is a carbonyl group, $R_{22}$ is a substituent which includes an alkene, diene, alkyne, a five and six membered ring having at least one unsaturated bond or a fused ring structure which is attached to the carbonyl carbon, $R_{29}$ is a $C_{1-5}$ alkyl, and the terminal carbonyl group is attached to the ring structure of the acceptor dye.

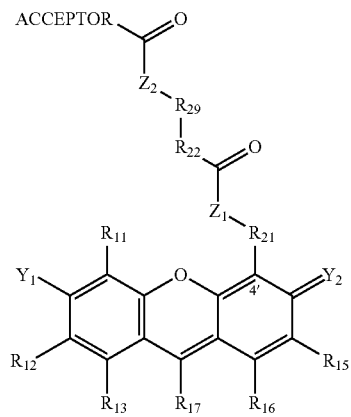

A preferred embodiment of this linker is where $R_{21}$ and $R_{29}$ are methylene, $Z_1$ and $Z_2$ are NH, and $R_{22}$ is benzene, as shown below.

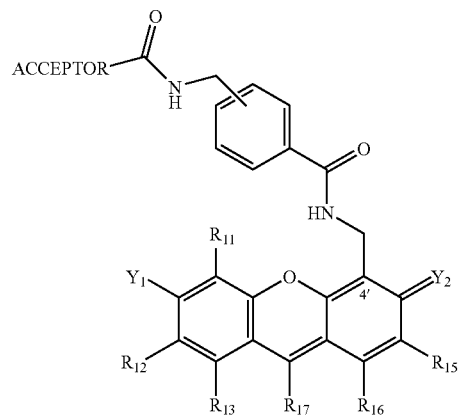

TABLE 2
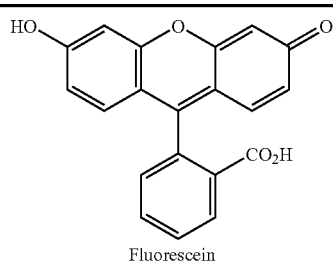
Fluorescein
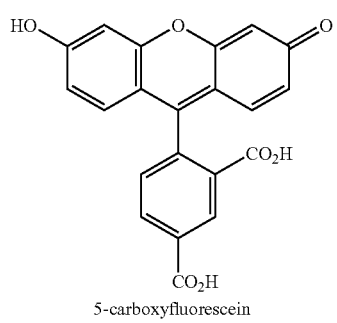
5-carboxyfluorescein
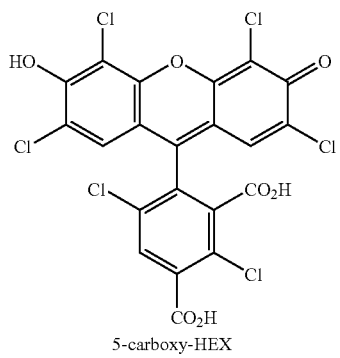
5-carboxy-HEX
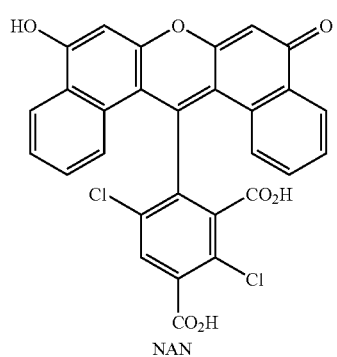
NAN
TABLE 2-continued
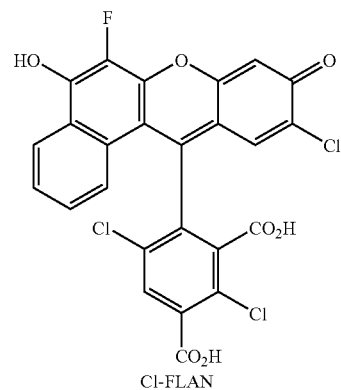
Cl-FLAN
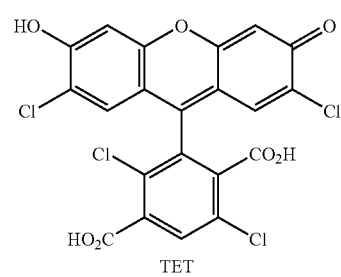
TET
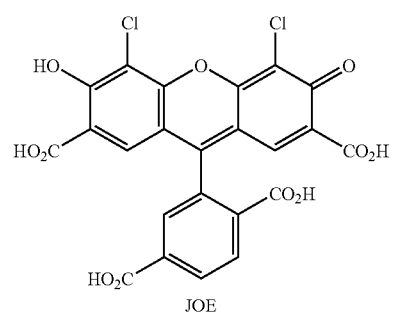
JOE
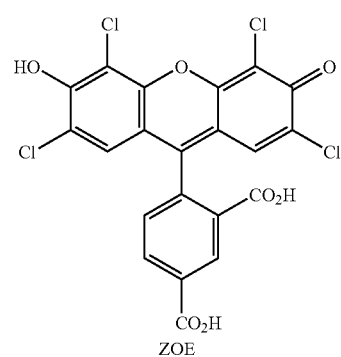
ZOE TABLE 2-continued
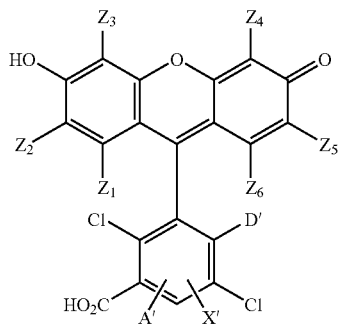
4,7-Dichlorofluorescein
(See U.S. Pat. No. 5,188,934)
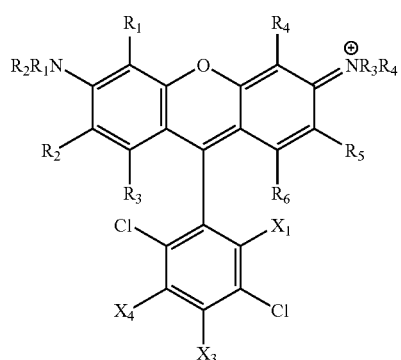
4,7-Dichlororhodamine
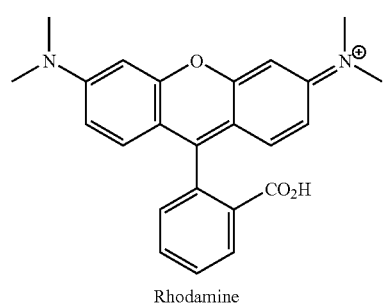
Rhodamine
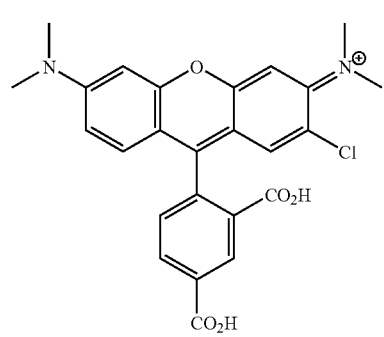
5-carboxyrhodamine
TABLE 2-continued
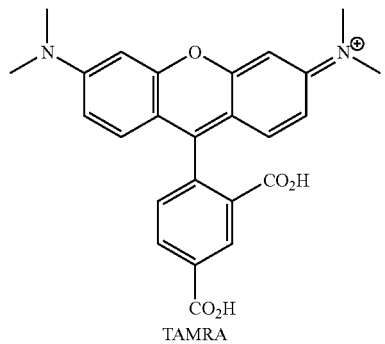
TAMRA
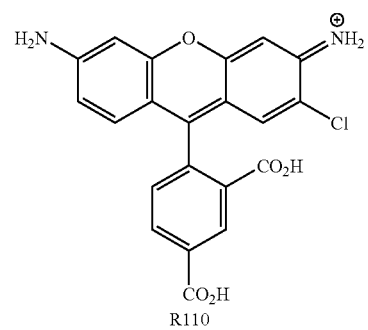
R110
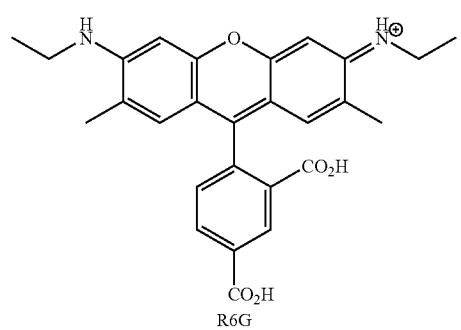
R6G
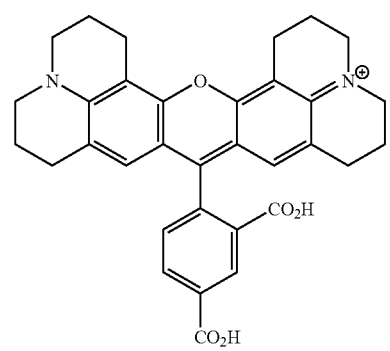
ROX

TABLE 3

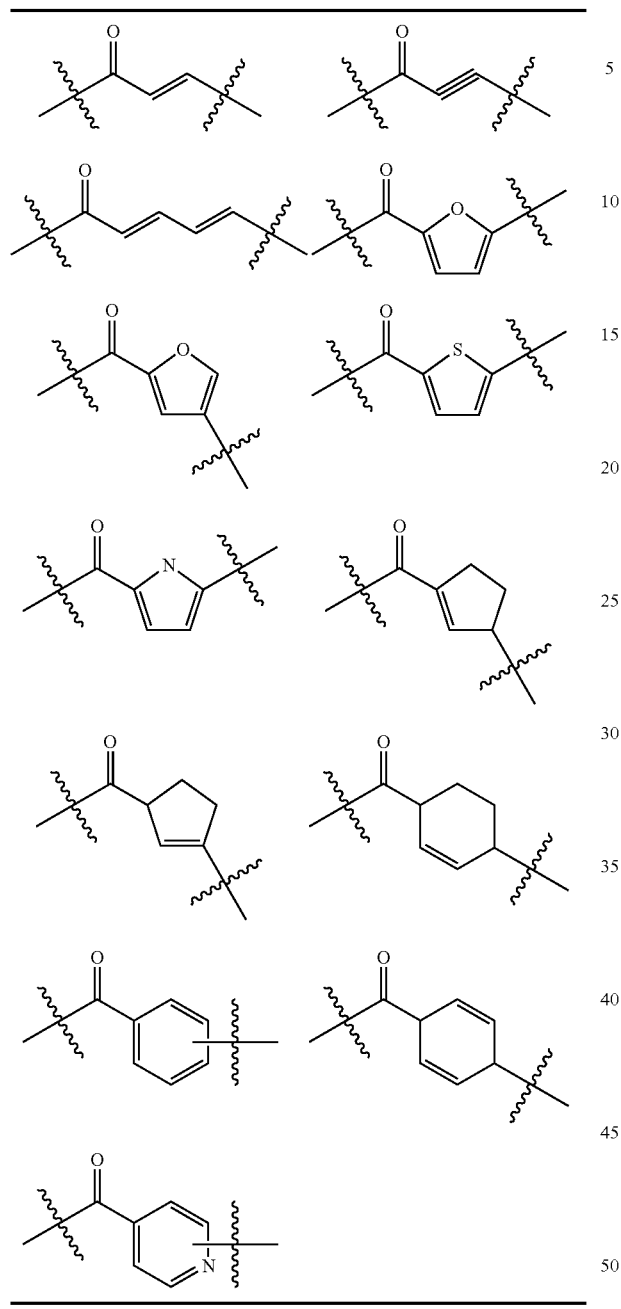

Figure 2:
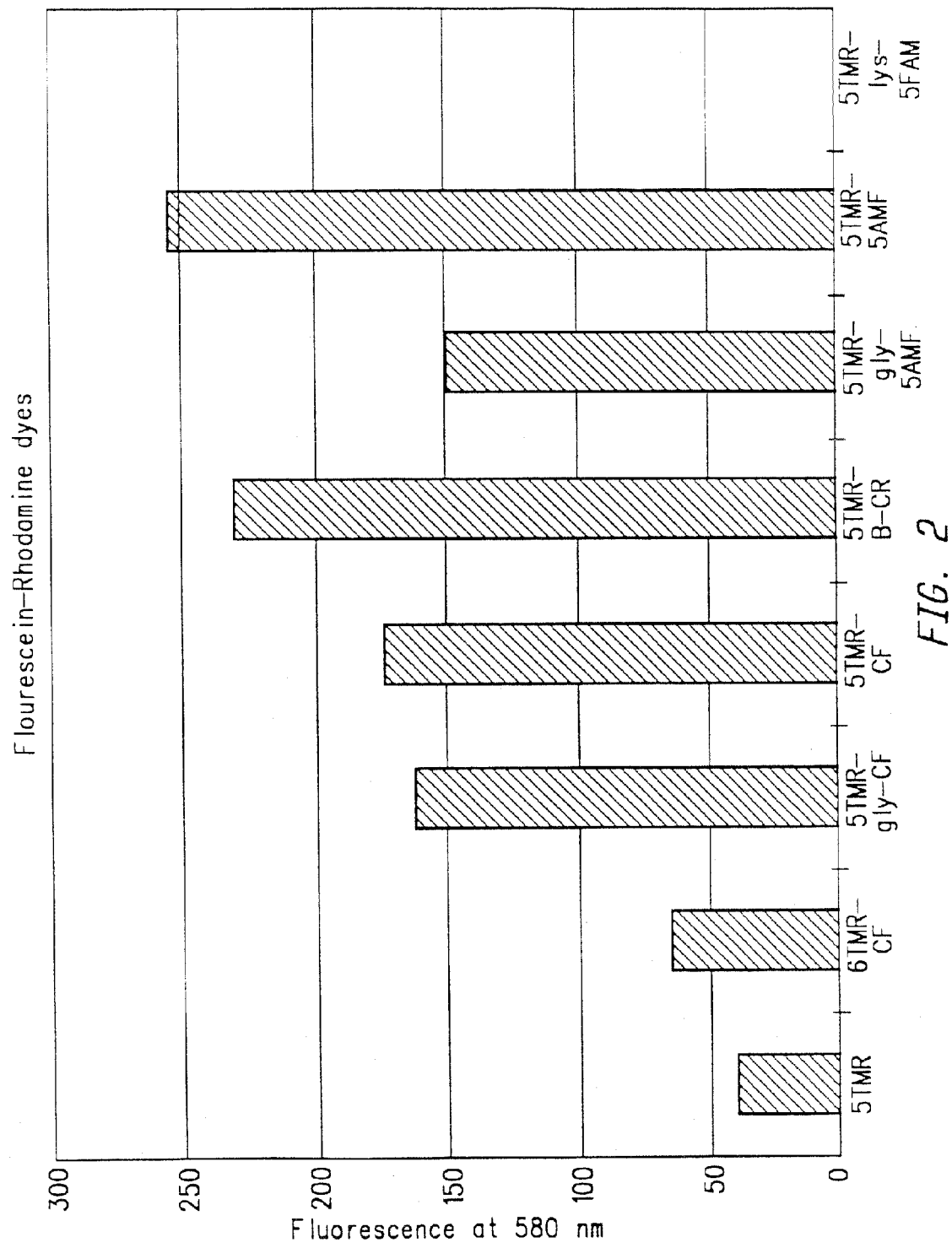

As illustrated in Example 4 and FIG. 2, energy transfer dyes such as 5-TMR-B-CF, which include a donor, acceptor and linker as specified above exhibit enhanced fluorescence as compared to the acceptor itself and energy transfer fluorescent dyes having the same donor-acceptor pair where the linker between the donor-acceptor pair is different. Without being bound by theory, the enhanced fluorescence intensity observed is believed to be due to an improved energy transfer orientation between the donor and acceptor dye which is achieved and maintained by the relatively rigid $R_{22}$ portion of the linker. As a result, the energy transfer fluorescent dyes of the present invention exhibit enhanced fluorescent strength as compared to the acceptor fluorophore itself and energy transfer fluorescent dyes having the same donor-acceptor pair where the linkage between the donor-acceptor pair is different. The enhanced fluorescent strength of these dyes is particularly evident in the presence of 8 M urea which serves to reduce dye stacking.

In one variation of this embodiment, the acceptor is a member of the xanthene class of dyes having the general structure

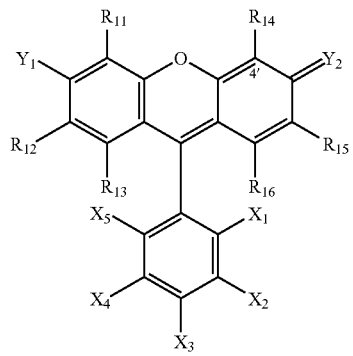

where $Y_1$, $Y_2$, $R_{11}$-$R_{16}$ and $X_1$-$X_5$ are as specified above.

According to this variation, it is preferred that a linker, such as the ones described above, is attached to the acceptor xanthene dye via the $X_3$ or $X_4$ substituent of the acceptor xanthene dye. In a preferred embodiment, as illustrated below, the linker is attached to the $X_3$ substituent of the acceptor xanthene dye.

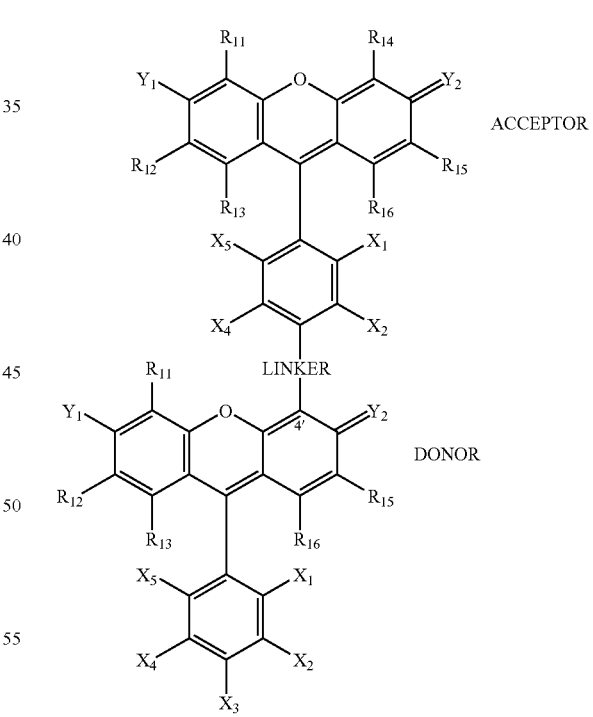

Table 4 provides examples of the above-described energy transfer dyes according to this embodiment of the invention. It is noted that although the dyes illustrated in Table 4 include a 5-carboxyfluorescein donor dye and a TAMRA acceptor dye, it should be understood that a wide variety of other xanthene dyes can be readily substituted as the donor dye. It should also be understood that a wide variety of other xanthene dyes, as well as cyanine, phthalocyanine and squaraine dyes can be readily substituted for the TAMRA acceptor dye, as has been described above, all of these variations with regard to the donor and acceptor dyes falling within the scope of the invention.
TABLE 4
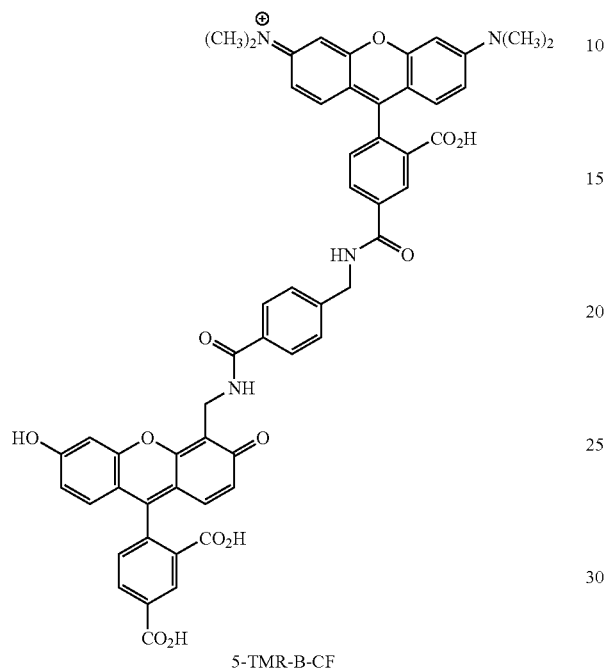
5-TMR-B-CF
TABLE 4-continued
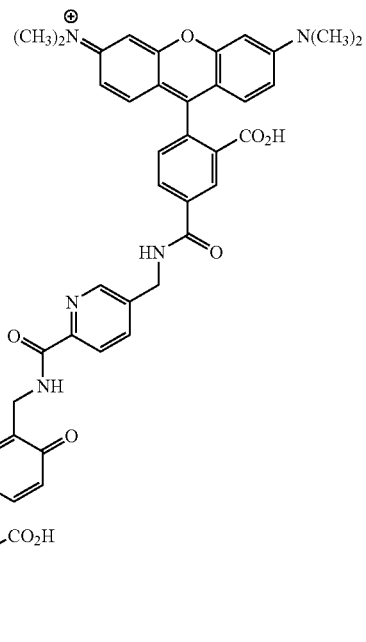
5-TMR-P-CF
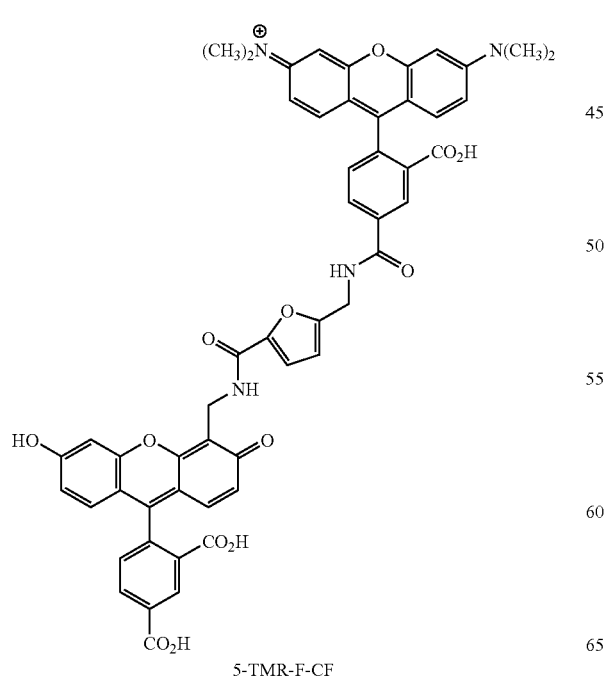
5-TMR-F-CF
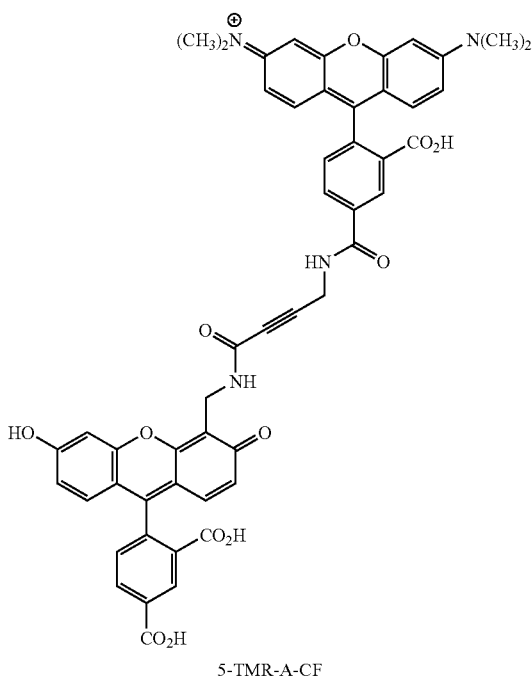
5-TMR-A-CF

TABLE 4-continued
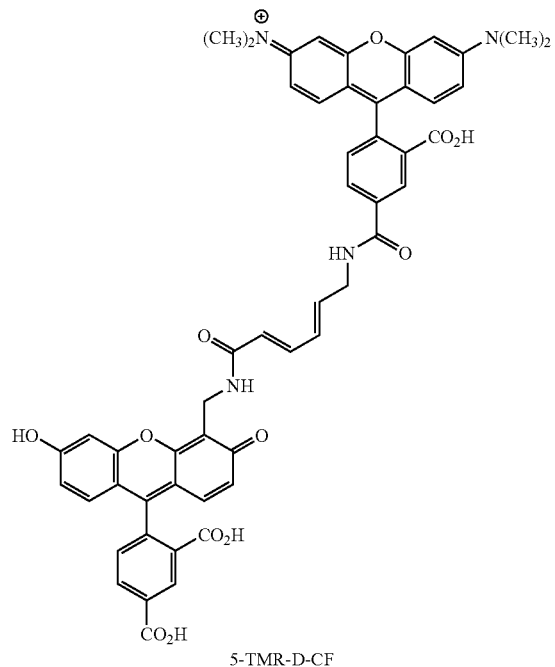
5-TMR-D-CF
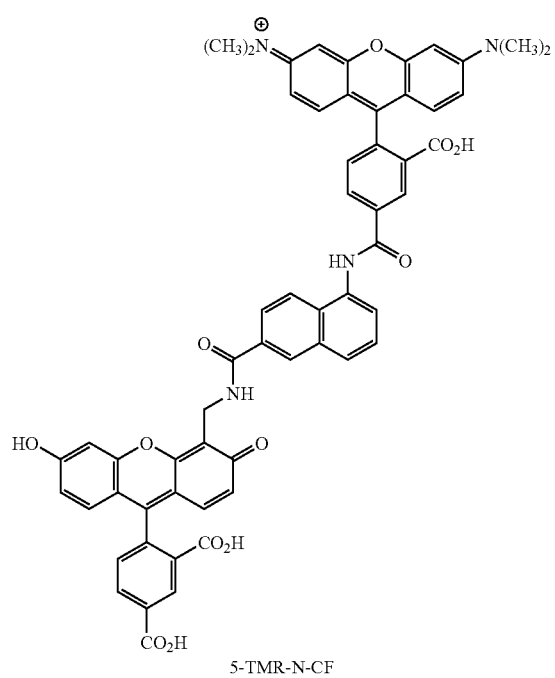
5-TMR-N-CF
TABLE 4-continued
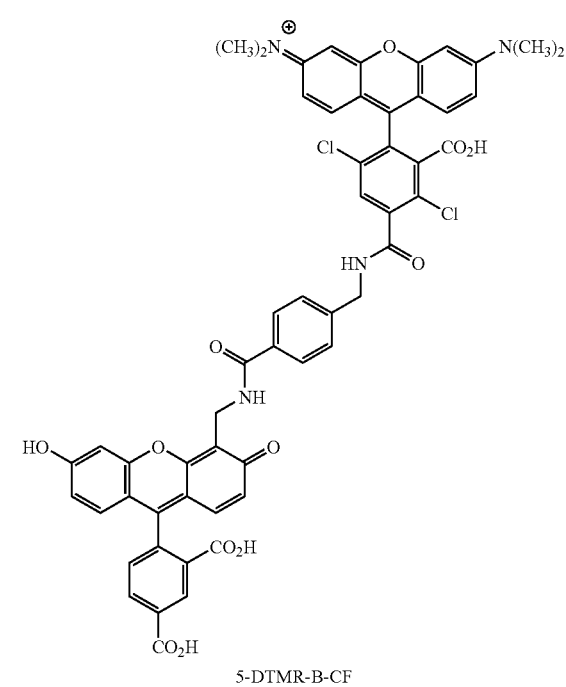
5-DTMR-B-CF
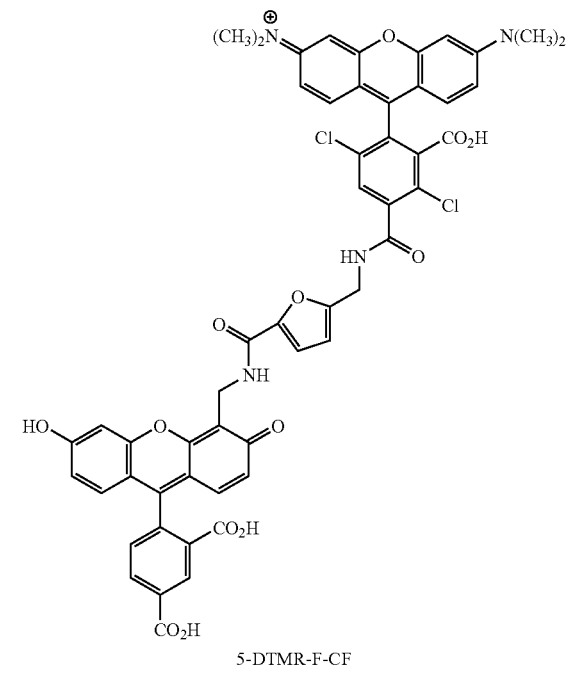
5-DTMR-F-CF TABLE 4-continued
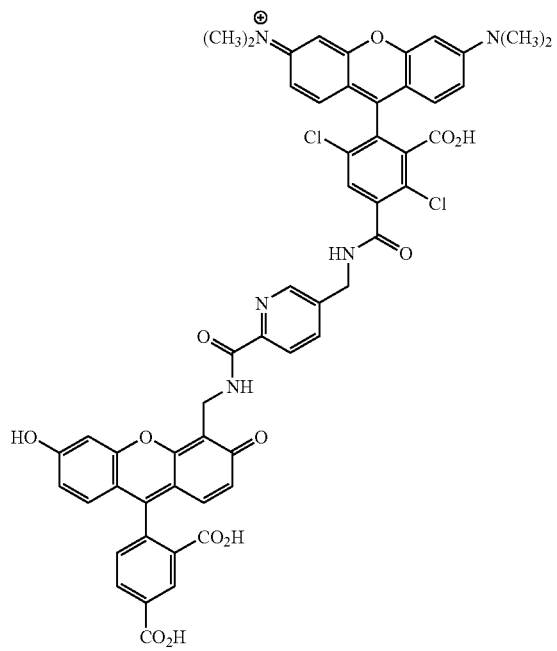
5-DTMR-P-CF
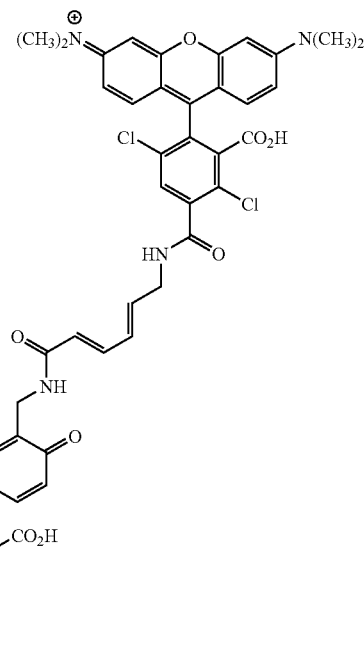
5-DTMR-D-CF
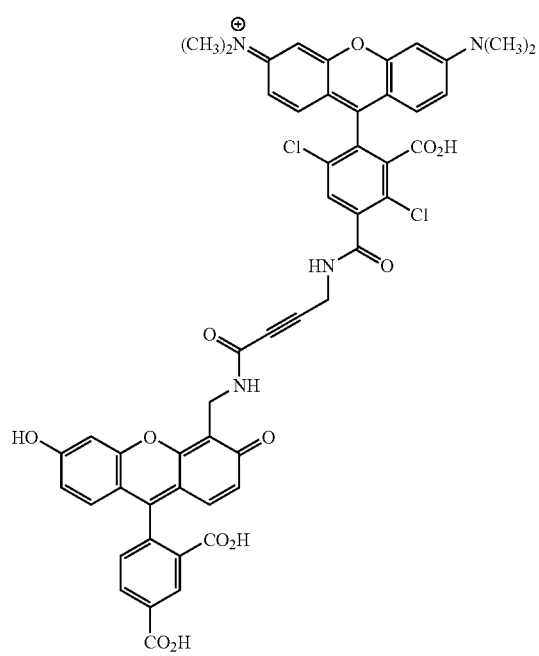
5-DTMR-A-CF
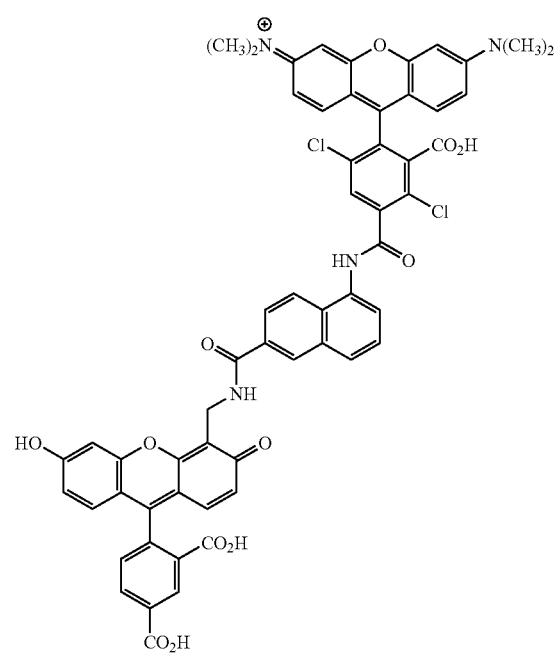
5-DTMR-N-CF

6.2.2 Second Class of Energy Transfer Dyes

The present invention also relates to a second class of energy transfer fluorescent dyes, illustrated below, in which the donor dye and acceptor each are members of the xanthene class of dyes having the general structure

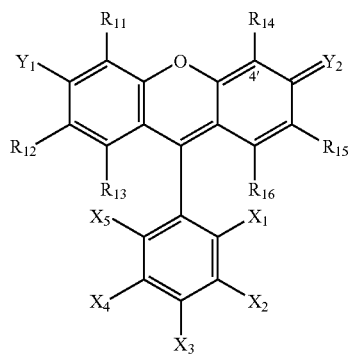

where $Y_1$, $Y_2$, $R_{11}$-$R_{16}$ and $X_1$-$X_5$ are as specified above.

According to this embodiment, the linker is attached to the $X_3$ or $X_4$ substituent of both the donor and acceptor dyes, as illustrated below.

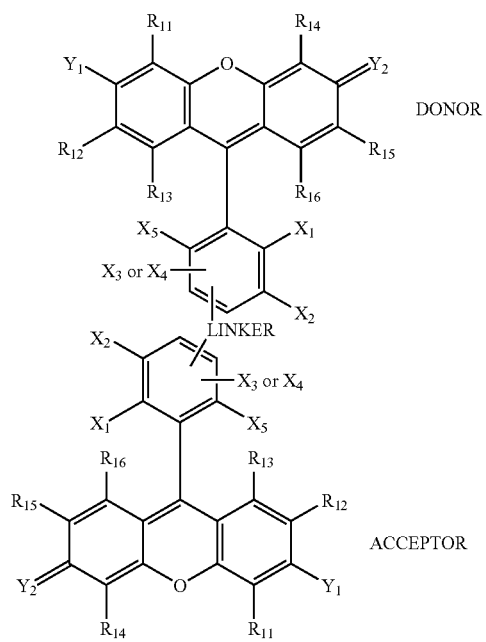

In this embodiment, the linker is preferably short and/or rigid as this has been found to enhance the transfer of energy between the donor and acceptor dyes. For example, in one variation of this embodiment, the linker preferably has a backbone attaching the donor to the acceptor which is less than 9 atoms in length. In another variation of this embodiment, the linker includes a functional group which gives the linker some degree of structural rigidity, such as an alkene, diene, an alkyne, a five and six membered ring having at least one unsaturated bond or a fused ring structure. In yet another variation, the linker has the general formula $R_{25}Z_3C(O)$ or $R_{25}Z_3C(O)R_{26}Z_4C(O)$ where $R_{25}$ is attached to the donor dye, C(O) is a carbonyl group and the terminal carbonyl group is attached to the acceptor dye, $R_{25}$ and $R_{26}$ are each selected from the group of $C_{1-4}$ alkyl, and $Z_3$ and $Z_4$ are each independently either NH, O or S.

Examples of donor and acceptor dyes which may be used in this embodiment include, but are not limited to fluorescein, 5 or 6 carboxyfluorescein, 5 or 6 carboxy-HEX, NAN, Cl-FLAN, TET, JOE, ZOE, 4,7-dichlorofluoresceins, asymmetric benzoxanthene dyes, rhodamine, 5 or 6 carboxyrhodamine, 5 or 6 carboxy-R110, 5 or 6 carboxy-R6G, N,N,N',N'-tetramethyl (5 or 6)-carboxyrhodamine (TAMRA), 5 or 6 carboxy-X-rhodamine (ROX) and 4,7-dichlororhodamines. Illustrated in Table 2 are the structures of these dyes.

In another variation of this embodiment, the linker includes a $R_{27}Z_5C(O)$ group where $R_{27}$ is a $C_{1-5}$ alkyl attached to the donor dye, $Z_5$ is either NH, sulfur or oxygen, and C(O) is a carbonyl group attached to the acceptor dye.

Table 5 provides examples of the second class of energy transfer dyes according to the present invention. It is noted that although the dyes illustrated in Table 5 include a 5-aminomethylfluorescein donor dye, it should be understood that a wide variety of other xanthene dyes can be readily substituted as the donor dye. It should also be understood that a wide variety of other xanthene dyes, as well as cyanine, phthalocyanine and squaraine dyes can be readily substituted for the TAMRA acceptor dye, as has been described above, all of these variations with regard to the donor and acceptor dyes falling within the scope of the invention.

TABLE 5

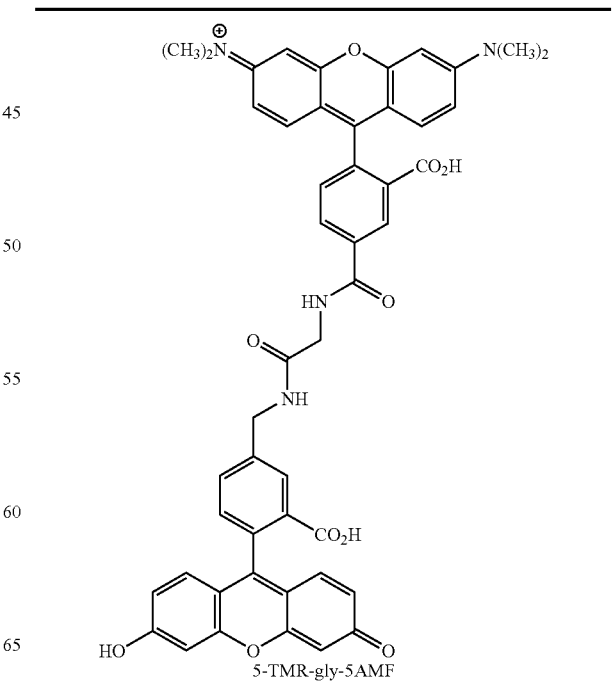

5-TMR-gly-5AMF

TABLE 5-continued
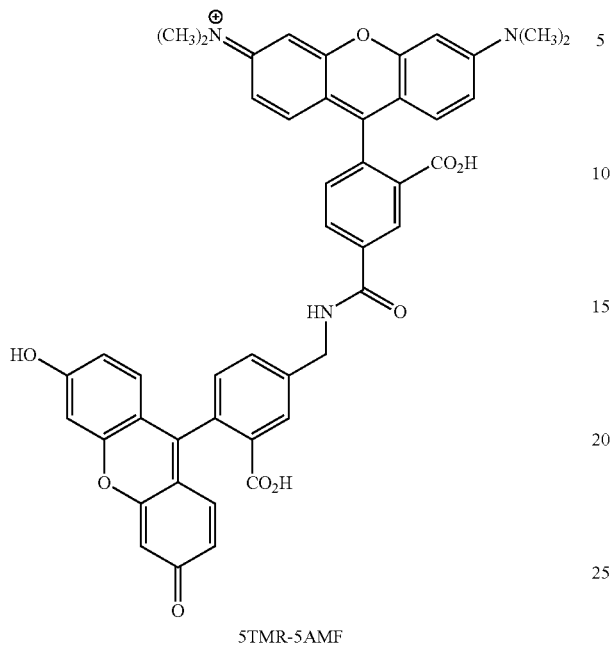
5TMR-5AMF
TABLE 5-continued
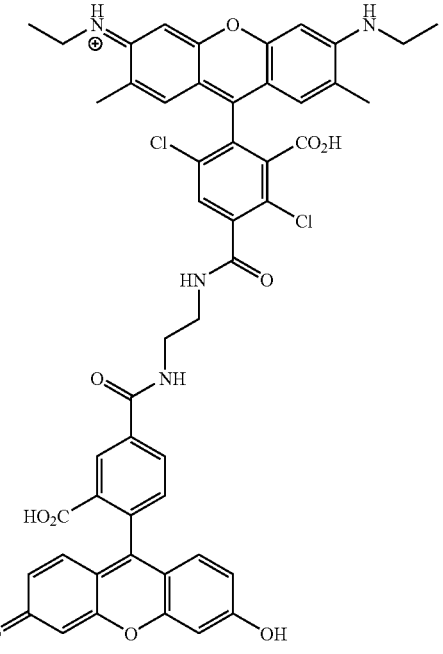

TABLE 5-continued
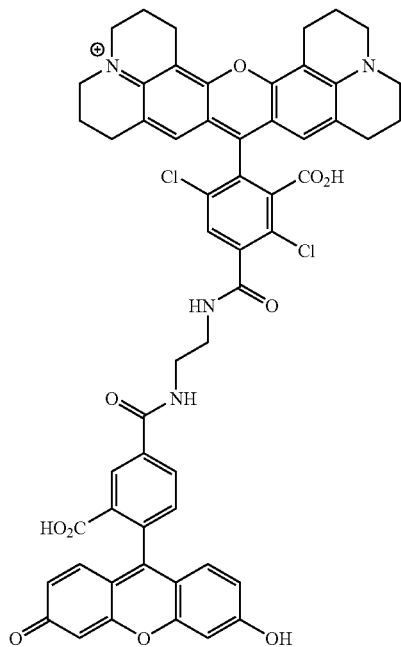
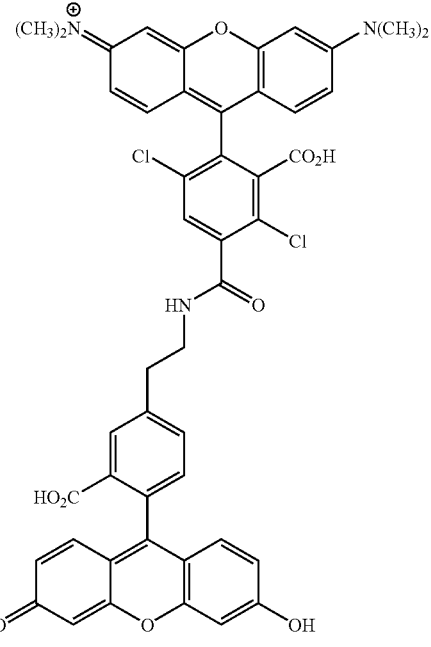
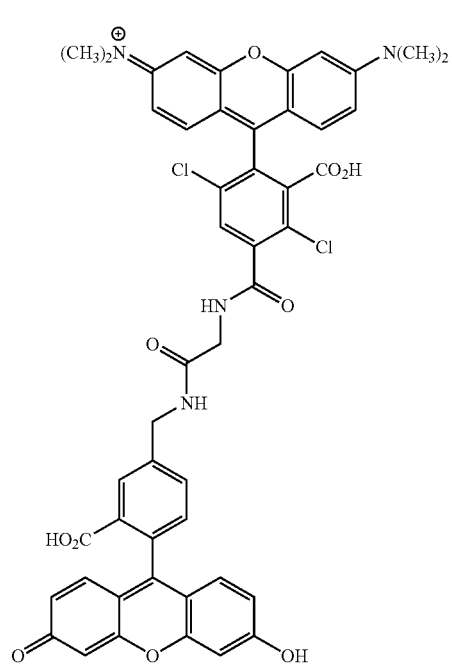
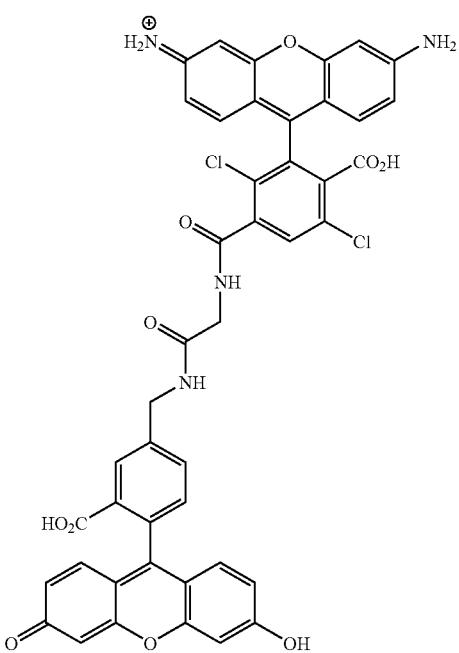

TABLE 5-continued
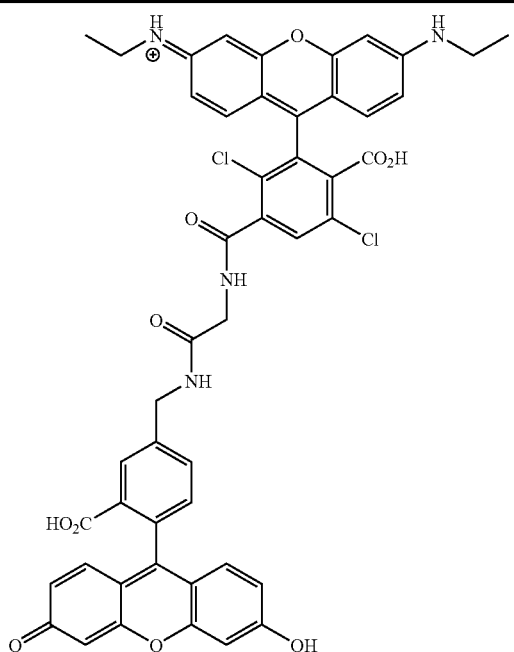
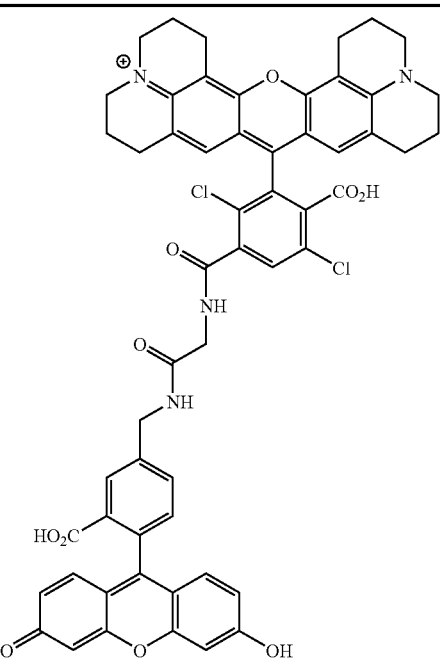
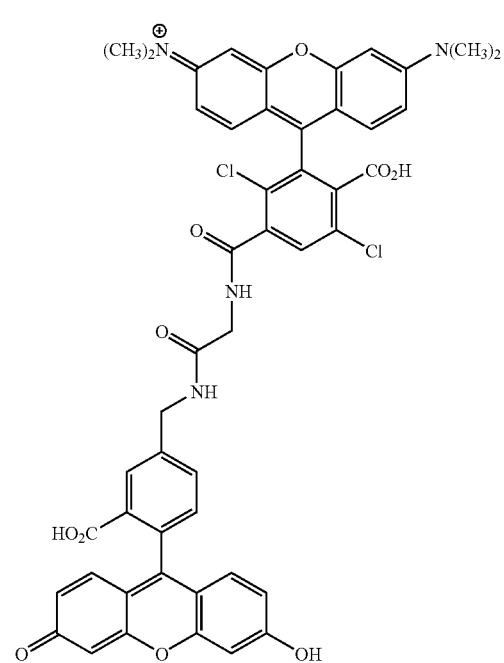
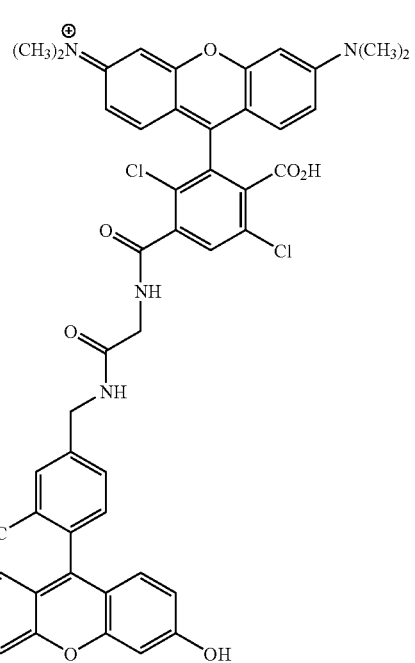

TABLE 5-continued
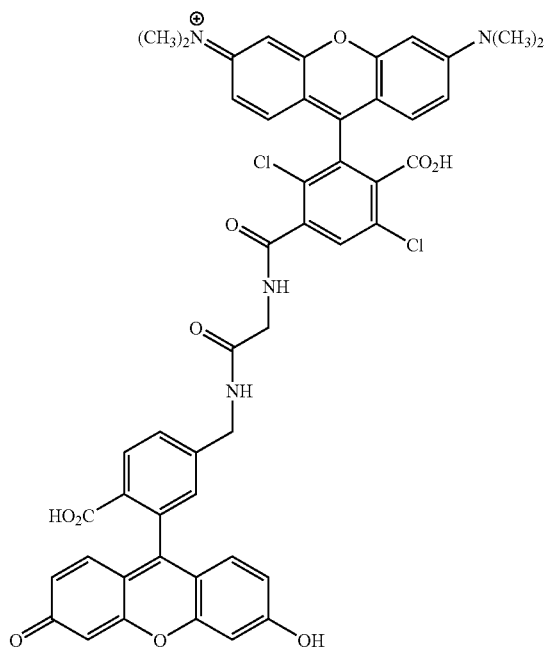
TABLE 5-continued
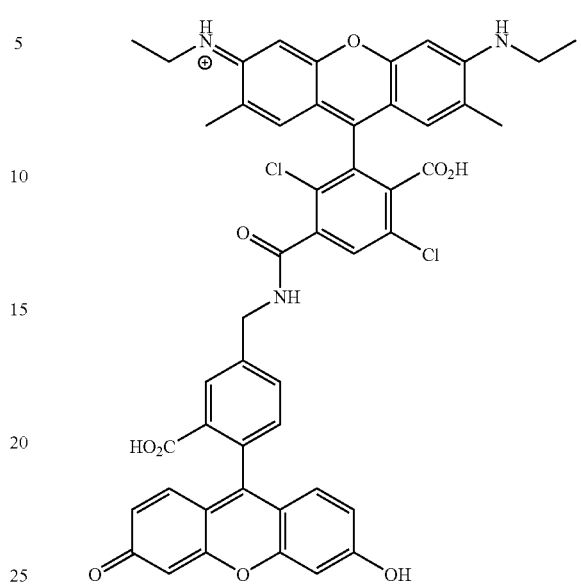
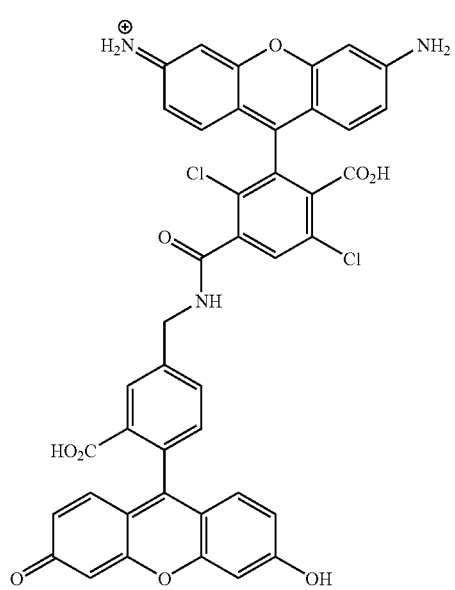
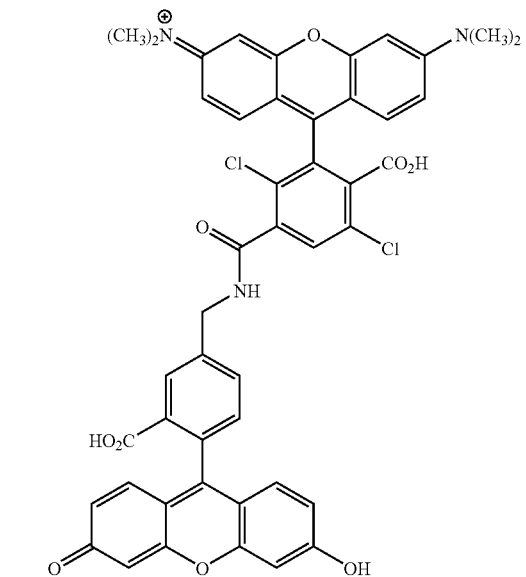

TABLE 5-continued

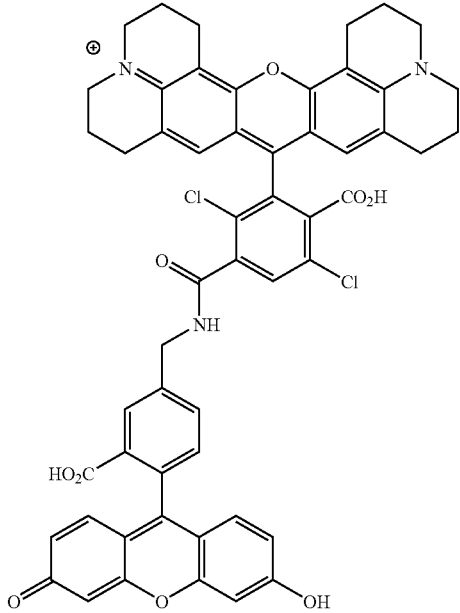

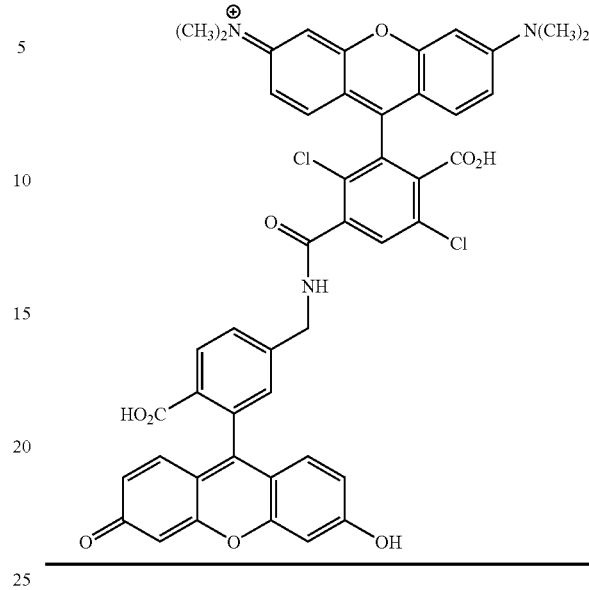

6.2.3 Third Class of Energy Transfer Dyes

The third class of energy transfer fluorescent dyes include a 4,7-dichlororhodamine dye as the acceptor dye and a dye which produces an emission which the 4,7-dichlororhodamine dye can absorb as the donor dye. These dyes exhibit enhanced fluorescence intensity as compared to the acceptor dye alone. In addition, 4,7-dichlororhodamine dyes exhibit a narrower emission spectrum than other rhodamine dyes which facilitates their use in multiple component analyses.

In a preferred embodiment, these energy transfer dyes include those dyes according to the first and second classes of dyes in which the acceptor is a 4,7-dichlororhodamine dye.

6.2.3.1 4,7-Dichlororhodamine Dyes 4,7-dichlororhodamine dye compounds have the general structure

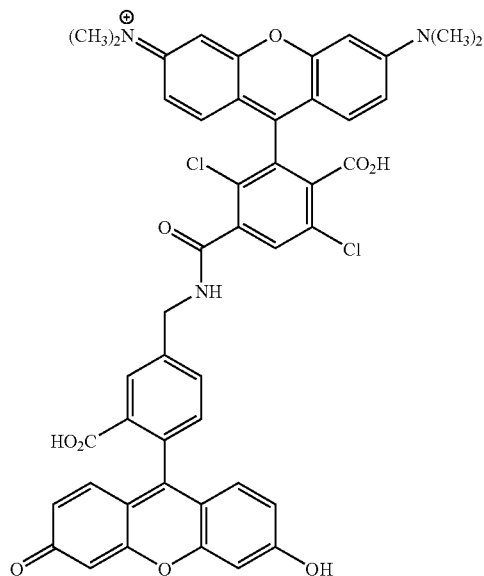

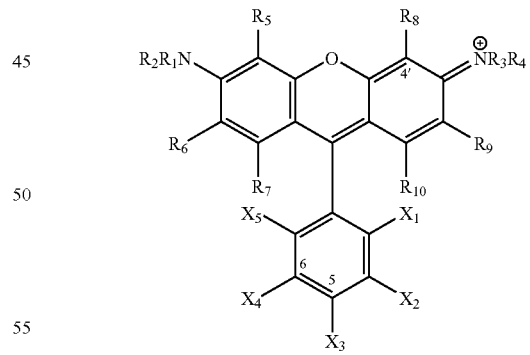

where:

$R_1$-$R_4$ are each independently hydrogen, alkyl or where $R_1$ and $R_5$, $R_2$ and $R_6$, $R_3$ and $R_8$, $R_4$ and $R_9$ are taken together to form a ring, and combinations thereof, $R_5$-$R_{10}$ are each independently hydrogen, fluorine, chlorine, bromine, iodine, carboxyl, alkyl, alkene, alkyne, sulfonate, sulfone, amino, ammonium, amido, nitrile, alkoxy, phenyl, or substituted phenyl, or where adjacent substituents are taken together to form a ring, and combinations thereof;

$X_1$, $X_3$ and $X_4$ are each independently hydrogen, fluorine, chlorine, bromine, iodine, carboxyl, alkyl, alkene, alkyne, sulfonate, sulfone, amino, ammonium, amido, nitrile, or alkoxy, or where adjacent substituents are taken together to form a ring, and combinations thereof; and $X_2$ and $X_5$ are chlorine.

Dyes falling within the 4,7-dichlororhodamine class of dyes and their synthesis are described in U.S. application Ser. No. 08/672,196, filed Jun. 27, 1996, now U.S. Pat. No. 5,847,162, entitled "4,7-DICHLORORHODAMINE DYES," which is incorporated herein by reference.

With regard to $R_1$-$R_4$, alkyl substituents may include between about 1 to 8 carbon atoms (i.e., methyl, ethyl, propyl, isopropyl, tert-butyl, isobutyl, sec-butyl, neopentyl, tert-pentyl, and the like) and may be straight-chain and branched hydrocarbon moieties. In a preferred embodiment, $R_1$-$R_4$ are each independently either hydrogen, methyl, or ethyl and more preferably either hydrogen or methyl.

With regard to $R_5$-$R_{10}$, alkyl, alkene, alkyne and alkoxy substituents preferably include between about 1 to 8 carbon atoms (i.e., methyl, ethyl, propyl, isopropyl, tert-butyl, isobutyl, sec-butyl, neopentyl, tert-pentyl, and the like) and may be straight-chain and branched hydrocarbon moieties.

With regard to $R_1$-$R_{10}$, $R_1$ and $R_5$, $R_2$ and $R_6$, $R_3$ and $R_8$, $R_4$ and $R_9$ may each independently be taken together to form a 5, 6, or 7 membered ring.

In one embodiment, $R_6$ and $R_7$ is benzo, and/or, $R_9$ and $R_{10}$ is benzo. In a preferred embodiment, $R_5$-$R_{10}$ are each independently either hydrogen, methyl, or ethyl and more preferably either hydrogen or methyl.

With regard to $X_1$, $X_3$ and $X_4$, $X_1$ is preferably a carboxylate and one of $X_3$ and $X_4$ may include a substituent which is used to link the 4,7-dichlororhodamine acceptor dye to a donor dye or to link a nucleotide or an oligonucleotide to the energy transfer dye. The $R_8$ substituent at the 4' ring position may also be used to link the acceptor to either the donor dye or to a biomolecule such as a nucleotide or oligonucleotide.

In one particularly preferred acceptor dye that may be used in the present invention, referred to herein as DR110-2, $R_1$-$R_{10}$ taken separately are hydrogen, $X_1$ is carboxylate, and one of $X_3$ and $X_4$ is a linking group (L), the other being hydrogen. The structure of DR110-2 is shown below.

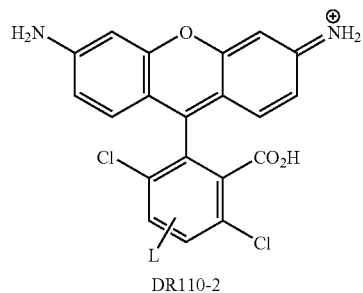

DR110-2

In a second particularly preferred acceptor dye that may be used in the present invention, referred to herein as DR6G-2, one of $R_1$ and $R_2$ is ethyl, the other being hydrogen, one of $R_3$ and $R_4$ is ethyl, the other being hydrogen, $R_5$ and $R_8$ taken separately are methyl, $R_6$, $R_7$, $R_9$, and $R_{10}$ are hydrogen, $X_1$ is carboxylate, and one of $X_3$ and $X_4$ is a linking group, the other being hydrogen. The structure of DR6G-2 is shown below.

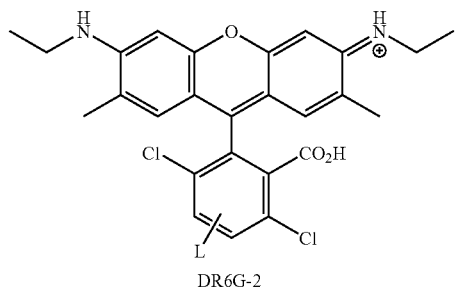

DR6G-2

In a third particularly preferred acceptor dye that may be used in the present invention, referred to herein as DTMR, $R_1$-$R_6$ taken separately are hydrogen, $Y_1$-$Y_4$ taken separately are methyl, $X_1$ is carboxylate, and one of $X_2$ and $X_3$ is linking group, the other being hydrogen. The structure of DTMR is shown below.

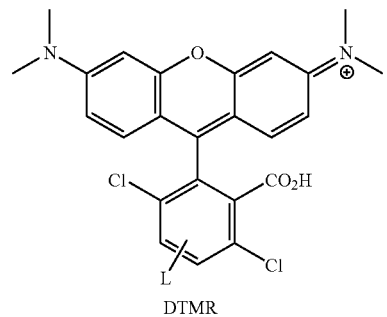

DTMR

In a fourth particularly preferred acceptor dye that may be used in the present invention, referred to herein as DROX, $R_1$ and $R_6$ are taken together to form a six membered ring, $R_2$ and $R_5$ are taken together to form a six membered ring, $R_3$ and $R_7$ are taken together to form a six membered ring, $R_4$ and $R_8$ are taken together to form a six membered ring, $R_5$ and $R_6$ are hydrogen, $X_1$ is carboxylate, and one of $X_3$ and $X_4$ is a linking group, the other being hydrogen. The structure of DROX is shown below.

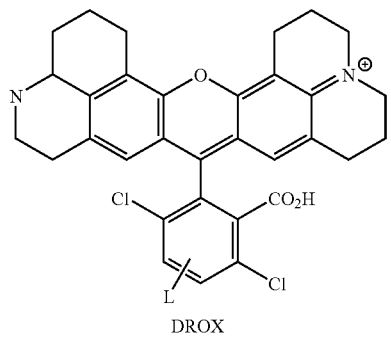

DROX

FIGS. 3A and 3B show several additional preferred embodiments of 4,7-dichlororhodamine dyes which can be used in the energy transfer dyes of the present invention.

In compound 3A-A, one of $R_1$ and $R_2$ is ethyl, the other being hydrogen, $R_3$ and $R_4$ taken separately are hydrogen, $R_6$ is methyl, $R_5$ and $R_7$-$R_{10}$ taken separately are hydrogen, $X_1$ is carboxylate, and one of $X_3$ and $X_4$ is a linking group, the other being hydrogen.

In compound 3A-B, one of $R_1$ and $R_2$ is ethyl, the other being hydrogen, $R_3$ and $R_4$ taken separately are methyl, $R_5$ is methyl, $R_6$-$R_{10}$ taken separately are hydrogen, $X_1$ is carboxylate, and, one of $X_3$ and $X_4$ is a linking group, the other being hydrogen.

In compound 3A-C, $R_1$ and $R_2$ taken separately are methyl, $R_3$ and $R_9$ taken together form a six membered ring, $R_4$ and $R_8$ taken together form a six membered ring, $R_5$, $R_6$, $R_7$, and $R_{10}$ taken separately are hydrogen, $X_1$ is carboxylate, and, one of $X_3$ and $X_4$ is a linking group, the other being hydrogen.

In compound 3B-D, $R_1$ and $R_2$ taken separately are hydrogen, $R_3$ and $R_9$ taken together form a six membered ring, $R_4$ and $R_8$ taken together form a six membered ring, $R_5$, $R_6$, $R_7$, and $R_{10}$ taken separately are hydrogen, $X_1$ is carboxylate, and one of $X_3$ and $X_4$ is a linking group, the other being hydrogen.

In compound 3B-E, one of $R_1$ and $R_2$ is ethyl, the other being hydrogen, $R_3$ and $R_9$ taken together form a six membered ring, $R_4$ and $R_8$ taken together form a six membered ring, $R_5$ is methyl, $R_6$, $R_7$ and $R_{10}$ taken separately are hydrogen, $X_1$ is carboxylate, and, one of $X_3$ and $X_4$ is a linking group, the other being hydrogen.

In compound 3B-F, $R_1$ and $R_2$ taken separately are hydrogen, $R_3$ and $R_4$ taken separately are methyl, $R_5$-$R_{10}$ taken separately are hydrogen, $X_1$ is carboxylate, and, one of $X_3$ and $X_4$ is linking group, the other being hydrogen.

FIGS. 4A and 4B show preferred generalized synthesis schemes for the preparation of 4,7-dichlororhodamine dyes used in the energy transfer dyes of this invention. The variable substituents indicated in each figure are as previously defined.

FIG. 4A shows a generalized synthesis wherein the substituent $X_1$ can be other than carboxylate. In the figure, X' indicates moieties which are precursors to $X_1$. In the method illustrated in FIG. 4A, two equivalents of a 3-aminophenol derivative 4A-A/4A-B, such as 3-dimethylaminophenol, is reacted with one equivalent of a dichlorobenzene derivative 4A-C, e.g., 4-carboxy-3,6,dichloro-2-sulfobenzoic acid cyclic anhydride, i.e., where the $X_1$' moieties of 4A-C taken together are —C(O)—O—S(O)$_2$—.

The reactants are then heated for 12 h in a strong acid, e.g., polyphosphoric acid or sulfuric acid, at 180° C. The crude dye 4A-D is precipitated by addition to water and isolated by centrifugation. To form a symmetrical product, the substituents of reactants 4A-A and 4A-B are the same, while to form an asymmetrical product, the substituents are different.

FIG. 4B shows a generalized synthesis wherein the substituent $X_1$ is carboxylate. In the method of FIG. 4B, two equivalents of a 3-aminophenol derivative 4A-A/4A-B, such as 3-dimethylaminophenol, is reacted with one equivalent of a phthalic anhydride derivative 4B-E, e.g. 3,6-dichlorotrimellitic acid anhydride. The reactants are then heated for 12 h in a strong acid, e.g., polyphosphoric acid or sulfuric acid, at 180° C. The crude dye 4A-D is precipitated by addition to water and isolated by centrifugation. To form a symmetrical product, the substituents of reactants 4A-A and 4A-B are the same, while to form an asymmetrical product, the substituents are different.

6.2.3.2 Energy Transfer Dyes with 4,7-Dichlororhodamine as the Acceptor

In general, the energy transfer dyes of the present invention include a donor dye which absorbs light at a first wavelength and emits excitation energy in response, a 4,7-dichlororhodamine acceptor dye which is capable of absorbing the excitation energy emitted by the donor dye and fluorescing at a second wavelength in response, and a linker which attaches the donor dye to the acceptor dye. Preferred examples of this class of dyes which use a 4,7-dichlororhodamine dye as the acceptor dye is illustrated in Table 1.

Examples of acceptor dyes which may be used in this class of dyes include, but are not limited to DR110-2, DR6G-2, DTMR, DROX, as illustrated above, as well as the dyes illustrated in FIGS. 3A-3B.

One subclass of these energy transfer fluorescent dyes are the dyes according to the first class of dyes of the present invention in which the acceptor dye is a 4,7-dichlororhodamine dye. The general structure of these dyes is illustrated below.

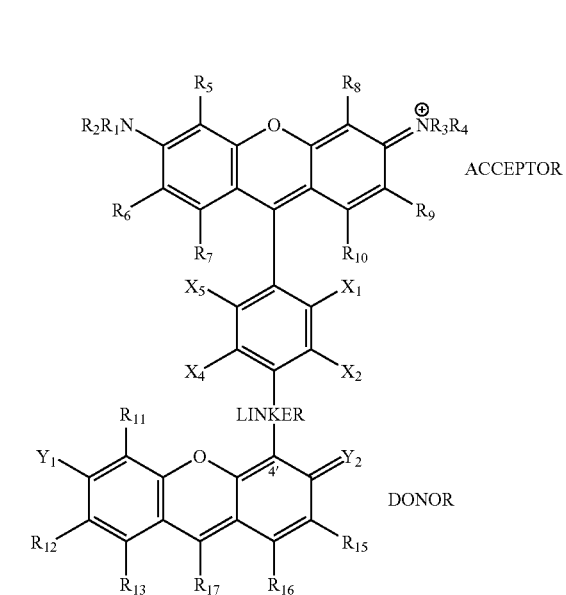

Table 4 provides examples of the energy transfer dyes belonging to the first class of dyes in which a 4,7 dichlororhodamine is used as the acceptor dye. It is noted that although the dyes illustrated in Table 4 include a 5-carboxyfluorescein donor dye and a 5 or 6 carboxy DTMR as the acceptor dye, it should be understood that a wide variety of other xanthene dyes can be readily substituted as the donor dye and a wide variety of other 4,7-dichlororhodamine dyes can be readily substituted for the DTMR acceptor dye, all of these variations with regard to the donor and acceptor dyes being intended to fall within the scope of the invention.

Another subclass of these energy transfer fluorescent dyes are the dyes according to the second class of dyes of the present invention in which the acceptor dye is a 4,7-dichlororhodamine dye. The general structure of these dyes where the donor xanthene dye and acceptor 4,7-dichlororhodamine dye are linked to each other at either the five or six ring positions of the donor and acceptor dyes is illustrated below.

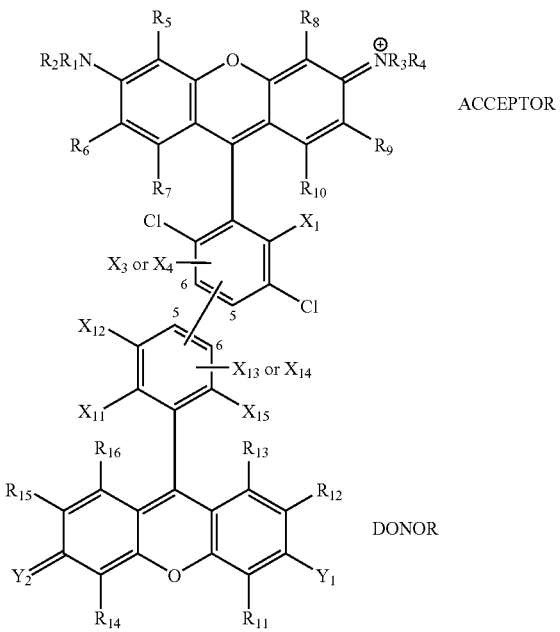

As described above, in this embodiment, the linker attaching the donor to the acceptor dye is preferably short and/or rigid as this has been found to enhance the transfer of energy between the donor and acceptor dyes. The substituent labels shown above correspond to the same groups of substituents as has been specified with regard to the other dyes.

Table 5 provides examples of the second class of energy transfer dyes according to the present invention in which 4,7 dichlororhodamine is used as the acceptor dye. It is noted that although the dyes illustrated in Table 5 include a 5-aminomethylfluorescein donor dye, it should be understood that a wide variety of other xanthene dyes can be readily substituted as the donor dye. It should also be understood that a wide variety of other 4,7-dichlororhodamine dyes can be readily substituted for the acceptor dye shown in Table 5 since, as has been described above, all of these variations with regard to the donor and acceptor dyes are intended to fall within the scope of the invention.

6.2.4 Fourth Class of Energy Transfer Dyes

The present invention also relates to a fourth class of energy transfer fluorescent dyes in which the donor dye is a member of the xanthene class of dyes, and the acceptor dye is a member of the xanthene, cyanine, phthalocyanine or squaraine classes of dyes. Within this class of energy transfer dyes, it is preferred that the donor be a member of the fluorescein class of dyes and the acceptor dye have an emission maximum that is greater than about 600 nm and/or an emission maximum that is at least about 100 nm greater than the absorbance maximum of the donor dye.

The fourth class of dyes of the present invention exhibit unusually large Stoke shifts, as measured by the difference between the absorbance of the donor and the emission of the acceptor. In addition, these dyes exhibit efficient energy transfer in that minimal donor fluorescence is observed. Interestingly, energy is transferred from the donor to the acceptor in some of the dyes belonging to this class even though the absorbance spectrum of the acceptor dye does not overlap with the emission spectrum of the donor dye.

Examples of acceptor dyes which may be used in this embodiment include, but are not limited to 5-carboxy-X-rhodamine (ROX) and Cy5.

The energy transfer dyes of this embodiment also include a linker which attaches the donor to the acceptor. The linker used to attach the donor to the acceptor dye may be any linker according to the first and second classes of dyes. However, it is foreseen that alternate linkers may be used in this class of dyes.

In one embodiment of this class of dyes, the linker is attached to the 4' position of the donor dye's xanthene ring structure. The linker preferably has a general structure $R_{21}Z_1C(O)R_{22}R_{28}$, as described above where $R_{21}$ is a $C_{1-5}$ alkyl which is attached to the 4' ring position of the donor xanthene dye, $Z_1$ is either NH, sulfur or oxygen, C(O) is a carbonyl group, $R_{22}$ is a substituent which includes an alkene, diene, alkyne, a five and six membered ring having at least one unsaturated bond or a fused ring structure which is attached to the carbonyl carbon, and $R_{28}$ is a functional group which attaches the linker to the acceptor dye. In cases where the acceptor dye is a member of the xanthene class of dyes, the linker is preferably attached to acceptor at the 5 position of the xanthene ring structure.

Table 6 provides examples of the above-described energy transfer dyes according to the present invention. It is noted that although the dyes illustrated in Table 6 include a 5-carboxyfluorescein donor dye it should be understood that a wide variety of other xanthene dyes can be readily substituted as the donor dye. It should also be understood that a wide variety of other xanthene dyes, as well as cyanine, phthalocyanine and squaraine dyes can be readily substituted for the 5-carboxy ROX and Cy5 acceptor dyes, as has been described above, all of these variations with regard to the donor and acceptor dyes falling within the scope of the invention.

Figure 5:
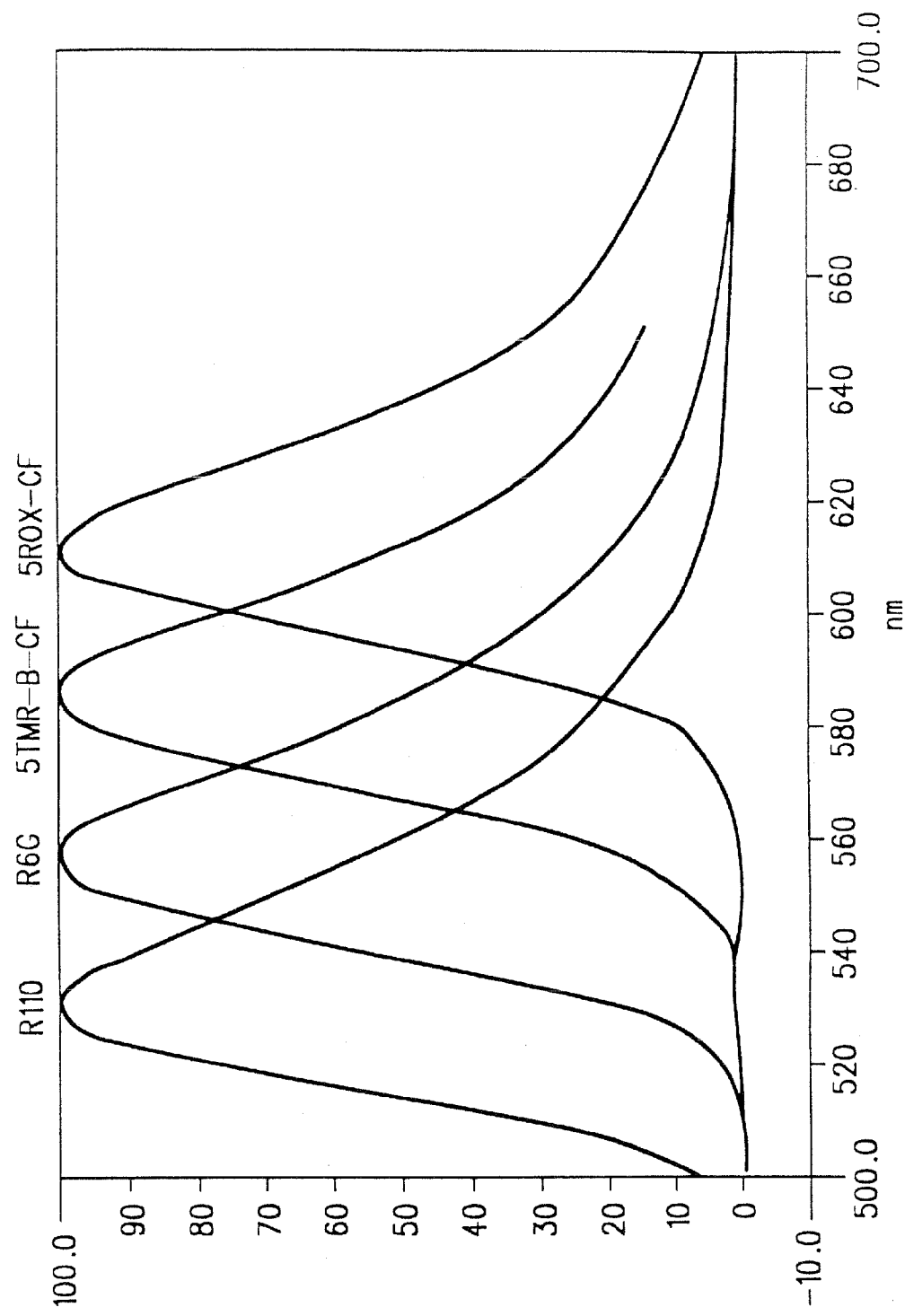
FIG. 5 illustrates a set of four dyes (3-carboxy-R110, 5-carboxy-R6G, 5TMR-B-CF and 5ROX-CF) which are spectrally resolvable from each other.
Figure 6:
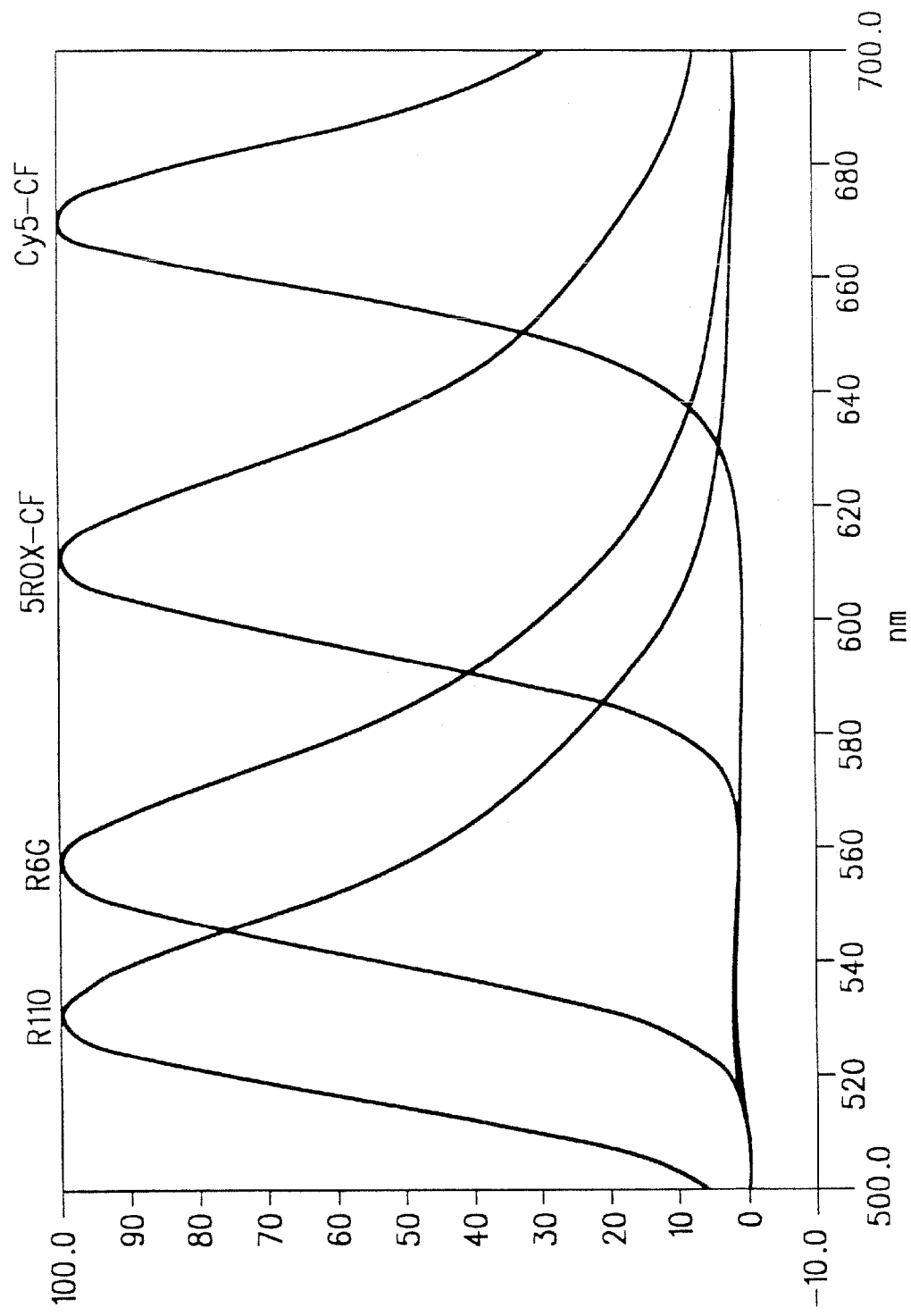
FIG. 6 illustrates a set of four dyes (3-carboxy-R110, 5-carboxy-R6G, 5ROX-CF and Cy5-CF) which are spectrally resolvable from each other.

The energy transfer dyes of this embodiment exhibit unusually large Stoke shifts which make these dyes particularly well suited for use with dyes having smaller Stoke shifts in four dye DNA sequencing. For example, FIGS. 5 and 6 illustrate two sets of four dyes which are spectrally resolvable from each other. Within FIG. 5, 5ROX-CF is a dye falling within the scope of the fourth class of dyes described above. Meanwhile, FIG. 6 includes 5ROX-CF and Cy5-CF which both fall within the scope of the fourth class of dyes described above.

As can be seen from the emission spectra of 5ROX-CF and Cy5-CF illustrated in FIG. 6, very little fluorescence from the donor dye (5-carboxyfluorescein, 520 nm) is observed in these dyes. This is an unexpected result in view of the large difference between the emission maximum of the donor dye (fluorescein) and the absorbance maximum of the acceptor dyes (ROX, 590 nm, Cy5, 640 nm).

TABLE 6

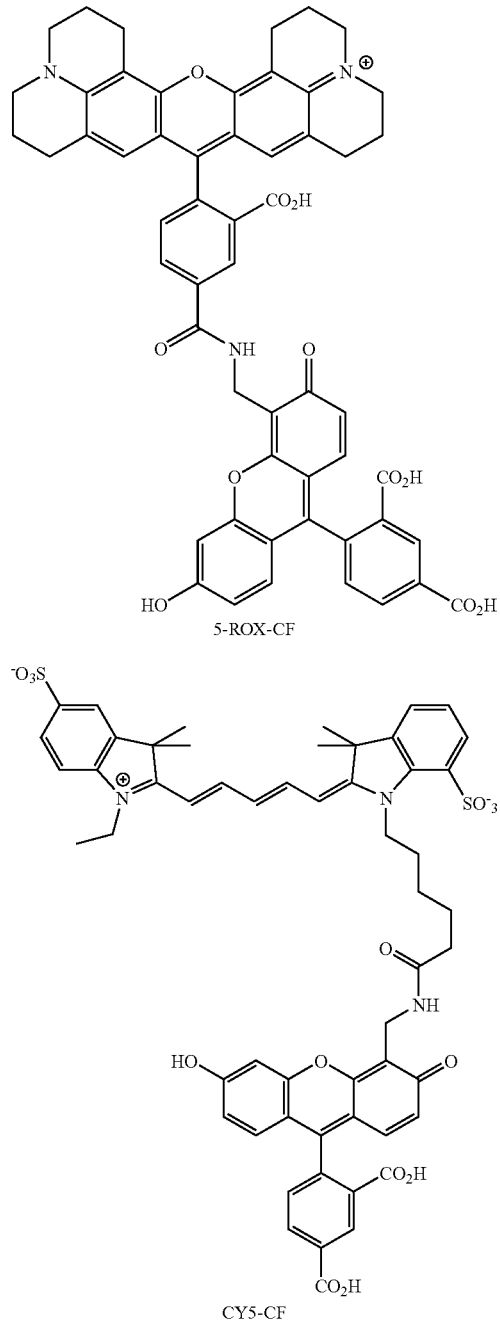

5-ROX-CF

CY5-CF 6.3 Reagents Including Energy Transfer Dyes of the Present Invention

The present invention also relates to fluorescent reagents which incorporate an energy transfer fluorescent dye according to the present invention. As described in greater detail in Section III, these reagents may be used in a wide variety of methods for detecting the presence of a component in a sample.

The fluorescent reagents of the present invention include any molecule or material to which the energy transfer dyes of the invention can be attached and used to detect the presence of the reagent based on the fluorescence of the energy transfer dye. Types of molecules and materials to which the dyes of the present invention may be attached to form a reagent include, but are not limited to proteins, polypeptides, polysaccharides, nucleotides, nucleosides, oligonucleotides, oligonucleotide analogs (such as a peptide nucleic acid), lipids, solid supports, organic and inorganic polymers, and combinations and assemblages thereof, such as chromosomes, nuclei, living cells, such as bacteria, other microorganisms, mammalian cells, and tissues.

Preferred classes of reagents of the present invention are nucleotides, nucleosides, oligonucleotides and oligonucleotide analogs which have been modified to include an energy transfer dye of the invention. Examples of uses for nucleotide and nucleoside reagents include, but are not limited to, labeling oligonucleotides formed by enzymatic synthesis, e.g., nucleoside triphosphates used in the context of PCR amplification, Sanger-type oligonucleotide sequencing, and nick-translation reactions. Examples of uses for oligonucleotide reagents include, but are not limited to, as DNA sequencing primers, PCR primers, oligonucleotide hybridization probes, and the like.

One particular embodiment of the reagents are labeled nucleosides (NTP), such as cytosine, adenosine, guanosine, and thymidine, labeled with an energy transfer fluorescent dye of the present invention. These reagents may be used in a wide variety of methods involving oligonucleotide synthesis. Another related embodiment are labeled nucleotides, e.g., mono-, di- and triphosphate nucleoside phosphate esters. These reagents include, in particular, deoxynucleoside triphosphates (dNTP), such as deoxycytosine triphosphate, deoxyadenosine triphosphate, deoxyguanosine triphosphate, and deoxythymidine triphosphate, labeled with an energy transfer fluorescent dye of the present invention. These reagents may be used, for example, as polymerase substrates in the preparation of dye labeled oligonucleotides. These reagents also include labeled dideoxynucleoside triphosphates (ddNTP), such as dideoxycytosine triphosphate, dideoxyadenosine triphosphate, dideoxyguanosine triphosphate, and dideoxythymidine triphosphate, labeled with an energy transfer fluorescent dye of the present invention. These reagents may be used, for example, in dye termination sequencing.

Another embodiment of reagents are oligonucleotides which includes an energy transfer fluorescent dye of the present invention. These reagents may be used, for example, in dye primer sequencing.

As used herein, "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms, e.g. as described in Kornberg and Baker, DNA Replication, 2nd Ed. (Freeman, San Francisco, 1992). The term "nucleotide" as used herein refers to a phosphate ester of a nucleoside, e.g., mono, di and triphosphate esters, wherein the most common site of esterification is the hydroxyl group attached to the C-5 position of the pentose. "Analogs" in reference to nucleosides include synthetic nucleosides having modified base moieties and/or modified sugar moieties, e.g. described generally by Scheit, Nucleotide Analogs (John Wiley, New York, 1980). The terms "labeled nucleoside" and "labeled nucleotide" refer to nucleosides and nucleotides which are covalently attached to an energy transfer dye through a linkage.

As used herein, the term "oligonucleotide" refers to linear polymers of natural or modified nucleoside monomers, including double and single stranded deoxyribonucleosides, ribonucleosides, α-anomeric forms thereof, and the like. Usually the nucleoside monomers are linked by phosphodiester linkages, where as used herein, the term "phosphodiester linkage" refers to phosphodiester bonds or analogs thereof including phosphorothioate, phosphorodithioate, phosphoroselenoate, phosphorodiselenoate, phosphoroanilothioate, phosphoranilidate, phosphoramidate, and the like, including associated counterions, e.g., H, $NH_4$, Na, and the like if such counterions are present. The oligonucleotides range in size form a few monomeric units, e.g. 8-40, to several thousands of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted.

Nucleoside labeling can be accomplished using any of a large number of known nucleoside labeling techniques using known linkages, linking groups, and associated complementary functionalities. The linkage linking the dye and nucleoside should (i) be stable to oligonucleotide synthesis conditions, (ii) not interfere with oligonucleotide-target hybridization, (iii) be compatible with relevant enzymes, e.g., polymerases, ligases, and the like, and (iv) not quench the fluorescence of the dye.

Preferably, the dyes are covalently linked to the 5-carbon of pyrimidine bases and to the 7-carbon of 7-deazapurine bases. Several suitable base labeling procedures have been reported that can be used with the invention, e.g. Gibson et al, *Nucleic Acids Research*, 15:6455-6467 (1987); Gebeyehu et al, *Nucleic Acids Research*, 15:4513-4535 (1987); Haralambidis et al, *Nucleic Acids Research*, 15:4856-4876 (1987); Nelson et al., *Nucleosides and Nucleotides*, 5(3):233-241 (1986); Bergstrom et al., *JACS*, 111:374-375 (1989); U.S. Pat. Nos. 4,855,225, 5,231,191, and 5,449,767, each of which is incorporated herein by reference.

Preferably, the linkages are acetylenic amido or alkenic amido linkages, the linkage between the dye and the nucleotide base being formed by reacting an activated N-hydroxysuccinimide (NHS) ester of the dye with an alkynylamino-, alkynylethoxyamino- or alkenylamino-derivatized base of a nucleotide. More preferably, the resulting linkage is proargyl-1-ethoxyamido (3-(amino)ethoxy-1-propynyl), 3-(carboxy)amino-1-propynyl or 3-amino-1-propyn-1-yl.

Several preferred linkages for linking the dyes of the invention to a nucleoside base are —C≡C—$CH_2$—NH—C(O)—, 3-amino-1-propyn-1-yl, —C≡C—$CH_2$—NH—C(O)—$(CH_2)_5$—NH—C(O)—, —CH=CH—C(O)—NH—$(CH_2)_5$—NH—C(O)— and —C≡C—$CH_2$—O—$CH_2CH_2NR_1R_2$, where $R_1$ and $R_2$ taken separately are H, alkyl, a protecting group or a fluorescent dye.

The synthesis of alkynylamino-derivatized nucleosides is taught by Hobbs et al. in European Patent Application No. 87305844.0, and Hobbs et al., *J. Org. Chem.*, 54:3420 (1989), which is incorporated herein by reference. Briefly, the alkynylamino-derivatized nucleotides are formed by placing the appropriate halodideoxynucleoside (usually 5-iodopyrimidine and 7-iodo-7-deazapurine dideoxynucleosides as taught by Hobbs et al. (cited above)) and Cu(I) in a flask, flushing with argon to remove air, adding dry DMF, followed by addition of an alkynylamine, triethyl-amine and Pd(0). The reaction mixture can be stirred for several hours, or until thin layer chromatography indicates consumption of the halodideoxynucleoside. When an unprotected alkynylamine is used, the alkynylamino-nucleoside can be isolated by concentrating the reaction mixture and chromatographing on silica gel using an eluting solvent which contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The triphosphates are obtained by standard techniques.

The synthesis of oligonucleotides labeled with an energy transfer dye of the present invention can be accomplished using any of a large number of known oligonucleotide labeling techniques using known linkages, linking groups, and associated complementary functionalities. For example, labeled oligonucleotides may be synthesized enzymatically, e.g., using a DNA polymerase or ligase, e.g., Stryer, *Biochemistry*, Chapter 24, W.H. Freeman and Company (1981), or by chemical synthesis, e.g., by a phosphoramidite method, a phosphite-triester method, and the like, e.g., Gait, *Oligonucleotide Synthesis*, IRL Press (1990). Labels may be introduced during enzymatic synthesis utilizing labeled nucleoside triphosphate monomers, or introduced during chemical synthesis using labeled non-nucleotide or nucleotide phosphoramidites, or may be introduced subsequent to synthesis.

Generally, if the labeled oligonucleotide is made using enzymatic synthesis, the following procedure may be used. A template DNA is denatured and an oligonucleotide primer is annealed to the template DNA. A mixture of deoxynucleoside triphosphates is added to the reaction including dGTP, dATP, dCTP, and dTTP where at least a fraction of one of the deoxynucleotides is labeled with a dye compound of the invention as described above. Next, a polymerase enzyme is added under conditions where the polymerase enzyme is active. A labeled polynucleotide is formed by the incorporation of the labeled deoxynucleotides during polymerase strand synthesis. In an alternative enzymatic synthesis method, two primers are used instead of one, one primer complementary to the + strand and the other complementary to the − strand of the target, the polymerase is a thermostable polymerase, and the reaction temperature is cycled between a denaturation temperature and an extension temperature, thereby exponentially synthesizing a labeled complement to the target sequence by PCR, e.g., *PCR Protocols*, Innis et al. eds., Academic Press (1990).

Generally, if the labeled oligonucleotide is made using a chemical synthesis, it is preferred that a phosphoramidite method be used. Phosphoramidite compounds and the phosphoramidite method of polynucleotide synthesis are preferred in synthesizing oligonucleotides because of the efficient and rapid coupling and the stability of the starting materials. The synthesis is performed with the growing oligonucleotide chain attached to a solid support, so that excess reagents, which are in the liquid phase, can be easily removed by filtration, thereby eliminating the need for purification steps between cycles.

In view of the utility of phosphoramidite reagents in labeling nucleosides and oligonucleotides, the present invention also relates to phosphoramidite compounds which include an energy transfer dye of the present invention.

Detailed descriptions of the chemistry used to form oligonucleotides by the phosphoramidite method are provided in Caruthers et al., U.S. Pat. No. 4,458,066; Caruthers et al., U.S. Pat. No. 4,415,732; Caruthers et al., *Genetic Engineering*, 4:1-17 (1982); *Users Manual Model* 392 *and* 394 *Polynucleotide Synthesizers*, pages 6-1 through 6-22, Applied Biosystems, Part No. 901237 (1991), each of which are incorporated by reference in their entirety.

The following briefly describes the steps of a typical oligonucleotide synthesis cycle using the phosphoramidite method. First, a solid support including a protected nucleotide monomer is treated with acid, e.g., trichloroacetic acid, to remove a 5'-hydroxyl protecting group, freeing the hydroxyl for a subsequent coupling reaction. An activated intermediate is then formed by simultaneously adding a protected phosphoramidite nucleoside monomer and a weak acid, e.g., tetrazole, to the reaction. The weak acid protonates the nitrogen of the phosphoramidite forming a reactive intermediate. Nucleoside addition is complete within 30 s. Next, a capping step is performed which terminates any polynucleotide chains that did not undergo nucleoside addition. Capping is preferably done with acetic anhydride and 1-methylimidazole. The internucleotide linkage is then converted from the phosphite to the more stable phosphotriester by oxidation using iodine as the preferred oxidizing agent and water as the oxygen donor. After oxidation, the hydroxyl protecting group is removed with a protic acid, e.g., trichloroacetic acid or dichloroacetic acid, and the cycle is repeated until chain elongation is complete. After synthesis, the polynucleotide chain is cleaved from the support using a base, e.g., ammonium hydroxide or t-butyl amine. The cleavage reaction also removes any phosphate protecting groups, e.g., cyanoethyl. Finally, the protecting groups on the exocyclic amines of the bases and the hydroxyl protecting groups on the dyes are removed by treating the polynucleotide solution in base at an elevated temperature, e.g., 55° C.

Any of the phosphoramidite nucleoside monomers may be dye-labeled phosphoramidites. If the 5'-terminal position of the nucleotide is labeled, a labeled non-nucleotidic phosphoramidite of the invention may be used during the final condensation step. If an internal position of the oligonucleotide is to be labeled, a labeled nucleotidic phosphoramidite of the invention may be used during any of the condensation steps.

Subsequent to their synthesis, oligonucleotides may be labeled at a number of positions including the 5'-terminus. See *Oligonucleotides and Analogs*, Eckstein ed., Chapter 8, IRL Press (1991) and Orgel et al., *Nucleic Acids Research* 11 (18):6513 (1983); U.S. Pat. No. 5,118,800, each of which are incorporated by reference.

Oligonucleotides may also be labeled on their phosphodiester backbone (*Oligonucleotides and Analogs*, Eckstein ed., Chapter 9) or at the 3'-terminus (Nelson, *Nucleic Acids Research* 20(23):6253-6259, and U.S. Pat. Nos. 5,401,837 and 5,141,813, both patents hereby incorporated by reference. For a review of oligonucleotide labeling procedures see R. Haugland in *Excited States of Biopolymers*, Steiner ed., Plenum Press, NY (1983).

In one preferred post-synthesis chemical labeling method an oligonucleotide is labeled as follows. A dye including a carboxy linking group is converted to the n-hydroxysuccinimide ester by reacting with approximately 1 equivalent of 1,3-dicyclohexylcarbodiimide and approximately 3 equivalents of N-hydroxysuccinimide in dry ethyl acetate for 3 hours at room temperature. The reaction mixture is washed with 5% HCl, dried over magnesium sulfate, filtered, and concentrated to a solid which is resuspended in DMSO. The DMSO dye stock is then added in excess (10-20×) to an aminohexyl derivatized oligonucleotide in 0.25 M bicarbonate/carbonate buffer at pH 9.4 and allowed to react for 6 hours, e.g., U.S. Pat. No. 4,757,141. The dye labeled oligonucleotide is separated from unreacted dye by passage through a size-exclusion chromatography column eluting with buffer, e.g., 0.1 molar triethylamine acetate (TEAA). The fraction containing the crude labeled oligonucleotide is further purified by reverse phase HPLC employing gradient elution.

6.4 Methods Employing Dyes and Reagents of the Present Invention

The energy transfer dyes and reagents of the present invention may be used in a wide variety of methods for detecting the presence of a component in a sample by labeling the component in the sample with a reagent containing the dye. In particular, the energy transfer dyes and reagents of the present invention are well suited for use in methods which combine separation and fluorescent detection techniques, particularly methods requiring the simultaneous detection of multiple spatially-overlapping analytes. For example, the dyes and reagents are particularly well suited for identifying classes of oligonucleotides that have been subjected to a biochemical separation procedure, such as electrophoresis, where a series of bands or spots of target substances having similar physiochemical properties, e.g. size, conformation, charge, hydrophobicity, or the like, are present in a linear or planar arrangement. As used herein, the term "bands" includes any spatial grouping or aggregation of analytes on the basis of similar or identical physiochemical properties. Usually bands arise in the separation of dye-oligonucleotide conjugates by electrophoresis.

Classes of oligonucleotides can arise in a variety of contexts. In a preferred category of methods referred to herein as "fragment analysis" or "genetic analysis" methods, labeled oligonucleotide fragments are generated through template-directed enzymatic synthesis using labeled primers or nucleotides, e.g., by ligation or polymerase-directed primer extension; the fragments are subjected to a size-dependent separation process, e.g., electrophoresis or chromatography; and, the separated fragments are detected subsequent to the separation, e.g., by laser-induced fluorescence. In a particularly preferred embodiment, multiple classes of oligonucleotides are separated simultaneously and the different classes are distinguished by spectrally resolvable labels.

One such fragment analysis method is amplified fragment length polymorphisim detection (AmpFLP) and is based on amplified fragment length polymorphisms, i.e., restriction fragment length polymorphisms that are amplified by PCR. These amplified fragments of varying size serve as linked markers for following mutant genes through families. The closer the amplified fragment is to the mutant gene on the chromosome, the higher the linkage correlation. Because genes for many genetic disorders have not been identified, these linkage markers serve to help evaluate disease risk or paternity. In the AmpFLPs technique, the polynucleotides may be labeled by using a labeled oligonucleotide PCR primer, or by utilizing labeled nucleotide triphosphates in the PCR.

Another fragment analysis method is nick translation. Nick translation involves a reaction to replace unlabeled nucleotide triphosphates in a double-stranded DNA molecule with labeled ones. Free 3'-hydroxyl groups are created within the unlabeled DNA by "nicks" caused by deoxyribonuclease I (DNAase I) treatment. DNA polymerase I then catalyzes the addition of a labeled nucleotide to the 3'-hydroxyl terminus of the nick. At the same time, the 5' to 3'-exonuclease activity of this enzyme eliminates the nucleotide unit from the 5'-phosphoryl terminus of the nick. A new nucleotide with a free 3'-OH group is incorporated at the position of the original excised nucleotide, and the nick is shifted along by one nucleotide unit in the 3' direction. This 3' shift will result in the sequential addition of new labeled nucleotides to the DNA with the removal of existing unlabeled nucleotides. The nick-translated polynucleotide is then analyzed using a separation process, e.g., electrophoresis.

Another exemplary fragment analysis method is based on variable number of tandem repeats, or VNTRs. VNTRs are regions of double-stranded DNA that contain adjacent multiple copies of a particular sequence, with the number of repeating units being variable. Examples of VNTR loci are pYNZ22, pMCT118, and Apo B. A subset of VNTR methods are those methods based on the detection of microsatellite repeats, or short tandem repeats (STRs), i.e., tandem repeats of DNA characterized by a short (2-4 bases) repeated sequence. One of the most abundant interspersed repetitive DNA families in humans is the (dC-dA)n—(dG-dT)n dinucleotide repeat family (also called the (CA)n dinucleotide repeat family). There are thought to be as many as 50,000 to 100,000 (CA)n repeat regions in the human genome, typically with 15-30 repeats per block. Many of these repeat regions are polymorphic in length and can therefore serve as useful genetic markers. Preferably, in VNTR or STR methods, label is introduced into the polynucleotide fragments by using a dye-labeled PCR primer.

Another exemplary fragment analysis method is DNA sequencing. In general, DNA sequencing involves an extension/termination reaction of an oligonucleotide primer. Included in the reaction mixture are deoxynucleoside triphosphates (dNTPs) which are used to extend the primer. Also included in the reaction mixture is at least one dideoxynucleoside triphosphate (ddNTP) which when incorporated onto the extended primer prevents the further extension of the primer. After the extension reaction has been terminated, the different termination products that are formed are separated and analyzed in order to determine the positioning of the different nucleosides.

Fluorescent DNA sequencing may generally be divided into two categories, "dye primer sequencing" and "dye terminator sequencing". In dye primer sequencing, a fluorescent dye is incorporated onto the primer being extended. Four separate extension/termination reactions are then run in parallel, each extension reaction containing a different dideoxynucleoside triphosphate (ddNTP) to terminate the extension reaction. After termination, the reaction products are separated by gel electrophoresis and analyzed. See, for example, Ansorge et al., *Nucleic Acids Res.* 15:4593-4602 (1987).

In one variation of dye primer sequencing, different primers are used in the four separate extension/termination reactions, each primer containing a different spectrally resolvable dye. After termination, the reaction products from the four extension/termination reactions are pooled, electrophoretically separated, and detected in a single lane. See, for example, Smith et al., *Nature* 321:674-679 (1986). Thus, in this variation of dye primer sequencing, by using primers containing a set of spectrally resolvable dyes, products from more than one extension/termination reactions can be simultaneously detected.

In dye terminator sequencing, a fluorescent dye is attached to each of the dideoxynucleoside triphosphates. An extension/termination reaction is then conducted where a primer is extended using deoxynucleoside triphosphates until the labeled dideoxynucleoside triphosphate is incorporated into the extended primer to prevent further extension of the primer. Once terminated, the reaction products for each dideoxynucleoside triphosphate are separated and detected. In one embodiment, separate extension/termination reactions are conducted for each of the four dideoxynucleoside triphosphates. In another embodiment, a single extension/termination reaction is conducted which contains the four dideoxynucleoside triphosphates, each labeled with a different, spectrally resolvable fluorescent dye.

Thus according to one aspect of the invention, a method is provided for conducting dye primer sequencing using one or more oligonucleotide reagents of the present invention. According to this method, a mixture of extended labeled primers are formed by hybridizing a nucleic acid sequence with a fluorescently labeled oligonucleotide primer in the presence of deoxynucleoside triphosphates, at least one dideoxynucleoside triphosphate and a DNA polymerase. The fluorescently labeled oligonucleotide primer includes an oligonucleotide sequence complementary to a portion of the nucleic acid sequence being sequenced, and an energy transfer fluorescent dye attached to the oligonucleotide.

According to the method, the DNA polymerase extends the primer with the deoxynucleoside triphosphates until a dideoxynucleoside triphosphate is incorporated which terminates extension of the primer. After termination, the mixture of extended primers are separated. The sequence of the nucleic acid sequence is then determined by fluorescently detecting the mixture of extended primers formed.

In a further embodiment of this method, four dye primer sequencing reactions are run, each primer sequencing reaction including a different fluorescently labeled oligonucleotide primer and a different dideoxynucleoside triphosphate (ddATP, ddCTP, ddGTP and ddTTP). After the four dye primer sequencing reactions are run, the resulting mixtures of extended primers may be pooled. The mixture of extended primers may then be separated, for example by electrophoresis and the fluorescent signal from each of the four different fluorescently labeled oligonucleotide primers detected in order to determine the sequence of the nucleic acid sequence.

According to a further aspect of the invention, a method is provided for conducting dye terminator sequencing using one or more dideoxynucleoside triphosphates labeled with an energy transfer dye of the present invention. According to this method, a mixture of extended primers are formed by hybridizing a nucleic acid sequence with an oligonucleotide primer in the presence of deoxynucleoside triphosphates, at least one fluorescently labeled dideoxynucleotide triphosphate and a DNA polymerase. The fluorescently labeled dideoxynucleotide triphosphate includes a dideoxynucleoside triphosphate labeled with an energy transfer fluorescent dye of the present invention.

According to this method, the DNA polymerase extends the primer with the deoxynucleoside triphosphates until a fluorescently labeled dideoxynucleoside triphosphate is incorporated into the extended primer. After termination, the mixture of extended primers are separated. The sequence of the nucleic acid sequence is then determined by detecting the fluorescently labeled dideoxynucleoside attached to the extended primer.

In a further embodiment of this method, the step of forming a mixture of extended primers includes hybridizing the nucleic acid sequence with four different fluorescently labeled dideoxynucleoside triphosphates, i.e., a fluorescently labeled dideoxycytosine triphosphate, a fluorescently labeled dideoxyadenosine triphosphate, a fluorescently labeled dideoxyguanosine triphosphate, and a fluorescently labeled dideoxythymidine triphosphate.

In each of the above-described fragment analysis methods, the labeled oligonucleotides are preferably separated by electrophoretic procedures, e.g. Gould and Matthews, cited above; Rickwood and Hames, Eds., *Gel Electrophoresis of Nucleic Acids: A Practical Approach*, (IRL Press Limited, London, 1981); or Osterman, *Methods of Protein and Nucleic Acid Research*, Vol. 1 Springer-Verlag, Berlin, 1984). Preferably the type of electrophoretic matrix is crosslinked or uncrosslinked polyacrylamide having a concentration (weight to volume) of between about 2-20 weight percent. More preferably, the polyacrylamide concentration is between about 4-8 percent. Preferably in the context of DNA sequencing in particular, the electrophoresis matrix includes a strand separating, or denaturing, agent, e.g., urea, formamide, and the like. Detailed procedures for constructing such matrices are given by Maniatis et al., "Fractionation of Low Molecular Weight DNA and RNA in Polyacrylamide Gels Containing 98% Formamide or 7 M Urea," in *Methods in Enzymology*, 65:299-305 (1980); Maniatis et al., "Chain Length Determination of Small Double- and Single-Stranded DNA Molecules by Polyacrylamide Gel Electrophoresis," *Biochemistry*, 14:3787-3794 (1975); Maniatis et al., *Molecular Cloning: A Laboratory Manual* (Cold Spring Harbor Laboratory, New York, 1982), pgs. 179-185; and *ABI PRISM*™ *377 DNA Sequencer User's Manual, Rev. A*, January 1995, Chapter 2 (p/n 903433, The Perkin-Elmer Corporation, Foster City, Calif.), each of which are incorporated by reference. The optimal polymer concentration, pH, temperature, concentration of denaturing agent, etc. employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations. By way of example, oligonucleotides having sizes in the range of between about 20-300 bases have been separated and detected in accordance with the invention in the following matrix: 6 percent polyacrylamide made from 19 parts to 1 part acrylamide to bis-acrylamide, formed in a Tris-borate EDTA buffer at pH 8.3.

After electrophoretic separation, the dye-oligonucleotide conjugates are detected by measuring the fluorescence emission from the dye labeled polynucleotides. To perform such detection, the labeled polynucleotides are illuminated by standard means, e.g. high intensity mercury vapor lamps, lasers, or the like. Preferably the illumination means is a laser having an illumination beam at a wavelength between 488 and 550 nm. More preferably, the dye-polynucleotides are illuminated by laser light generated by an argon ion laser, particularly the 488 and 514 nm emission lines of an argon ion laser, or an the 532 emission line of a neodymium solid-state YAG laser. Several argon ion lasers are available commercially which lase simultaneously at these lines, e.g. Cyonics, Ltd. (Sunnyvale, Calif.) Model 2001, or the like. The fluorescence is then detected by a light-sensitive detector, e.g., a photomultiplier tube, a charged coupled device, or the like.

6.5 Kits Incorporating the Energy Transfer Dyes

The present invention also relates to kits having combinations of energy transfer fluorescent dyes and/or reagents. In one embodiment, the kit includes at least two spectrally resolvable energy transfer dyes according to the present invention. In this kit, the energy transfer dyes preferably include the same donor dye so that a single light source is needed to excite the dyes.

In another embodiment, the kit includes dideoxycytosine triphosphate, dideoxyadenosine triphosphate, dideoxyguanosine triphosphate, and dideoxythymidine triphosphate, each dideoxynucleotide triphosphate labeled with an energy transfer dye according to the present invention. In one embodiment, each energy transfer dye is spectrally resolvable from the other energy transfer dyes attached to the other dideoxynucleotide triphosphates. In this kit, the energy transfer dyes preferably include the same first xanthene dye.

In yet another embodiment, the kit includes at least two oligonucleotides, each oligonucleotide including an energy transfer dye according to the present invention. In one embodiment, each oligonucleotide contains an energy transfer dye which is spectrally resolvable from the energy transfer dyes attached to the other oligonucleotides. In another embodiment, the kit includes at least four oligonucleotides which each contain a spectrally resolvable energy transfer dye.

7. EXAMPLES

The energy transfer fluorescent dyes and their use in DNA sequencing is illustrated by the following examples. Further objectives and advantages other than those set forth above will become apparent from the examples.

Example 1

Synthesis of 5TMR-B-CF

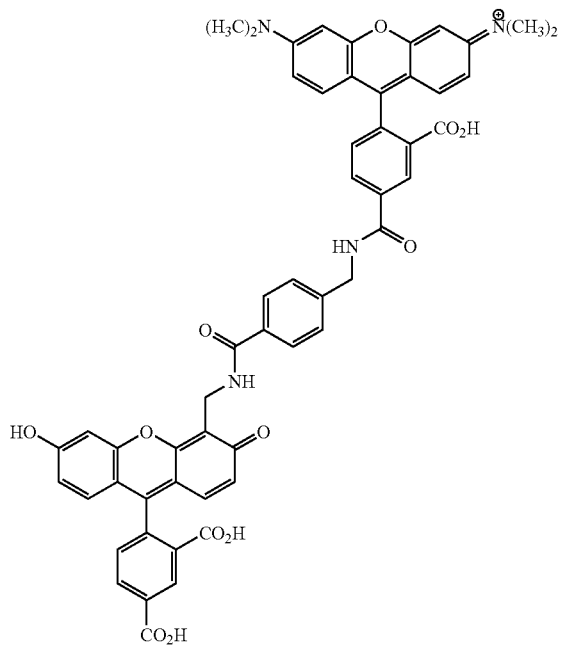

5TMR-B-CF was synthesized from 5-TMR NHS and 4'-aminomethyl-5-carboxyfluorescein according to the reaction sequences described in Examples 1A-C. 5TMR-B-CF was then converted to 5TMR-B-CF-NHS according to the reaction sequence described in 1D so that the dye could be coupled to a nucleoside, nucleotide or oligonucleotide primer.

Example 1A

Synthesis of 5-TMR-B

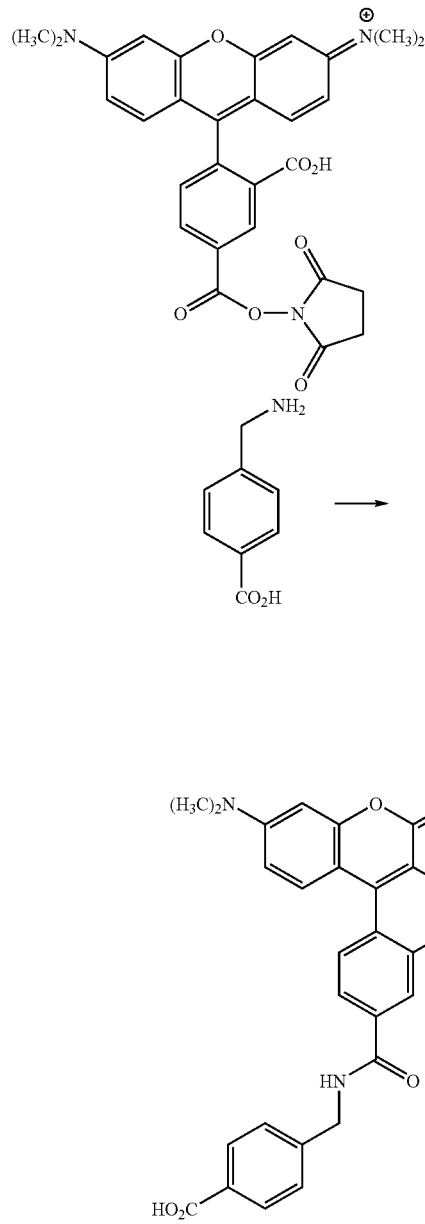

A mixture of 4-aminomethylbenzoic acid (3 mg, 19 µmol), 5-TMR NHS (5 mg, 9 µmol) and triethylamine (20 µL) was suspended in dimethylformamide (DMF, 200 µL) in a 1.5-mL eppendorf tube. The mixture was heated to 60° C. for 10 minutes. Reaction progress was monitored by thin layer chromatography (TLC) on silica gel with elution with a 400/30/10 mixture of dichloromethane, methanol and acetic acid. The insoluble 4-aminomethylbenzoic acid was separated by centrifugation and the DMF solution was decanted into 5% HCl (1 mL). The insoluble 5TMR-B was separated by centrifugation, washed with 5% HCl (2×1 mL) and dried in a vacuum centrifuge. The product was dissolved in DMF (200 µL) and used to prepare 5TMR-B-NHS.

Example 1B

Synthesis of 5-TMR-B-NHS

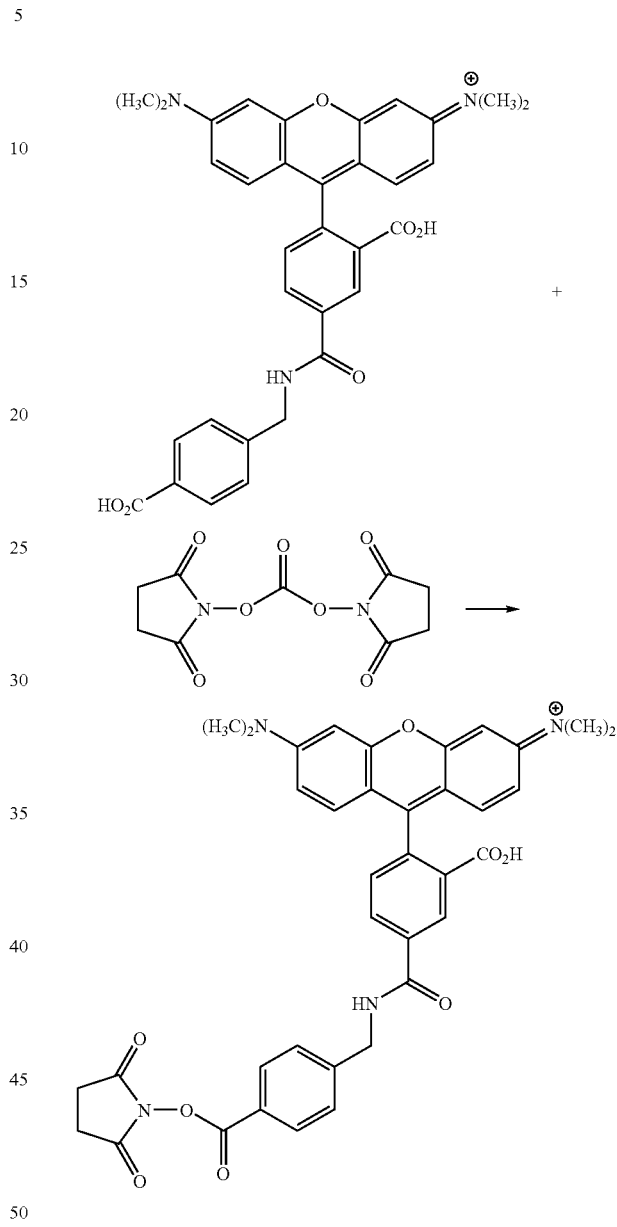

A solution of 5TMR-B in DMF (125 µL), diisopropylethylamine (10 µL) and disuccinimidylcarbonate (10 mg) was combined in a 1.5-mL eppendorf tube and heated to 60° C. The reaction progress was monitored by TLC on silica gel with elution with a 600/60/16 mixture of dichloromethane, methanol and acetic acid. After five minutes, the reaction appeared to be complete. The solution was diluted into methylene chloride (3 mL) and washed with 250 mM carbonate/bicarbonate buffer (pH 9, 4×1 mL), dried ($Na_2SO_4$) and concentrated to dryness on a vacuum centrifuge. The solid was dissolved in DMF (100 µL). The yield was determined by diluting an aliquot into pH 9 buffer and measuring the absorbance at 552 nm. Using an extinction coefficient of 50,000 $cm^{-1} M^{-1}$, the concentration of 5TMR-B-NHS was 4.8 mM. Yield from 5TMR NHS was 8%.

Example 1C

Synthesis of 5TMR-B-CF

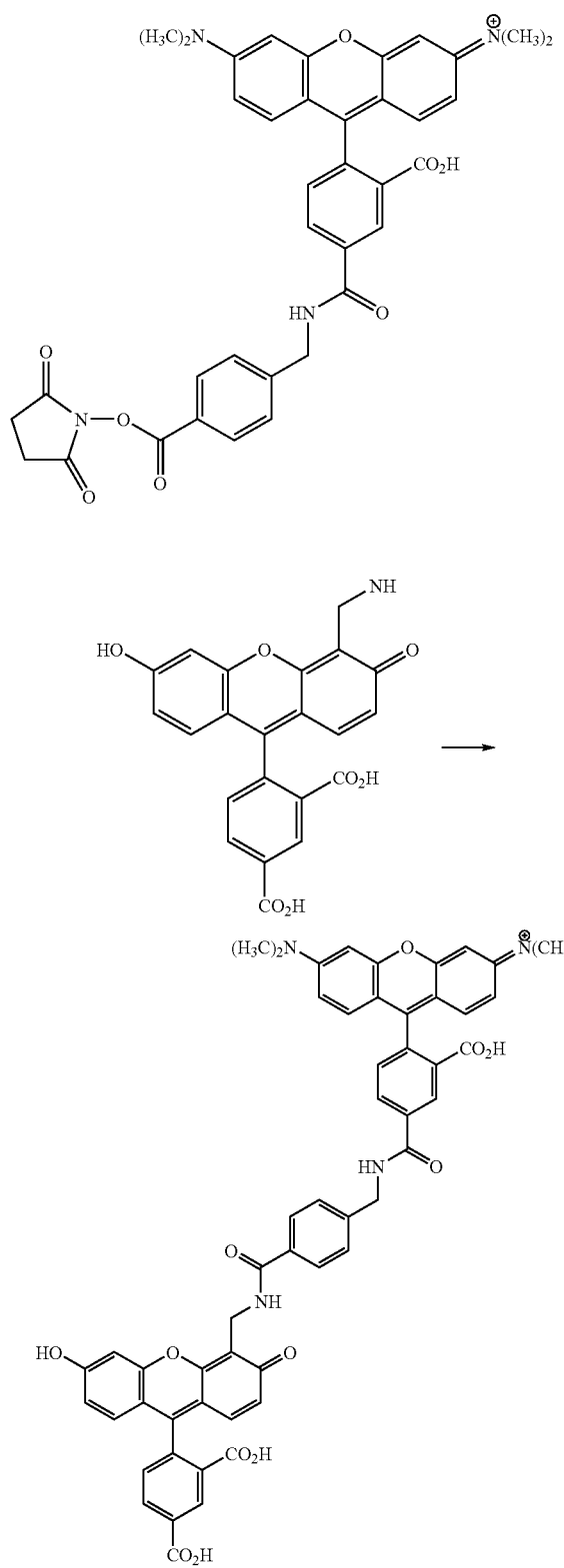

A solution of 5TMR-B-NHS (1 μmol in 250 μL DMF) was combined with a solution of 4'-aminomethyl-5-carboxyfluorescein (CF, 2.2 μmol in 100 μL DMSO) and triethylamine (20 μL) in a 1.5-mL eppendorf tube. The reaction was monitored by HPLC using a C8 reverse-phase column with a gradient elution of 15% to 35% acetonitrile vs. 0.1 M triethylammonium acetate. HPLC analysis indicated the 5TMR-B-NHS was consumed, leaving the excess, unreacted CF. The reaction was diluted with 5% HCl (1 mL) and the product separated by centrifugation, leaving the unreacted CF in the aqueous phase. The solid was washed with 5% HCl (4×1 mL), dried in a vacuum centrifuge and taken up in DMF (300 μL). The yield was quantitative.

Example 1D

Synthesis of 5-TMR-B-CF-NHS

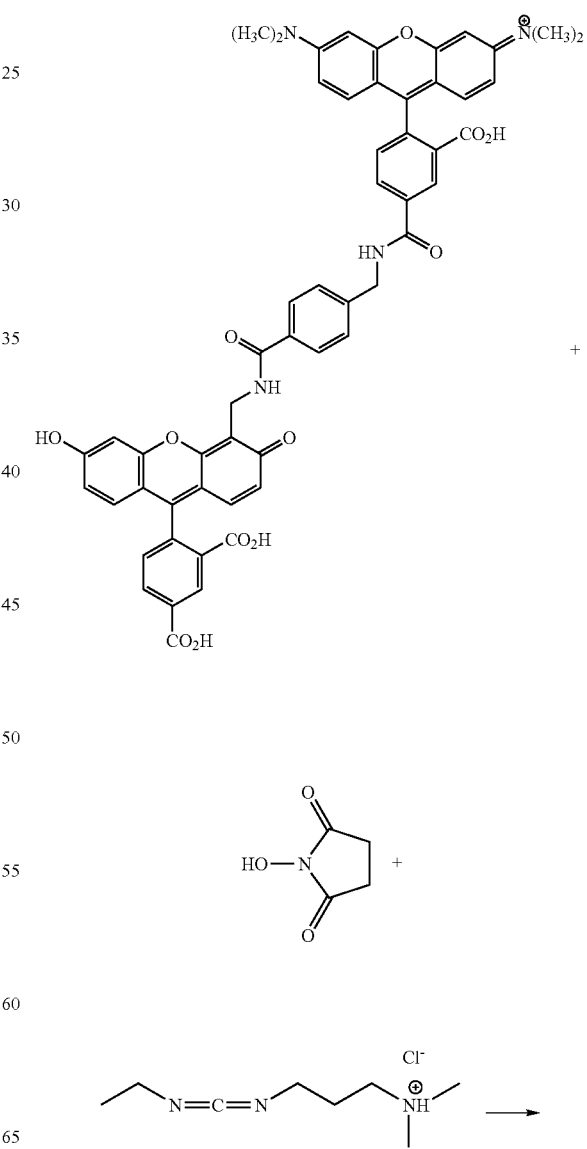

-continued

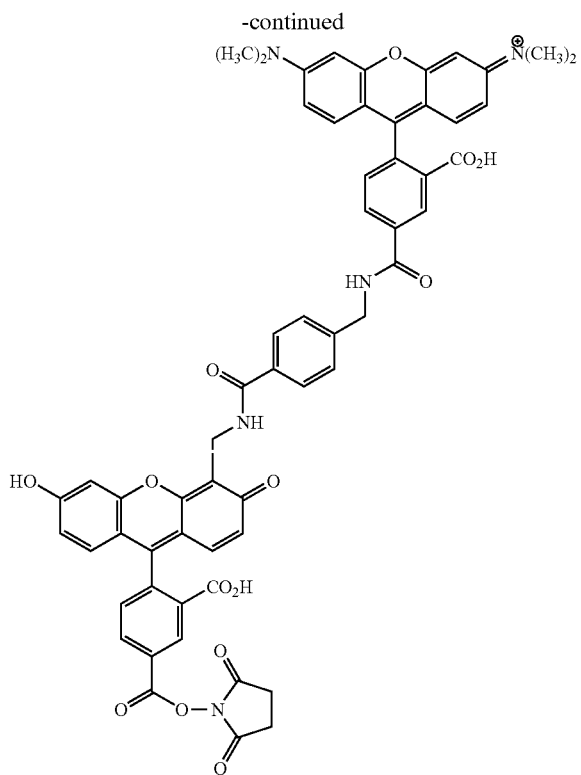

A solution of 5TMR-B-CF (0.6 µmol in 100 µL DMF), 1-(3-dimethylaminopropyl)-3-ethylcarbodiimide hydrochloride (DEC, 2 mg) and N-hydroxysuccinimide (4 mg) were combined in a 1.5-mL eppendorf tube. The mixture was sonicated briefly and heated to 60° C. The reaction was monitored by TLC on silica gel with elution with a 600/60/16 mixture of dichloromethane, methanol and acetic acid. The reaction was complete in 30 minutes and diluted with 5% HCl. The product was separated by centrifugation and dried in a vacuum centrifuge. The activated dye was dissolved in DMF (20 µL).

Example 2

Synthesis of 5ROX-CF

-continued

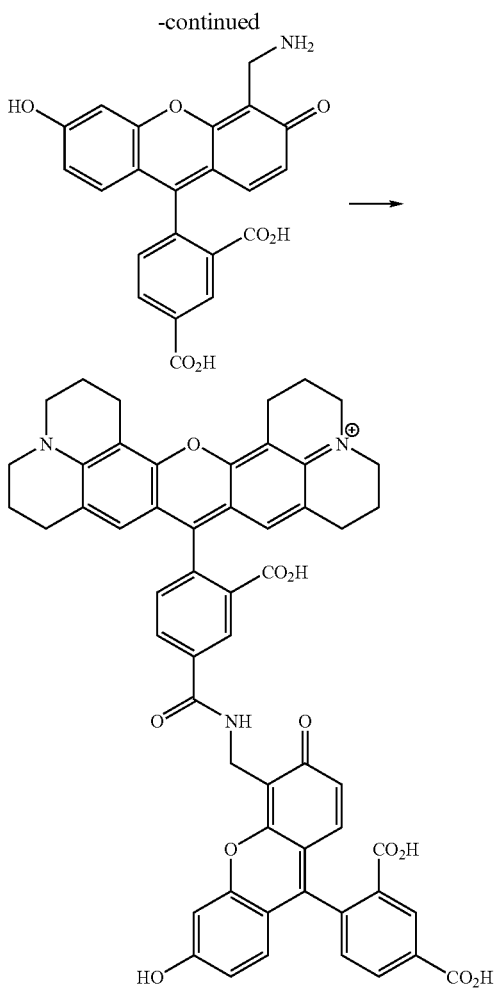

A solution of 5ROX NHS (2 µmol in 100 µL DMSO) was mixed with CF (2 µmol in 100 µL DMSO) and triethylamine (10 µL). The reaction was followed by HPLC on a C8 reverse phase column using a gradient elution of 20% to 40% acetonitrile vs. 0.1 M TEAA. The reaction was diluted into 5% HCl (1 mL) and the product collected by centrifugation, washed with 5% HCl (1×1 mL) and dried in a vacuum centrifuge. The product was taken up in DMF (200 µL).

Example 3

Synthesis of Cy5-CF

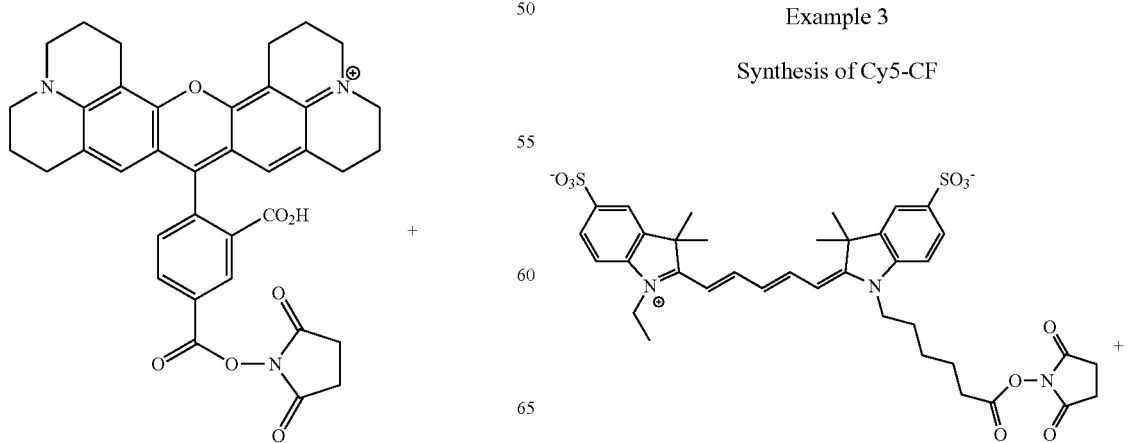

-continued

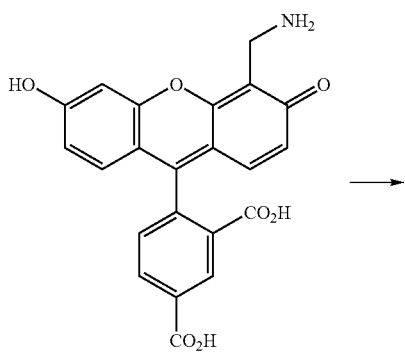

A solution of CF (0.4 μmol in 20 μL CMSO) and triethylamine (2 μL) was added to monoCy5 NHS (approximately 0.3 μmol). The reaction was followed by HPLC on a C8 reverse phase column using a gradient elution of 10% to 30% acetonitrile vs. 0.1 M TEAA. The reaction was diluted into 5% HCl (1 mL) and the product collected by centrifugation, washed with 5% HCl (1×1 mL) and dried in a vacuum centrifuge. The product was taken up in DMF (100 μL).

Example 4

Comparison of Fluorescence Strength of Energy Transfer Dyes

The following example compares the fluorescence emission strength of a series of energy transfer dyes according to the present invention. Dye solutions of 5TMR, 6TMR-CF, 5TMR-gly-CF, 5TMR-CF, 5TMR-B-CF, 5TMR-gly-5AMF, 5TMR-5AMF and 5TMR-lys-5FAM were measured in 1×TBE/8M urea. Each dye solution had an optical density of 0.1 at 560 nm and was excited at 488 nm.

TABLE 7

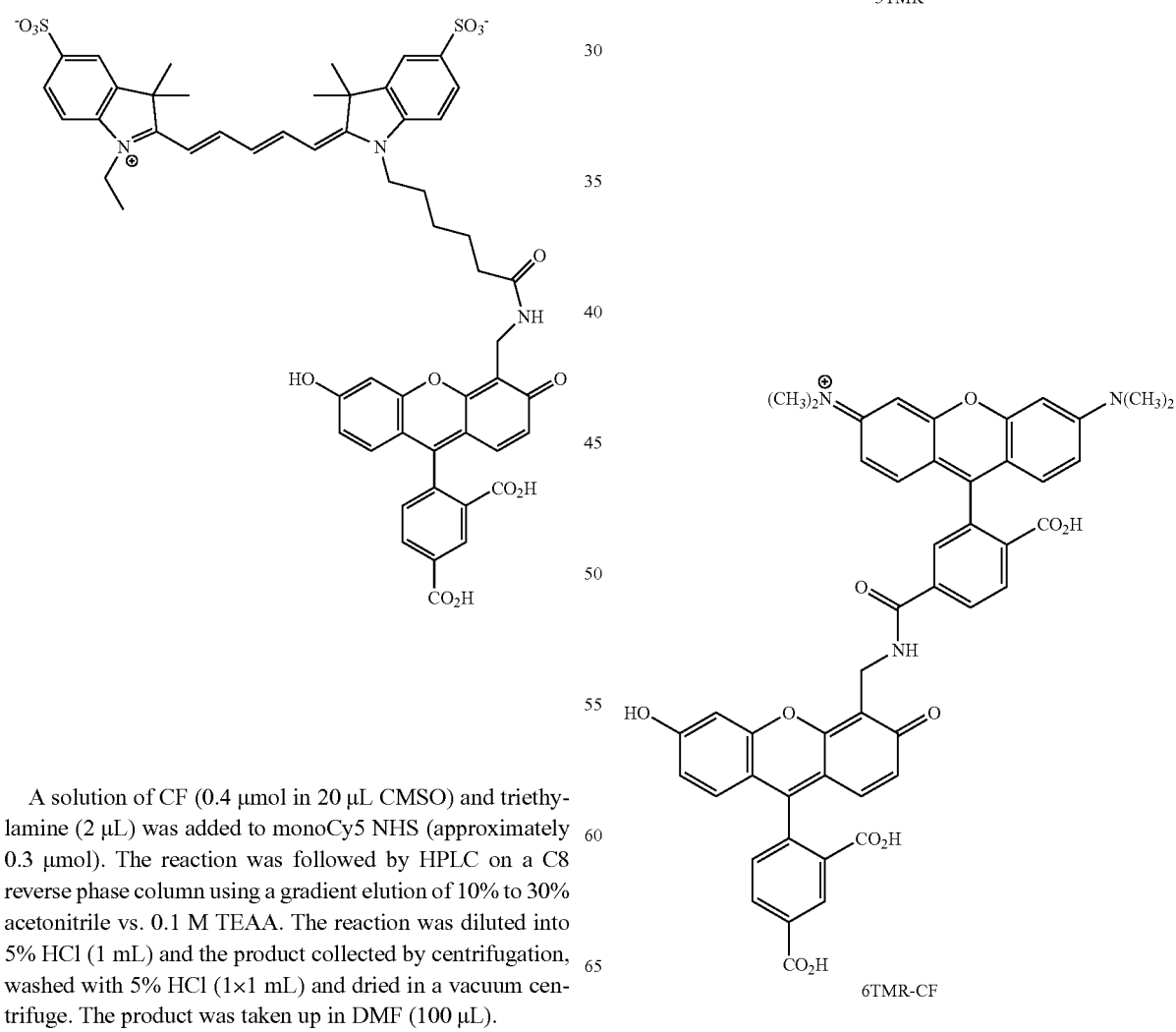

TABLE 7-continued
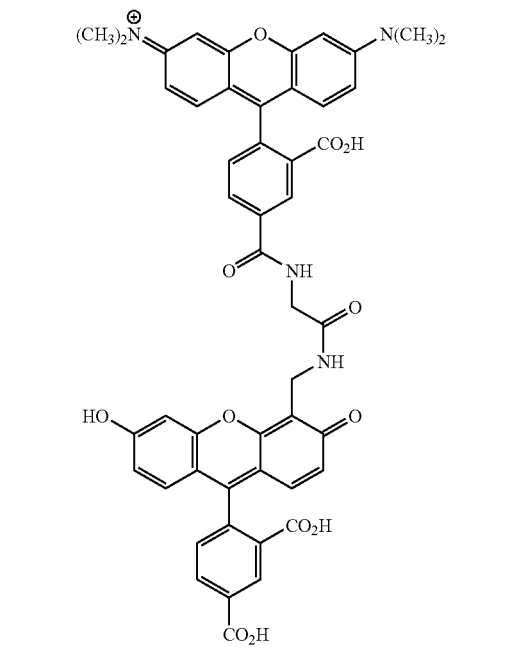
5TMR-gly-CF
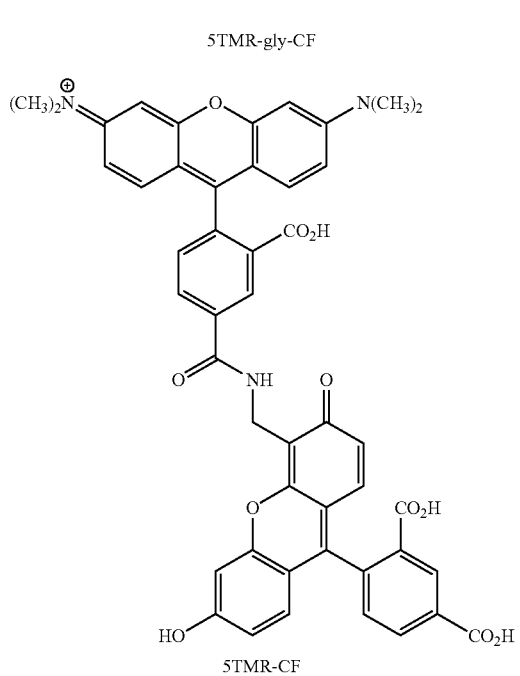
5TMR-CF
TABLE 7-continued
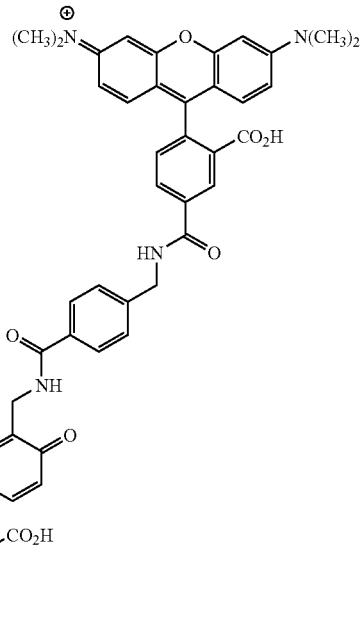
5-TMR-B-CF
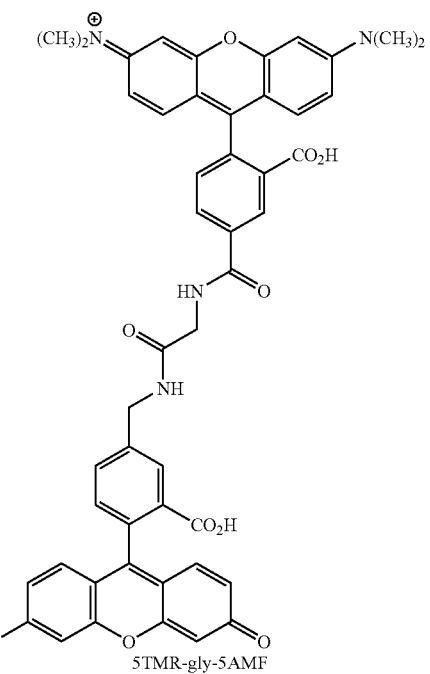
5TMR-gly-5AMF

TABLE 7-continued

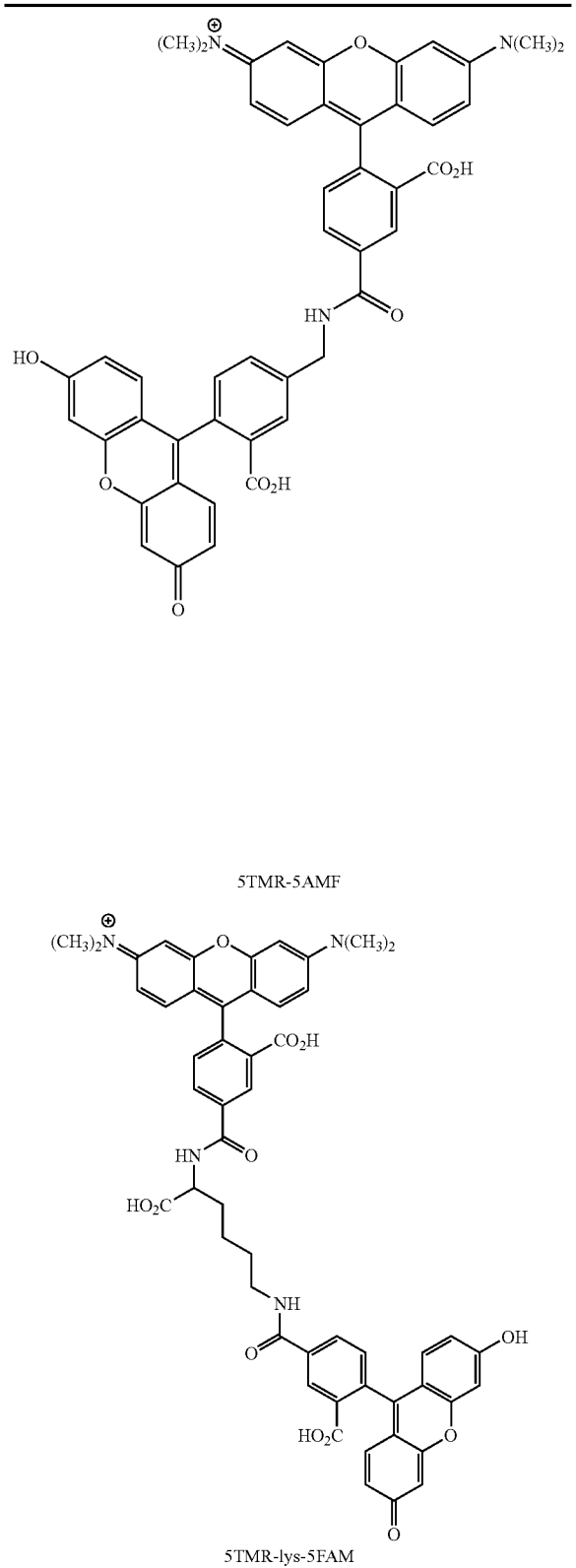

5TMR-5AMF

5TMR-lys-5FAM

The structures of each of these dyes is illustrated in Table 7. FIG. 2 provides a bar graph of the relative fluorescence of each of these dyes.

As can be seen from FIG. 2, energy transfer dyes where the linker is attached to the acceptor at the 5 ring position (5TMR-CF and 5-TMR-B-CF were found to exhibit significantly stronger fluorescence than the acceptor dye itself or when the acceptor dye is linked at the 6 ring position (6TMR-CF). As also can be seen from FIG. 2, energy transfer dyes where the linker has the formula $R_1XC(O)R_2$ where $R_2$ is benzene (5TMR-B-CF) were found to have significantly enhanced fluorescence as compared to the dye where the linker has the formula —CH$_2$NHCO— (5TMR-CF) or —CH$_2$NHCOCH$_2$NHCO— (5TMR-gly-5AMF).

As can also be seen from FIG. 2, energy transfer dyes where the linker is attached to both the donor and acceptor at the 5 ring position (5TMR-5AMF and 5TMR-gly-5AMF) were found to have significant fluorescence. Interestingly, the use of a lysine linker was found not to result in appreciable energy transfer between the donor and acceptor.

Example 5

Dye Primer Sequencing Using Energy Transfer Dye

Figure 7:
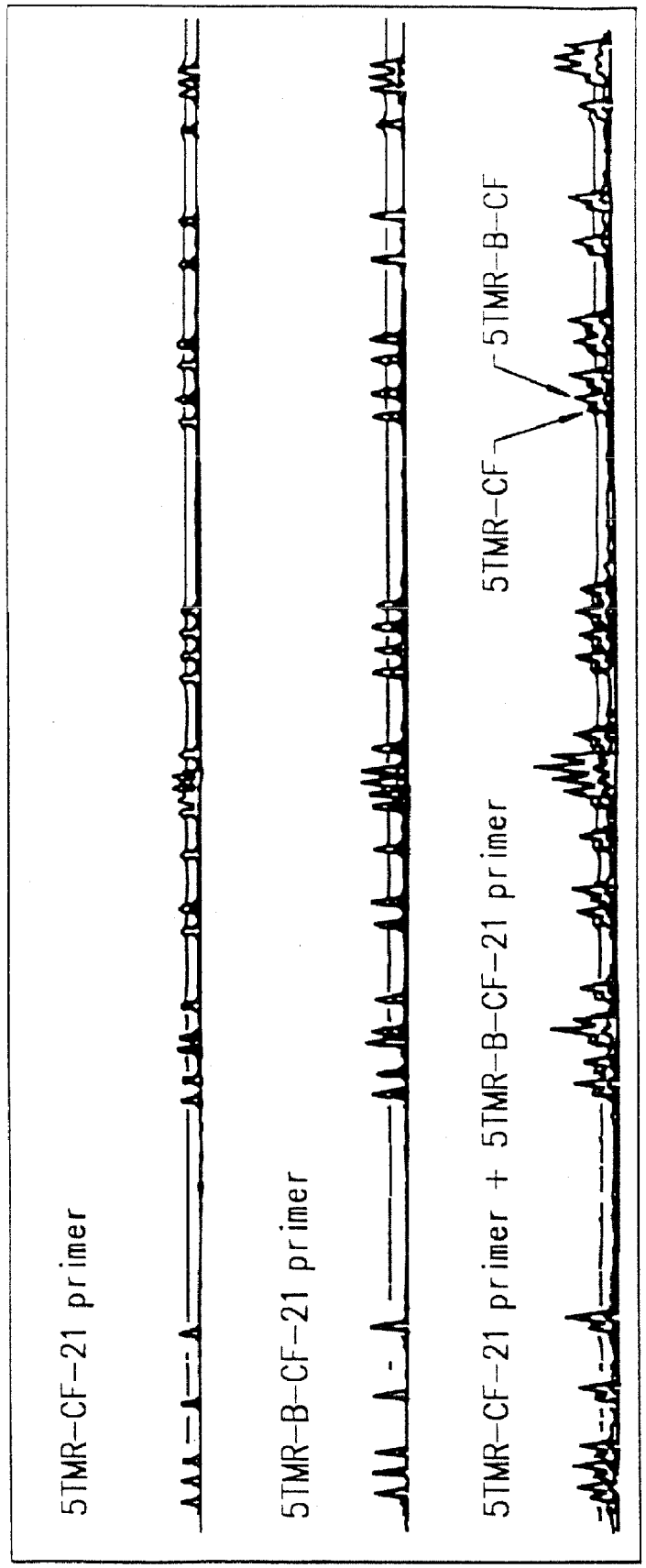
FIG. 7 is a plot of a mixture of labeled oligonucleotides generated during dye primer sequencing using 5TMR-CF and 5TMR-B-CF labeled primers.

In this example, dye primer sequencing was performed on M13 (SEQ. ID. NO.: 1) in order to compare the relative brightness of 5TMR-CF and 5TMR-B-CF labeled oligonucleotides. In this example, dye primer sequencing was performed according to the *ABI PRISM™ 377 DNA Sequencer User's Manual, Rev. B*, January 1995, Chapter 2 (p/n 402114, The Perkin-Elmer Corporation, Foster City, Calif.). 5TMR-CF and 5TMR-B-CF were each attached to the 5' end of M13-21 primer (SEQ. ID. NO.:2). Equimolar solutions of each primer were mixed with the M13 (SEQ. ID. NO.: 1) and sequenced with a single dideoxy nucleotide mixture (ddA/dNTP) and Taq FS. A plot of the resulting mixture of oligonucleotides that were detected using 5TMR-CF and 5TMR-B-CF labeled primers is presented in FIG. 7. As can be seen from FIG. 7, oligonucleotides labeled with 5TMR-B-CF are brighter than oligonucleotides labeled with 5TMR-CF. As can also be seen from FIG. 7, the mobility of oligonucleotides labeled with 5TMR-B-CF are about one nucleotide slower than the oligonucleotides labeled with 5TMR-CF.

Example 6

Dye Primer Sequencing Using Four Dyes

Figure 8:
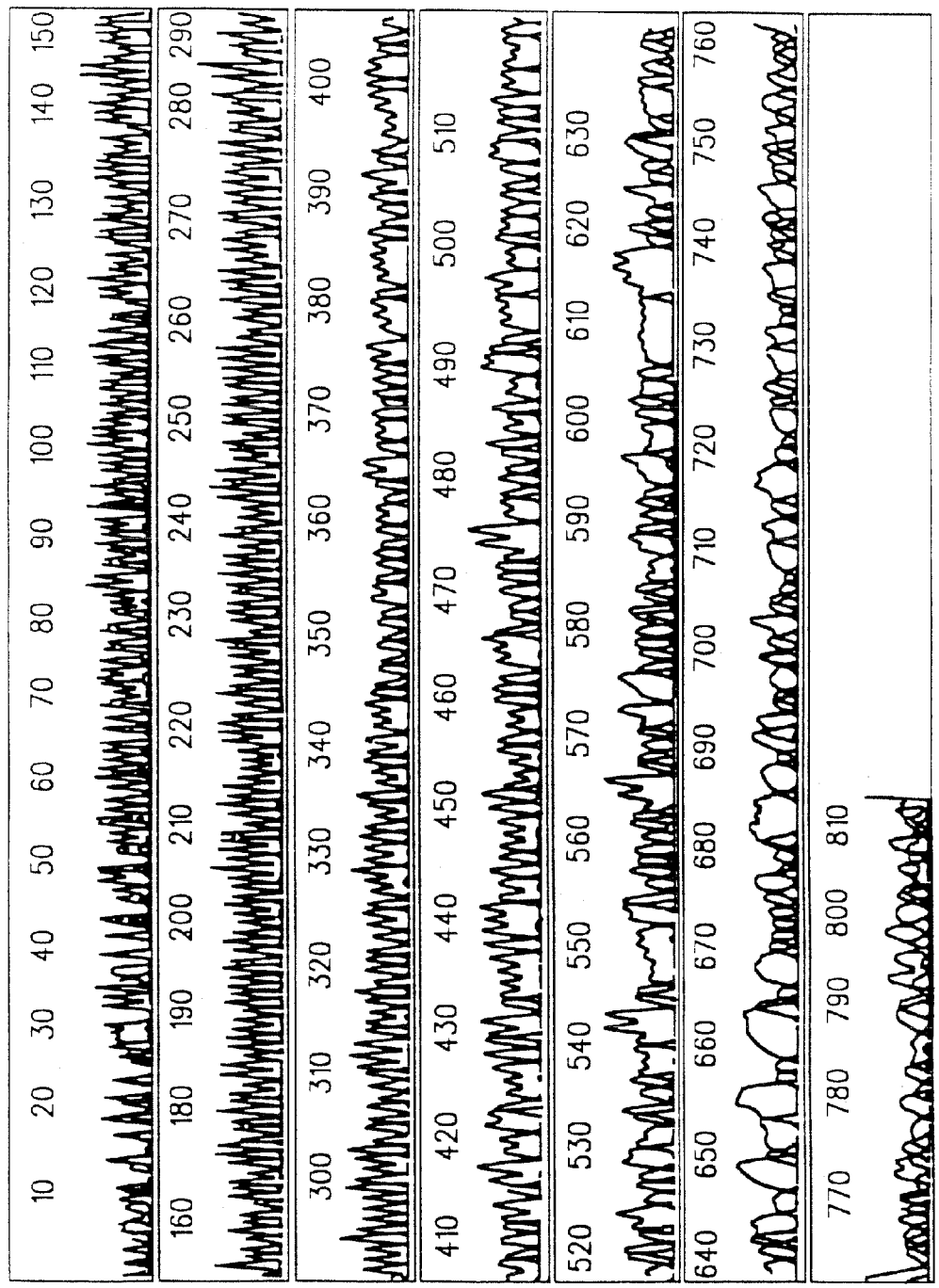
FIG. 8 is a four color plot of dye primer sequencing using a four dye set including 3-carboxy-R110, 5-carboxy-R6G, 5TMR-CF and 5TMR-B-CF.

Dye primer sequencing was performed on the M13 (SEQ ID NO: 1) using a set of four dyes attached to the M13-21 primer (SEQ ID NO: 2) as described in Example 5. FIG. 8 is a four color plot of the dye labeled oligonucleotides produced from the sequencing. The peak for cytosine corresponds to the fluorescence of 5-carboxy-R110. The peak for adenosine corresponds to the fluorescence of 5-carboxy-R6G. The peak for guanosine corresponds to the fluorescence of TMR-B-CF. The peak for thymidine corresponds to the fluorescence of ROX-CF.

As can be seen from FIG. 8, each of the dye labeled oligonucleotides exhibit significant fluorescence intensity. In addition, the different dye labeled oligonucleotides exhibit sufficiently similar mobility so that good resolution of the series of peaks is achieved.

Example 7

Synthesis of 6-CFB-DTMR-2-NHS

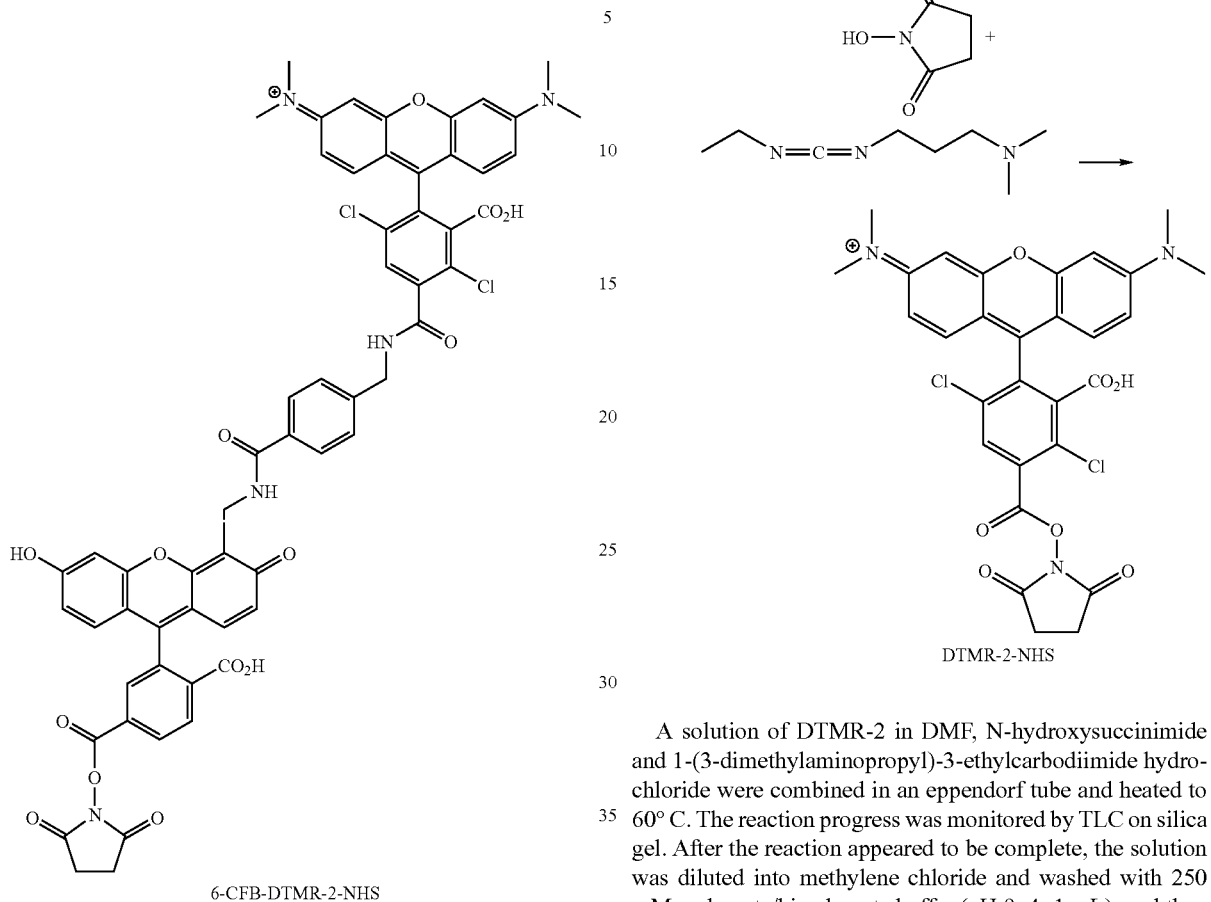

6-CFB-DTMR-2-NHS

6-CFB-DTMR-2 was synthesized from DTMR-2 and 6-CFB according to the reaction sequences described in Examples 1A-B. 6-CFB-DTMR-2 was then converted to 6-CFB-DTMR-2-NHS according to the reaction sequence described in 1C so that the dye could be coupled to a nucleoside, nucleotide or oligonucleotide primer.

Example 7A

Synthesis of DTMR-2-NHS

A solution of DTMR-2 in DMF, N-hydroxysuccinimide and 1-(3-dimethylaminopropyl)-3-ethylcarbodiimide hydrochloride were combined in an eppendorf tube and heated to 60° C. The reaction progress was monitored by TLC on silica gel. After the reaction appeared to be complete, the solution was diluted into methylene chloride and washed with 250 mM carbonate/bicarbonate buffer (pH 9, 4×1 mL), and then with an HCl solution (5%, 1×1 mL), dried ($Na_2SO_4$) and concentrated to dryness on a vacuum centrifuge.

Example 7B

Synthesis of 6-CF-B-DTMR-2

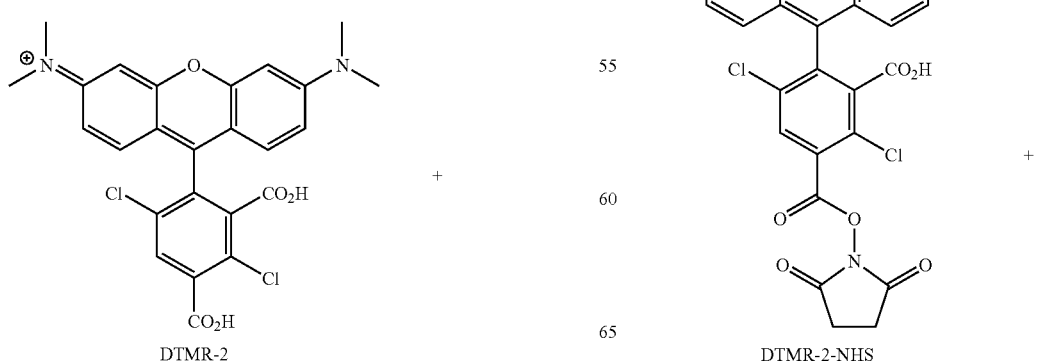

-continued

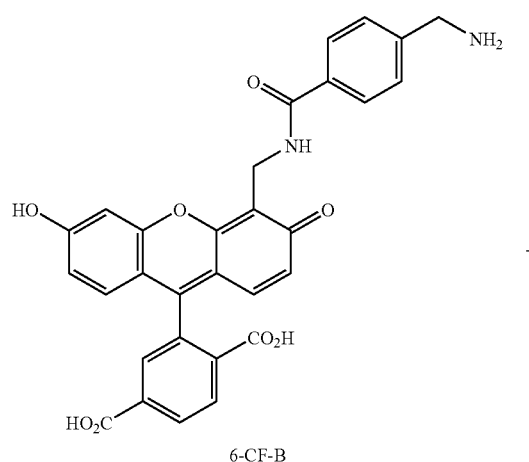
6-CF-B

A solution of 6-CFB in dimethylsulfoxide (100 μL, 11 mM) was combined with a solution of DTMR-2 succidimidyl ester in dimethylformamide (100 μL 22 mM) and triethylamine (20 μL). The reaction was added to a solution of hydrochloric acid (5%, 1 mL) and the solid separated by centrifugation. The red solid was dissolved in carbonate/bicarbonate buffer (250 mM, pH 9, 100 μL) and reprecipitated with dilute HCl. The solid was dried in a vacuum centrifuge and dissolved in dimethylformamide (200 μL). The concentration of the dye solution was determined by diluting an aliquot into 40% acetonitrile/0.1 M triethylammonium acetate buffer (pH 7). Assuming an extinction coefficient of 80,000 $cm^{-1}$ $m^{-1}$ for fluorescein, the 6-CF-B-DTMR-2 solution was found to be 4 mM (70% yield).

Example 7C

Synthesis of 6-CF-B-DTMR-NHS

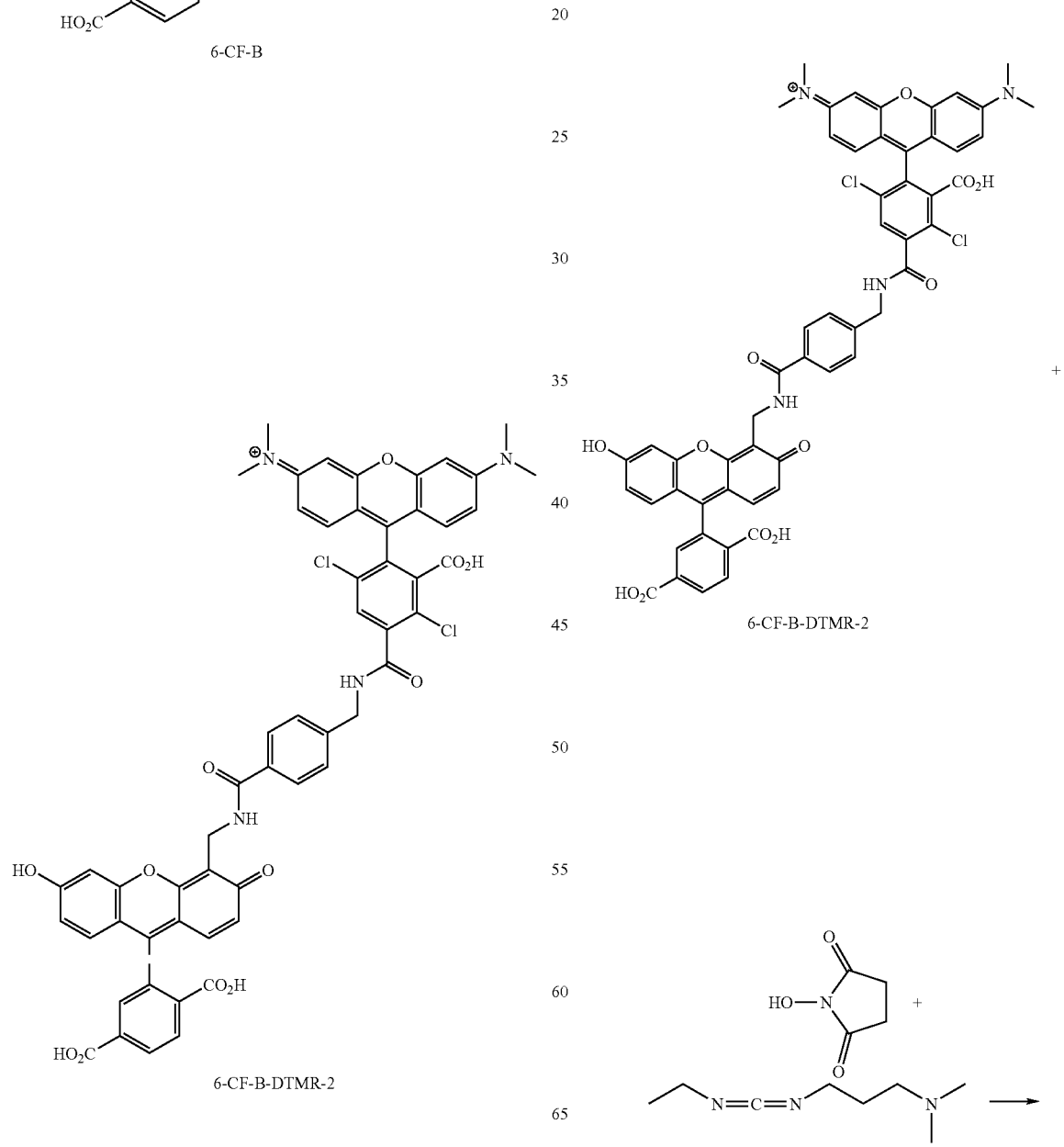

-continued

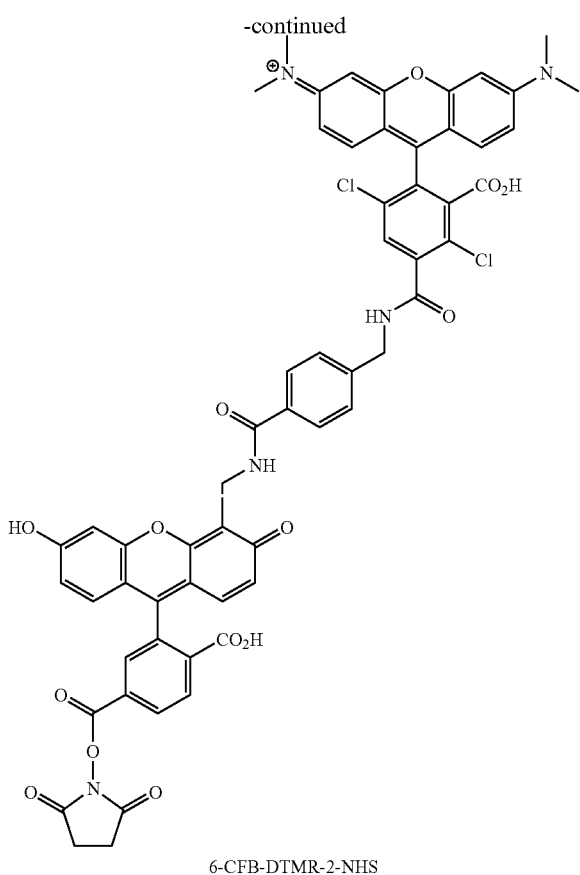

6-CFB-DTMR-2-NHS

A solution of 6-CF-B-DTMR-2 in dimethylformamide (200 µL, 4 mM) was added N-hydroxysuccinimide (10 mg) and 1-(3-dimethylaminopropyl)-3-ethylcarbodiimide hydrochloride (5 µg). Additional N-hydroxysuccinimide (10 mg) was added. The reaction progress was monitored by thin-layer chromatography on silica gel with elution with dichloromethane:methanol:acetic acid in a 600:60:16 mixture. When the reaction was complete, dilute HCl (5%, 1 mL) was added and the product separated by centrifugation. The solid was dried in a vacuum centrifuge and dissolved in dimethylformamide (100 µL). The concentration of the dye solution was determined by diluting an aliquot into 40% acetonitrile/0.1 M triethylammonium acetate buffer (pH 7). Assuming an extinction coefficient of 80,000 $cm^{-1}$ $m^{-1}$ for fluorescein, the 6-CF-B-DTMR-NHS solution was found to be 5.4 mM (68% yield).

Example 8

Comparison of Fluorescence Strength of Dyes

The following example compares the fluorescence emission strength of a series of energy transfer dyes according to the present invention to the corresponding acceptor dye. According to this example, each dye was attached to a 21 primer sequence (5'-TGTAAAACGACGGCCAGT) (SEQ ID NO: 1) with an aminohexyl linkage at the 5' end. The oligonucleotides were quantitated based on the absorbance at 260 nm, assuming an extinction coefficient of 180,000 $cm^{-1}$ $M^{-1}$. Spectra were obtained at a primer concentration of 0.4 µM in 8M urea, 1× Tris/Borate/EDTA (TBE) buffer with 488 nm excitation. FIG. 9A provides the overlaid spectra of 5-CFB-DR110-2 and DR110-2. FIG. 9B provides the overlaid spectra of 5-CFB-DR6G-2 and DR6G-2. FIG. 9C provides the overlaid spectra of 6-CFB-DTMR-2 and DTMR-2. FIG. 9D provides the overlaid spectra of 6-CFB-DROX-2 and DROX-2.

The structures of each of these dyes is illustrated in Table 1. As can be seen from FIGS. 9A-D, energy transfer dyes were found to exhibit significantly stronger fluorescence than the acceptor dye itself.

FIG. 10 shows the normalized fluorescence emission spectra of four dye-labeled oligonucleotides. Spectra were obtained at a primer concentration of 0.4 µM in 8M urea, 1× Tris/Borate/EDTA (TBE) buffer with 488 nm excitation. The dyes shown in FIG. 10 include 5-CFB-DR110-2,5-CFB-DR6G-2,6-CFB-DTMR-2, and 6-CFB-DROX-2. As can be seen from FIG. 10, all four energy transfer dyes are well resolved relative to each other.

Example 9

Dye Primer Sequencing Using Energy Transfer Dye

In this example, dye primer sequencing was performed on M13 (SEQ ID NO: 2) using 5-CF-TMR-2,5-CF-B-TMR-2, 6-CF-B-DTMR-2 and DTMR-2 labeled primers. In this example, dye primer sequencing was performed according to the *ABI PRISM™ 377 DNA Sequencer User's Manual, Rev. B*, January 1995, Chapter 2 (p/n 402114, The Perkin-Elmer Corporation, Foster City, Calif.). The dye was attached to the 5' end of M13-21 primer (SEQ ID NO:3). Equimolar solutions of each primer were mixed with the M13 (SEQ ID NO: 2) and sequenced with a single dideoxy nucleotide mixture (ddA/dNTP) and Taq FS. Plots of the resulting mixtures of oligonucleotides that were detected using 5-CF-TMR-2 and 5-CF-B-TMR-2 labeled primers are presented in FIG. 11. As can be seen from this figure, 5-CF-B-TMR-2 provides a significantly stronger signal than 5-CF-TMR-2, showing the fluorescence enhancement provided by the linker used in 5-CF-B-TMR-2.

Plots of the resulting mixtures of oligonucleotides that were detected using 6-CF-B-DTMR-2 and DTMR-2 labeled primers are presented in FIG. 12. As can be seen from this figure, 6-CF-B-DTMR-2 provides a significantly stronger signal than DTMR-2, showing the fluorescence enhancement provided by the energy transfer dye.

Example 10

Dye Primer Sequencing Using Four Dyes

Dye primer sequencing was performed on M13 (SEQ ID NO:2) using a set of four dyes attached to the M13-21 primer (SEQ ID NO:3) as described in Example 5. FIG. 13 is a four color plot of the dye labeled oligonucleotides produced from the sequencing. The peak for cytosine corresponds to the fluorescence of 5-CFB-DR110-2. The peak for adenosine corresponds to the fluorescence of 6-CFB-DR6g-2. The peak for guanosine corresponds to the fluorescence of 5-CFB-DTMR-2. The peak for thymidine corresponds to the fluorescence of 5-CFB-DROX-2.

As can be seen from FIG. 13, each of the dye labeled oligonucleotides exhibit significant fluorescence intensity. In addition, the different dye labeled oligonucleotides exhibit sufficiently similar mobility so that good resolution of the series of peaks is achieved.

The foregoing description of preferred embodiments of the invention has been presented for purposes of illustration and description. It is not intended to be exhaustive or to limit the invention to the precise forms disclosed. Obviously, many modifications and variations will be apparent to practitioners skilled in this art and are intended to fall within the scope of the invention.

What is claimed is:

1. A fluorescently-labeled reagent comprising a reagent and an energy transfer dye, wherein energy transfer dye is covalently linked to the reagent and comprises:
    a xanthene donor dye capable of absorbing light at a first wavelength and emitting excitation energy in response thereto;
    a 4,7-dichlororhodamine acceptor dye capable of absorbing the excitation energy emitted by the donor dye and fluorescing at a second wavelength in response thereto; and
    a non-nucleosidic linker linking the xanthene donor dye to the 4,7-dichlororhodamine acceptor dye.

2. The fluorescently-labeled reagent of claim 1 in which the non-nucleosidic linker links the xanthene donor dye to the 4'-, 5- or 6-position of the 4,7-dichlororhodamine acceptor dye.

3. The fluorescently-labeled reagent of claim 1 in which the linker has a backbone that is less than 9 atoms in length.

4. The fluorescently-labeled reagent of claim 1 in which the linker comprises a functional group selected from an alkene, a diene, an alkyne, a five membered ring having at least one unsaturated bond, a six membered ring having at least one unsaturated bond and a fused ring structure.

5. The fluorescently-labeled reagent of claim 1 in which the reagent is selected from the group consisting of proteins, polypeptides, polysaccharides, nucleosides/tides, oligonucleotides, oligonucleotide analogs, lipids, solid supports and organic and inorganic polymers.

6. The fluorescently-labeled reagent of claim 5 in which the reagent is a nucleoside/tide.

7. The fluorescently-labeled reagent of claim 6 in which the xanthene donor dye is a fluorescein dye.

8. The fluorescenlty-labeled reagent of claim 7 in which the non-nucleosidic linker links the 4'-, 5- or 6-position of the fluorescein donor dye to the 4'-, 5- or 6-position of the 4,7-dichlororhodamine dye.

9. The fluorescently labeled reagent of claim 8 in which energy transfer dye is covalently linked to the base of the nucleoside/tide reagent via the 4'-, 5- or 6-position of the fluorescein donor dye or the 4'-position of the 4,7-dichlororhodamine acceptor dye.

10. The fluorescently labeled reagent of claim 9 in which energy transfer dye is covalently linked to the base of the nucleoside/tide reagent by way of an acetylenic amido or alkenic amido linkage.

11. The fluorescently labeled reagent of claim 10 in which the acetylenic amido or alkenic amido linkage is selected from —C≡C—CH$_2$—NH—C(O)—, 3-amino-1-propyn-1-yl, —C≡C—CH$_2$—NH—C(O)—(CH$_2$)$_5$—C(O)—, —C=CH—C(O)—NH—(CH$_2$)$_5$—NH—C(O)— and —C≡C—CH$_2$—O—CH$_2$—CH$_2$—NR—, where R is hydrogen, a protecting group or alkyl.

12. The fluorescently labeled reagent of claim 9 in which the nucleoside/tide is a 2'-deoxyribonucleoside.

13. The fluorescently labeled reagent of claim 9 in which the nucleoside/tide is a 2'-deoxyribonucleotide.

14. The fluorescently labeled reagent of claim 13 in which the 2'-deoxyribonucleotide is a 2'-deoxyribonucleoside-5'-triphosphate.

15. The fluorescently labeled reagent of claim 9 in which the nucleoside/tide is a terminating nucleotide.

16. The fluorescently labeled reagent of claim 15 in which the terminating nucleotide is a 2',3'-dideoxynucleoside-5'-triphosphate.

17. The fluorescently-labeled reagent of claim 9 in which the 4,7-dichlororhodamine acceptor dye comprises structure (I):

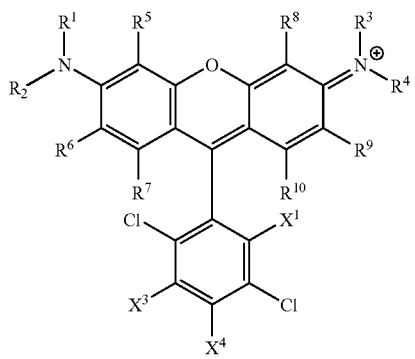

(I)

wherein:
R$^1$, R$^2$, R$^3$ and R$^4$ are each, independently of one another, selected from hydrogen and alkyl, or alternatively R$^1$ and R$^5$, R$^2$ and R$^6$, R$^3$ and R$^8$ and/or R$^4$ and R$^9$ are taken together with the atoms to which they are bonded to form a 5, 6 or 7-membered ring;
R$^5$, R$^6$, R$^7$, R$^8$, R$^9$ and R$^{10}$ are each, independently of one another, selected from hydrogen, fluorine, chlorine, bromine, iodine, carboxyl, alkyl, alkene, alkyne, sulfonate, sulfone, amino, ammonium, amido, nitrile, alkoxy, phenyl and substituted phenyl, or alternatively, R$^6$ and R$^7$ and/or R$^9$ and R$^{10}$ are taken together with the atoms to which they are bonded to form a benzo group;

X$^1$, X$^3$ and X$^4$ are each, independently of one another, selected from hydrogen, fluorine, chlorine, bromine, iodine, carboxyl, alkyl, alkene, alkyne, sulfonate, sulfone, amino, ammonium, amido, nitrile and alkoxy; and
R$^8$, X$^3$ or X$^4$ comprises the linker linking the xanthene donor dye.

18. The fluorescently-labeled reagent of claim 9 in which the fluorescein donor dye comprises structure (II):

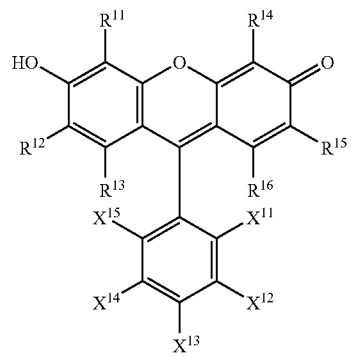

(II)

wherein:
R$^{11}$, R$^{12}$, R$^{13}$, R$^{14}$, R$^{15}$ and R$^{16}$ are each, independently of one another, selected from hydrogen, fluorine, chlorine, bromine, iodine, carboxyl, alkyl, alkene, alkyne, sulfonate, sulfone, amino, ammonium, amido, nitrile, alkoxy, phenyl and substituted phenyl, or alternatively, R$^{12}$ and R$^{13}$ and/or R$^{15}$ and R$^{16}$ are taken together with the atoms to which they are bonded to form a benzo group;
X$^{11}$, X$^{12}$, X$^{13}$, X$^{14}$ and X$^{15}$ are each, independently of one another, selected from hydrogen, fluorine, chlorine, bromine, iodine, carboxyl, alkyl, alkene, alkyne, sulfonate, sulfone, amino, ammonium, amido, nitrile and alkoxy; and
R$^{14}$, X$^{13}$ or X$^{14}$ comprises the linker linking the 4,7-dichlororhodamine acceptor dye.

19. The fluorescently-labeled reagent of claim 9 in which energy transfer dye comprises structure (III):

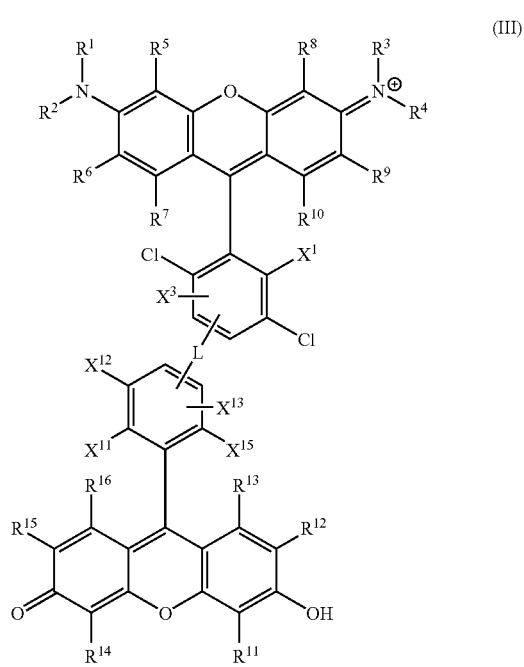

(III)

wherein:
- $R^1$, $R^2$, $R^3$ and $R^4$ are each, independently of one another, selected from hydrogen, methyl and ethyl, or alternatively $R^1$ and $R^5$, $R^2$ and $R^6$, $R^3$ and $R^5$ and/or $R^4$ and $R^9$ are taken together with the atoms to which they are bonded to form a 5, 6 or 7-membered ring;
- $R^5$, $R^6$, $R^7$, $R^8$, $R^9$ and $R^{10}$ are each, independently of one another, selected from hydrogen, fluorine, chlorine, bromine, iodine, carboxyl, alkyl, alkene, alkyne, sulfonate, sulfone, amino, ammonium, amido, nitrile, alkoxy, phenyl and substituted phenyl, or alternatively, $R^6$ and $R^7$ and/or $R^9$ and $R^{10}$ are taken together with the atoms to which they are bonded to form a benzo group;
- $X^1$ and $X^3$ are each, independently of one another, selected from hydrogen, fluorine, chlorine, bromine, iodine, carboxyl, alkyl, alkene, alkyne, sulfonate, sulfone, amino, ammonium, amido, nitrile and alkoxy;
- L is the non-nucleosidic linker;
- $R^{11}$, $R^{12}$, $R^{13}$, $R^{14}$, $R^{15}$ and $R^{16}$ are each, independently of one another, selected from hydrogen, fluorine, chlorine, bromine, iodine, carboxyl, alkyl, alkene, alkyne, sulfonate, sulfone, amino, ammonium, amido, nitrile, alkoxy, phenyl and substituted phenyl, or alternatively, $R^{12}$ and $R^{13}$ and/or $R^{15}$ and $R^{16}$ are taken together with the atoms to which they are bonded to form a benzo group; and
- $X^{11}$, $X^{12}$, $X^{13}$ and $X^{15}$ are each, independently of one another, selected from hydrogen, fluorine, chlorine, bromine, iodine, carboxyl, alkyl, alkene, alkyne, sulfonate, sulfone, amino, ammonium, amido, nitrile and alkoxy,
- with the proviso that one of $R^8$ or $X^{14}$ comprises a linkage that covalently links the energy transfer dye to the nucleoside/tide reagent.

20. The fluorescently-labeled reagent of claim 9 in which energy transfer dye comprises structure (IV):

(IV)

wherein:
- $R^1$, $R^2$, $R^3$ and $R^4$ are each, independently of one another, selected from hydrogen, methyl and ethyl, or alternatively $R^1$ and $R^5$, $R^2$ and $R^6$, $R^3$ and $R^5$ and/or $R^4$ and $R^9$ are taken together with the atoms to which they are bonded to form a 5, 6 or 7-membered ring;
- $R^5$, $R^6$, $R^7$, $R^8$, $R^9$ and $R^{10}$ are each, independently of one another, selected from hydrogen, fluorine, chlorine, bromine, iodine, carboxyl, alkyl, alkene, alkyne, sulfonate, sulfone, amino, ammonium, amido, nitrile, alkoxy, phenyl and substituted phenyl, or alternatively, $R^6$ and $R^7$ and/or $R^9$ and $R^{10}$ are taken together with the atoms to which they are bonded to form a benzo group;
- $X^1$ and $X^3$ are each, independently of one another, selected from hydrogen, fluorine, chlorine, bromine, iodine, carboxyl, alkyl, alkene, alkyne, sulfonate, sulfone, amino, ammonium, amido, nitrile and alkoxy;
- L is the non-nucleosidic linker;
- $R^{11}$, $R^{12}$, $R^{13}$, $R^{14}$, $R^{15}$ and $R^{16}$ are each, independently of one another, selected from hydrogen, fluorine, chlorine, bromine, iodine, carboxyl, alkyl, alkene, alkyne, sulfonate, sulfone, amino, ammonium, amido, nitrile, alkoxy, phenyl and substituted phenyl, or alternatively, $R^{12}$ and $R^{13}$ and/or $R^{15}$ and $R^{16}$ are taken together with the atoms to which they are bonded to form a benzo group; and
- $X^{11}$, $X^{12}$, $X^{13}$, $X^{14}$ and $X^{15}$ are each, independently of one another, selected from hydrogen, fluorine, chlorine, bromine, iodine, carboxyl, alkyl, alkene, alkyne, sulfonate, sulfone, amino, ammonium, amido, nitrile and alkoxy,
- with the proviso that one of $R^8$, $X^{13}$ or $X^{14}$ comprises a linkage that covalently links the energy transfer dye to the nucleoside/tide reagent.

21. The fluorescently labeled reagent of claim 19 or claim 20 in which $X^1$ is carboxylate.

22. The fluorescently labeled reagent of claim 21 in which $R^1$, $R^2$, $R^3$, $R^4$, $R^5$, $R^6$, $R^7$, $R^8$, $R^9$, $R^{10}$ and $X^3$ are each hydrogen.

23. The fluorescently labeled reagent of claim 21 in which $R^1$, $R^3$, $R^5$, $R^7$, $R^8$, $R^{10}$ and $X^3$ are each hydrogen; $R^2$ and $R^4$ are each ethyl; and $R^6$ and $R^9$ are each methyl.

24. The fluorescently labeled reagent of claim 21 in which $R^1$, $R^2$, $R^3$ and $R^4$ are each methyl; and $R^5$, $R^6$, $R^7$, $R^8$, $R^9$, $R^{10}$ and $X^3$ are each hydrogen.

25. The fluorescently labeled reagent of claim 21 in which $R^1$ and $R^5$, $R^2$ and $R^6$, $R^3$ and $R^8$ and $R^4$ and $R^9$ are taken together with the atoms to which they are bonded to form six-membered rings; and $R^7$, $R^{10}$ and $X^3$ are each hydrogen.

26. The fluorescently labeled reagent of claim 21 in which $R^1$, $R^3$, $R^4$, $R^5$, $R^7$, $R^8$, $R^9$, $R^{10}$ and $X^3$ are each hydrogen; $R^2$ is ethyl; and $R^6$ is methyl.

27. The fluorescently labeled reagent of claim 21 in which $R^1$, $R^5$, $R^7$, $R^8$, $R^9$, $R^{10}$ and $X^3$ are each hydrogen; $R^3$, $R^4$ and $R^6$ are each methyl; and $R^2$ is ethyl.

28. The fluorescently labeled reagent of claim 21 in which $R^5$, $R^6$, $R^7$, $R^{10}$ and $X^3$ are each hydrogen; $R^1$ and $R^2$ are each methyl; and $R^3$ and $R^8$ and $R^4$ and $R^9$ are taken together with the atoms to which they are bonded to form six-membered rings.

29. The fluorescently labeled reagent of claim 21 in which $R^1$, $R^2$, $R^5$, $R^6$, $R^7$, $R^{10}$ and $X^3$ are each hydrogen; and $R^3$ and $R^8$ and $R^4$ and $R^9$ are taken together with the atoms to which they are bonded to form six-membered rings.

30. The fluorescently labeled reagent of claim 21 in which $R^1$, $R^5$, $R^6$, $R^7$, $R^{10}$ and $X^3$ are each hydrogen; $R^2$ is ethyl; and $R^3$ and $R^8$ and $R^4$ and $R^9$ are taken together with the atoms to which they are bonded to form six-membered rings.

31. The fluorescently labeled reagent of claim 21 in which $R^1$, $R^2$, $R^5$, $R^6$, $R^7$, $R^8$, $R^9$, $R^{10}$ and $X^3$ are each hydrogen; and $R^3$ and $R^4$ are each methyl.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
       (A) LENGTH: 1217 nucleotides
       (B) TYPE: nucleic acid
       (C) STRANDEDNESS: single
       (D) TOPOLOGY: linear (xi) SEQUENCE DESCRIPTION: SEQ ID NO: 1:

```
GCCAAGCTTG  CATGCCTGCA  GGTCGACTCT  AGAGGATCCC                    40
CGGGTACCGA  GCTCGAATTC  GTAATCATGG  TCATAGCTGT                    80
TTCCTGTGTG  AAATTGTTAT  CCGCTCACAA  TTCCACACAA                   120
CATACGAGCC  GGAAGCATAA  AGTGTAAAGC  CTGGGGTGCC                   160
TAATGAGTGA  GCTAACTCAC  ATTAATTGCG  TTGCGCTCAC                   200
TGCCCGCTTT  CCAGTCGGGA  AACCTGTCGT  GCCAGCTGCA                   240
TTAATGAATC  GGCCAACGCG  CGGGGAGAGG  CGGTTTGCGT                   280
ATTGGGCGCC  AGGGTGGTTT  TTCTTTTCAC  CAGTGAGACG                   320
GGCAACAGCT  GATTGCCCTT  CACCGCCTGG  CCCTGAGAGA                   360
GTTGCAGCAA  GCGGTCCACG  CTGGTTTGCC  CCAGCAGGCG                   400
AAAATCCTGT  TTGATGGTGG  TTCCGAAATC  GGCAAAATCC                   440
CTTATAAATC  AAAAGAATAG  CCCGAGATAG  GGTTGAGTGT                   480
TGTTCCAGTT  TGGAACAAGA  GTCCACTATT  AAAGAACGTG                   520
GACTCCAACG  TCAAAGGGCG  AAAAACCGTC  TATCAGGGCG                   560
ATGGCCCACT  ACGTGAACCA  TCACCCAAAT  CAAGTTTTTT                   600
GGGGTCGAGG  TGCCGTAAAG  CACTAAATCG  GAACCCTAAA                   640
GGGAGCCCCC  GATTTAGAGC  TTGACGGGGA  AAGCCGGCGA                   680
ACGTGGCGAG  AAAGGAAGGG  AAGAAAGCGA  AAGGAGCGGG                   720
CGCTAGGGCG  CTGGCAAGTG  TAGCGGTCAC  GCTGCGCGTA                   760
ACCACCACAC  CCGCCGCGCT  TAATGCGCCG  CTACAGGGCG                   800
CGTACTATGG  TTGCTTTGAC  GAGCACGTAT  AACGTGCTTT                   840
CCTCGTTGGA  ATCAGAGCGG  GAGCTAAACA  GGAGGCCGAT                   880
TAAAGGGATT  TTAGACAGGA  ACGGTACGCC  AGAATCTTGA                   920
GAAGTGTTTT  TATAATCAGT  GAGGCCACCG  AGTAAAAGAG                   960
TCTGTCCATC  ACGCAAATTA  ACCGTTGTAG  CAATACTTCT                  1000
TTGATTAGTA  ATAACATCAC  TTGCCTGAGT  AGAAGAACTC                  1040
AAACTATCGG  CCTTGCTGGT  AATATCCAGA  ACAATATTAC                  1080
CGCCAGCCAT  TGCAACAGGA  AAAACGCTCA  TGGAAATACC                  1120
TACATTTTGA  CGCTCAATCG  TCTGAAATGG  ATTATTTACA                  1160
TTGGCAGATT  CACCAGTCAC  ACGACCAGTA  ATAAAGGGA                   1200
CATTCTGGCC  AACAGAG                                             1217
```

-continued (2) INFORMATION FOR SEQ ID NO: 2:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (xi) SEQUENCE DESCRIPTION: SEQ ID NO: 2:

```
TGTAAAACGA  CGGCCAGT                                           18
```

(2) INFORMATION FOR SEQ ID NO: 3:

(i) SEQUENCE CHARACTERISTICS:
        (A) LENGTH: 738 nucleotides
        (B) TYPE: nucleic acid
        (C) STRANDEDNESS: single
        (D) TOPOLOGY: linear (xi) SEQUENCE DESCRIPTION: SEQ ID NO: 3:

```
ATACGACTCA  CTATAGGGCG  AATTCGAGCT  CGGTACCCGG                 40
GGATCCTCTA  GAGTCGACCT  GCAGGCATGC  AAGCTTGAGT                 80
ATTCTATAGT  GTCACCTAAA  TAGCTTGGCG  TAATCATGGT                120
CATAGCTGTT  TCCTGTGTGA  AATTGTTATC  CGCTCACAAT                160
TCCACACAAC  ATACGAGCCG  GAAGCATAAA  GTGTAAAGCC                200
TGGGGTGCCT  AATGAGTGAG  CTAACTCACA  TTAATTGCGT                240
TGCGCTCACT  GCCCGCTTTC  CAGTCGGGAA  ACCTGTCGTG                280
CCAGCTGCAT  TAATGAATCG  GCCAACGCGC  GGGGAGAGGC                320
GGTTTGCGTA  TTGGGCGCTC  TTCCGCTTCC  TCGCTCACTG                360
ACTCGCTGCG  CTCGGTCGTT  CGGCTGCGGC  GAGCGGTATC                400
AGCTCACTCA  AAGGCGGTAA  TACGGTTATC  CACAGAATCA                440
GGGGATAACG  CAGGAAAGAA  CATGTGAGCA  AAAGGCCAGC                480
AAAAGGCCAG  GAACCGTAAA  AAGGCCGCGT  TGCTGGCGTT                520
TTTCCATAGG  CTCCGCCCCC  CTGACGAGCA  TCACAAAAAT                560
CGACGCTCAA  GTCAGAGGTG  GCGAAACCCG  ACAGGACTAT                600
AAAGATACCA  GGCGTTTCCC  CCTGGAAGCT  CCCTCGTGCG                640
CTCTCCTGTT  CCGACCCTGC  CGCTTACCGG  ATACCTGTCC                680
GCCTTTCTCC  CTTCGGGAAG  CGTGGCGCTT  TCTCATAGCT                720
CACGCTGTAG  GTATCTCA                                         738
```